US009944641B2

(12) United States Patent
Kaloun et al.

(10) Patent No.: US 9,944,641 B2
(45) Date of Patent: Apr. 17, 2018

(54) ISOQUINOLINONE DERIVATIVES USEFUL IN THE TREATMENT OF CANCER

(71) Applicant: PIERRE FABRE MEDICAMENT, Boulogne-Billancourt (FR)

(72) Inventors: El Bachir Kaloun, Roquettes (FR); Philippe Schmitt, Nailloux (FR); Anna Kruczynski, Pompertuzat (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 15/507,941

(22) PCT Filed: Sep. 2, 2015

(86) PCT No.: PCT/EP2015/070082
§ 371 (c)(1),
(2) Date: Mar. 1, 2017

(87) PCT Pub. No.: WO2016/034642
PCT Pub. Date: Mar. 10, 2016

(65) Prior Publication Data
US 2017/0240544 A1    Aug. 24, 2017

(30) Foreign Application Priority Data
Sep. 2, 2014    (EP) .................................... 14306352

(51) Int. Cl.
*C07D 471/04*    (2006.01)
*A61K 31/519*    (2006.01)
*A61K 45/06*    (2006.01)

(52) U.S. Cl.
CPC .......... *C07D 471/04* (2013.01); *A61K 31/519* (2013.01); *A61K 45/06* (2013.01)

(58) Field of Classification Search
CPC ..... C07D 471/04; C07D 519/00; A61K 31/52
See application file for complete search history.

(56) References Cited

FOREIGN PATENT DOCUMENTS

| WO | WO 2012/102985 A1 | 8/2012 | |
|----|-------------------|--------|---|
| WO | WO 2013/041539 A1 | 3/2013 | |
| WO | WO 2013/126656    | * 8/2013 | ........... C07D 471/04 |
| WO | WO 2013/126656 A1 | 8/2013 | |

OTHER PUBLICATIONS

West, Anthony R., Solid State Chemistry and Its Applications, Wiley, New York, 1988, 358.*

Cook et al., "Role of altered growth factor receptor-mediated JAK2 signaling in growth and maintenance of human acute myeloid leukemia stem cells," Blood, vol. 123, No. 18, May 1, 2014, pp. 2826-2837 (13 pages total).
Extended European Search Report issued in European Application No. 14306352.7, dated Nov. 25, 2014.
Fresneau et al., "Synthesis of substituted diazino[c]quinolin-5(6H)-ones, diazino[c]isoquinolin-6(5H)-ones, diazino[c]naphthyridin-6(5H)-ones and diazino[c]naphthyridin-5(6H)-ones," Tetrahedron, vol. 69, 2013 (available online Apr. 28, 2013), pp. 5393-5400.
Gilliland et al., "The roles of FLT3 in hematopoiesis and leukemia," Blood, vol. 100, No. 5, Sep. 1, 2002, pp. 1532-1542 (12 pages total).
International Search Report and Written Opinion of the International Searching Authority (Forms PCT/ISA/220, PCT/ISA/210 and PCT/ISA/237) issued in International Application No. PCT/EP2015/070082, dated Oct. 29, 2015.
Kayser et al., "FLT3 tyrosine kinase inhibitors in acute myeloid leukemia: clinical implications and limitations," NIH Public Access Author Manuscript, published in final edited form in Leukemia & Lymphoma, vol. 55, No. 2, Feb. 2014, pp. 243-255 (24 pages total).
Marini et al., "Synthesis and in vitro Antiproliferative Activity of New Substituted Benzo[3',2':5,6]thiopyrano[4,3-d]pyrimidines," Journal of Heterocyclic Chemistry, vol. 45, No. 3, May-Jun. 2008, pp. 745-749.
Weisberg et al., "Using combination therapy to override stromal-mediated chemoresistance in mutant FLT3-positive AML: Synergism . . . and JAK inhibitors," NIH Public Access Author Manuscript, published in final edited form in Leukemia, vol. 26, No. 10, Oct. 2012, pp. 2233-2244 (24 pages total).
Zhang et al., "Mechanism-based design, synthesis and biological studies of $N^5$-substituted tetrahydrofolate analogs . . . potential anticancer agents," European Journal of Medicinal Chemistry, vol. 58, 2012 (available online Oct. 9, 2012), pp. 228-236.

* cited by examiner

*Primary Examiner* — Erich A Leeser
(74) *Attorney, Agent, or Firm* — Birch, Stewart, Kolasch & Birch, LLP

(57)    ABSTRACT

The present invention relates to a compound of the following formula (I) or a pharmaceutically acceptable salt and/or solvate thereof, notably for use as a drug, notably in the treatment of cancer, as well as pharmaceutical compositions containing such a compound and processes to prepare such a compound.

22 Claims, No Drawings

ISOQUINOLINONE DERIVATIVES USEFUL IN THE TREATMENT OF CANCER

The present invention relates to isoquinolinone derivatives, in particular for their use as a drug, notably in the treatment of cancers, synthetic procedures for preparing them and pharmaceutical compositions containing such compounds.

Mutations within receptor tyrosine kinases occupy a very central role in the pathogenesis of numerous cancers. FLT3 for example is frequently mutated (about 30% of patients) in Acute Myeloid Leukemia (AML: Gilliland et al. *Blood* 2002, 100, 1532-1542). These mutations promote the enzymatic activity of the corresponding enzyme which happens to be a key driver of the tumour cell proliferation and survival. For such reasons, these mutated proteins represent validated target in oncology.

Three main FLT3 activating mutations are now known for AML: FLT3-ITD (internal tandem duplication) in about 20% of patients, FLT3-TKD (Tyrosine Kinase Domain) in about 6 to 8% of patients and punctual mutations in the juxtamembrane and extracellular domain which are rare (2%: Kayser et al. *Leukemia & Lymphoma* 2014, 55, 243-255).

Recent clinical evaluations of newest generation FLT3 inhibitors have shown promising results in FLT3 mutated AMLs. Even though encouraging, these responses still remain incomplete, transient as well as associated with a high rate of relapse (Kayser et al. *Leukemia & Lymphoma* 2014, 55, 243-255).

Relapses are caused by multiple mechanisms. Secondary mutations within the FLT3 receptor generate resistance toward the administered inhibitor and activation of alternate signalling pathways that by-pass the inhibited kinases and re-activate the downstream effectors of FLT3.

Moreover, whereas freely circulating leukemic cells may be relatively sensitive to TKI (tyrosine kinase inhibitors), cells located in the bone marrow of the patient, particularly leukemia stem cells (LSCs), may beneficiate from a favourable survival stromal micro-environment which make them less responsive to treatment and more prone to relapse initiation (Weisberg et al. *Leukemia* 2012, 26, 2233-2244). Among the survival factors present in the bone marrow sanctuary, the IL-6/JAK/STAT pathway has been proposed as a major contributor to the relapse rate of current TKI in AML associated with mutated FLT3 (Bhatia et al. *Blood* 2014, 123, 2826-2837).

The drug combination of both JAK and FLT3 inhibitors has shown synergistic actions as well as capabilities to overcome the stroma-induced resistance establishment (Weisberg et al. *Leukemia* 2012, 26, 2233-2244); re-enforcing experimentally the proposal of an increased medical benefit for FLT3-JAK dual inhibitors.

In order to minimize adverse effect and increase tolerance, drugs with a minimum activity on wild-type FLT3 isoforms while having a maximum efficacy of mutated isoforms are expected to present an improvement compared to current less selective drugs.

Globally these data suggest that new and more potent FLT3-JAK dual inhibitors may prove to offer a better outcome for patient with high-risk AML.

Thus, the present invention provides compounds having a dual activity as JAK inhibitors and FLT3 inhibitors.

The present invention relates thus to a compound of the following formula (I):

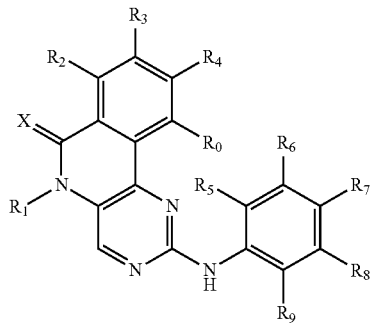

or a pharmaceutically acceptable salt and/or solvate thereof, wherein:

X is selected from O, NH and S, $R_0$ is H; halo (F, Cl, Br or I); $(C_1-C_6)$alkyl; $(C_1-C_6)$haloalkyl; $(C_1-C_6)$alkoxy; or $(C_1-C_6)$haloalkoxy, $R_1$ is selected from H and $(C_1-C_3)$alkyl, $R_2$, $R_3$, $R_5$, $R_7$, $R_8$ and $R_9$ are, independently of one another, selected from H; halo (F, Cl, Br or I); nitro ($NO_2$); cyano (CN); $R_{10}$; $OR_{11}$; $SR_{12}$; $S(O)R_{13}$; $SO_2R_{14}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated heterocycle, comprising one to three heteroatoms chosen from O, N and S, optionally substituted with one or several groups selected from halo (F, Cl, Br or I), nitro ($NO_2$), cyano (CN), oxo (=O), $(C_1-C_6)$alkyl, OH, $CO_2H$, $(C_1-C_6)$alkoxy, $CO_2$—$(C_1-C_6)$alkyl and $NR_{24}R_{25}$, $R_4$ and $R_6$ are, independently of each other, selected from H; halo (F, Cl, Br or I); nitro ($NO_2$); cyano (CN); $R_{10}$; $OR_{11}$; $SR_{12}$; $S(O)R_{13}$; $SO_2R_{14}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated heterocycle comprising one to three heteroatoms chosen from O, N and S, optionally substituted with one or several groups selected from halo (F, Cl, Br or I), nitro ($NO_2$), cyano (CN), oxo (=O), $(C_1-C_6)$alkyl, OH, $CO_2H$, $(C_1-C_6)$alkoxy, $CO_2$—$(C_1-C_6)$alkyl and $NR_{24}R_{25}$, or $R_4$ and $R_6$ form together a hydrocarbon chain comprising 4 to 10 carbon atoms optionally substituted with one or several groups selected from halo (F, Cl, Br or I) and $(C_1-C_6)$alkyl, where one or several, notably one to five, non-adjacent carbon atoms of the saturated hydrocarbon chain are optionally replaced with O, S or $NR_{30}$, preferably with O, $R_{10}$, $R_{11}$, $R_{12}$, $R_{13}$, $R_{14}$, $R_{17}$, $R_{18}$, $R_{19}$, $R_{22}$, $R_{23}$ and $R_{30}$ are, independently of one another, H or a $(C_1-C_6)$alkyl, $(C_2-C_6)$alkenyl or $(C_2-C_6)$alkynyl group optionally substituted with one or several groups selected from halo (F, Cl, Br or I), nitro ($NO_2$), cyano (CN), OH, $CO_2H$, $(C_1-C_6)$alkoxy, $CO_2$—$(C_1-C_6)$alkyl and $NR_{26}R_{27}$, $R_{15}$, $R_{16}$, $R_{20}$ and $R_{21}$ are, independently of one another, H or a $(C_1-C_6)$alkyl, $(C_2-C_6)$alkenyl or $(C_2-C_6)$alkynyl group optionally substituted with one or several groups selected from halo (F, Cl, Br or I), nitro ($NO_2$), cyano (CN), OH, $CO_2H$, $(C_1-C_6)$alkoxy, $CO_2$—$(C_1-C_6)$alkyl and $NR_{26}R_{27}$, or $R_{15}$ and $R_{16}$ and/or $R_{20}$ and $R_{21}$ form together, with the nitrogen atom which carries them, a 3- to 7-membered saturated or unsaturated heterocycle optionally comprising one or two heteroatoms chosen from O, N and S in addition to the nitrogen atom, optionally substituted with one or several groups selected from halo (F, Cl, Br or I), nitro ($NO_2$), cyano (CN), oxo (=O), ($C_1$-$C_6$)alkyl, OH, $CO_2H$, ($C_1$-$C_6$)alkoxy, $CO_2$—($C_1$-$C_6$)alkyl and $NR_{28}R_{29}$, and $R_{24}$, $R_{25}$, $R_{26}$, $R_{27}$, $R_{28}$ and $R_{29}$ are, independently of each other, H or a ($C_1$-$C_6$)alkyl group, or $R_{24}$ and $R_{25}$ and/or $R_{26}$ and $R_{27}$ and/or $R_{28}$ and $R_{29}$ form together, with the nitrogen atom which carries them, a 3- to 7-membered saturated or unsaturated heterocycle optionally comprising one or two heteroatoms chosen from O, N and S in addition to the nitrogen atom, optionally substituted with one or several groups selected from halo (F, Cl, Br or I), oxo (=O) and ($C_1$-$C_6$)alkyl.

For the purpose of the invention, the term "pharmaceutically acceptable" is intended to mean what is useful to the preparation of a pharmaceutical composition, and what is generally safe and non toxic, for a pharmaceutical use.

The term <<pharmaceutically acceptable salt and/or solvate>> is intended to mean, in the framework of the present invention, a salt and/or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The term "halo", as used in the present invention, refers to bromo, chloro, iodo or fluoro.

The term "($C_1$-$C_3$)alkyl", as used in the present invention, refers to a straight or branched saturated hydrocarbon chain containing from 1 to 3 carbon atoms and including thus methyl, ethyl, n-propyl and iso-propyl.

The term "($C_1$-$C_6$)alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "($C_1$-$C_6$)haloalkyl", as used in the present invention, refers to a ($C_1$-$C_6$)alkyl group as defined above substituted by one or several halogen atoms, in particular one or several fluorine atoms. It can be in particular a trifluoromethyl group.

The term "($C_2$-$C_6$)alkenyl", as used in the present invention, refers to a straight or branched unsaturated hydrocarbon chain containing from 2 to 6 carbon atoms and comprising at least one double bond including, but not limited to, ethenyl, propenyl, butenyl, pentenyl, hexenyl and the like.

The term "($C_2$-$C_6$)alkynyl", as used in the present invention, refers to a straight or branched unsaturated hydrocarbon chain containing from 2 to 6 carbon atoms and comprising at least one triple bond including, but not limited to, ethynyl, propynyl, butynyl, pentynyl, hexynyl and the like.

The term "($C_1$-$C_6$)alkoxy", as used in the present invention, refers to a ($C_1$-$C_6$)alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like.

The term "($C_1$-$C_6$)haloalkoxy", as used in the present invention, refers to a ($C_1$-$C_6$)alkoxy group as defined above substituted by one or several halogen atoms, in particular one or several fluorine atoms. It can be in particular a trifluoromethoxy group.

The term "($C_1$-$C_6$)alkylamino", as used in the present invention, refers to a group of formula —NHAlk with Alk representing a ($C_1$-$C_6$)alkyl group as defined above. It can be for example methylamino, ethylamino, n-propylamino, iso-propylamino, n-butylamino, iso-butylamino, sec-butylamino, t-butylamino, n-pentylamino, n-hexylamino, and the like.

The term "di($C_1$-$C_6$)alkylamino", as used in the present invention, refers to a group of formula —$NHAlk_1Alk_2$ with $Alk_1$ and $Alk_2$ each representing independently a ($C_1$-$C_6$) alkyl group as defined above. It can be for example dimethylamino, diethylamino, ethylmethylamino, n-propylmethylamino, iso-propylmethylamino, n-butylmethylamino, iso-butylmethylamino, sec-butylmethylamino, t-butylmethylamino, n-pentylmethylamino, n-hexylmethylamino, and the like.

The term "(($C_1$-$C_6$)alkyl)-carbonyloxy", as used in the present invention, refers to a group of formula —OCOAlk with Alk representing a ($C_1$-$C_6$)alkyl group as defined above. It can be for example methylcarbonyloxy (acetoxy), ethylcarbonyloxy, n-propylcarbonyloxy, iso-propylcarbonyloxy, n-butylcarbonyloxy, iso-butylcarbonyloxy, sec-butylcarbonyloxy, t-butylcarbonyloxy, n-pentylcarbonyloxy, n-hexylcarbonyloxy, and the like.

The term "(($C_1$-$C_6$)alkyl)-carbonylamino", as used in the present invention, refers to a group of formula —NHCOAlk with Alk representing a ($C_1$-$C_6$)alkyl group as defined above. It can be for example methylcarbonylamino, ethylcarbonylamino, n-propylcarbonylamino, iso-propylcarbonylamino, n-butylcarbonylamino, iso-butylcarbonylamino, sec-butylcarbonylamino, t-butylcarbonylamino, n-pentylcarbonylamino, n-hexylcarbonylamino, and the like.

The term "(($C_1$-$C_6$)alkyl)-carbonyl(($C_1$-$C_6$)alkyl)amino)", as used in the present invention, refers to a group of formula —$NAlk_1COAlk_2$ with $Alk_1$ and $Alk_2$ each representing independently a ($C_1$-$C_6$)alkyl group as defined above. It can be for example (methylcarbonyl)methylamino, (methylcarbonyl)ethylamino, (ethylcarbonyl)methylamino, (ethylcarbonyl)ethylamino, n-propylcarbonylmethylamino, iso-propylcarbonylmethylamino, n-butylcarbonylmethylamino, iso-butylcarbonylmethylamino, sec-butylcarbonylmethylamino, t-butylcarbonylmethylamino, n-pentylcarbonylmethylamino, n-hexylcarbonylmethylamino, and the like.

The term "aryl", as used in the present invention, refers to an aromatic hydrocarbon group comprising preferably 6 to 10 carbon atoms and comprising one or more fused rings, such as, for example, a phenyl or naphtyl group. Advantageously, it will be a phenyl group.

The term "aryl-($C_1$-$C_6$)alkyl", as used in the present invention, refers to an aryl group as defined above bound to the molecule via a ($C_1$-$C_6$)alkyl group as defined above. In particular, it is a benzyl group.

The term "($C_1$-$C_6$)alkyl-aryl", as used in the present invention, refers to a ($C_1$-$C_6$)alkyl group as defined above bound to the molecule via an aryl group as defined above. In particular, it can be a tolyl group ($CH_3Ph$).

The term "3- to 7-membered heterocycle", as used in the present invention, refers to a 3- to 7-membered hydrocarbon cycle in which one to three, preferably one or two, carbon atoms have been replaced with a heteroatom selected from O, N and S, preferably selected from O and N. It includes notably the following cycles: aziridine, azetidine, oxetane, thiooxetane, pyrrolidine, pyrroline, tetrahydrofurane, dihydrofurane, tetrahydrothiophene, dihydrothiophene, piperidine, dihydropyridine, tetrahydropyridine, pyrane, dihydropyrane, tetrahydropyrane, thiopyrane, dihydrothiopyrane, tetrahydrothiopyrane, morpholine, thiomorpholine, piperazine, azepane, diazepane, imidadole, imidazoline, pyrrole, pyrazole, pyridine, pyrazine, pyridazine piperidazine, and pyrimidine.

The term "unsaturated" heterocycle, as used in the present invention, refers to a heterocycle comprising one or several double bonds but which is not aromatic.

Advantageously, X is an oxygen or sulfur atom, preferably an oxygen atom.

$R_0$ will be more particularly H or halo, notably H.

$R_1$ will be more particularly a hydrogen atom or a methyl group.

When $R_4$ and $R_6$ form together a chain, this chain is a hydrocarbon chain, preferably saturated, comprising 4 to 10 carbon atoms optionally substituted with one or several groups selected from halo (F, Cl, Br or I) and ($C_1$-$C_6$)alkyl, where one or several, notably one to five, non-adjacent carbon atoms of the saturated hydrocarbon chain are optionally replaced with O, S or $NR_{30}$, preferably with O.

Advantageously, this chain comprises 4 to 10 carbon atoms, where one or several, notably one to five, non-adjacent carbon atoms of the saturated hydrocarbon chain are optionally replaced with O, S or $NR_{30}$, preferably with O. This chain can be more particularly a linear chain.

This chain formed by $R_4$ and $R_6$ together can be notably a chain of formula —$X_1$-A-$X_2$— where:

$X_1$ and $X_2$ are, independently of each other, O, S or $NR_{30}$, and preferably are O, and A is a hydrocarbon chain, preferably saturated, comprising 2 to 8 carbon atoms optionally substituted with one or several groups selected from halo (F, Cl, Br or I) and ($C_1$-$C_6$)alkyl, where one or several, notably one to five, non-adjacent carbon atoms of the saturated hydrocarbon chain are optionally replaced with O, S or $NR_{30}$, preferably with O.

In particular, A can be a saturated hydrocarbon chain comprising 2 to 8 carbon atoms, where one or several, notably one to five, non-adjacent carbon atoms of the saturated hydrocarbon chain are optionally replaced with O, S or $NR_{30}$, preferably with O. The chain will be more particularly linear.

Preferably, the chain formed by $R_4$ and $R_6$ together is a chain of formula —($OCH_2CH_2$)$_n$O— with n representing an integer comprised between 1 and 3, and more particularly with n=2.

In a first embodiment, $R_2$, $R_3$, $R_5$, $R_7$, $R_8$ and $R_9$ are, independently of one another, selected from H; halo (F, Cl, Br or I); nitro ($NO_2$); cyano (CN); $R_{10}$; $OR_{11}$; $SR_{12}$; $S(O)R_{13}$; $SO_2R_{14}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated (notably 5- or 6-membered saturated) heterocycle comprising one to three heteroatoms chosen from O, N and S, optionally substituted with one or several groups selected from halo (F, Cl, Br or I), nitro ($NO_2$), cyano (CN), oxo (=O), ($C_1$-$C_6$)alkyl, OH, $CO_2H$, ($C_1$-$C_6$)alkoxy, $CO_2$—($C_1$-$C_6$)alkyl and $NR_{24}R_{25}$, and $R_4$ and $R_6$ are, independently of each other, selected from H; halo (F, Cl, Br or I); nitro ($NO_2$); cyano (CN); $R_{10}$; $OR_{11}$; $SR_{12}$; $S(O)R_{13}$; $SO_2R_{14}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated (notably 5- or 6-membered saturated) heterocycle comprising one to three heteroatoms chosen from O, N and S, optionally substituted with one or several groups selected from halo (F, Cl, Br or I), nitro ($NO_2$), cyano (CN), oxo (=O), ($C_1$-$C_6$)alkyl, OH, $CO_2H$, ($C_1$-$C_6$)alkoxy, $CO_2$—($C_1$-$C_6$)alkyl and $NR_{24}R_{25}$, or $R_4$ and $R_6$ form together a chain as defined previously, such as a chain of formula —$X_1$-A-$X_2$— or —($OCH_2CH_2$)$_n$O—.

In a second embodiment, $R_2$, $R_3$, $R_5$, $R_7$, $R_8$ and $R_9$ are, independently of one another, selected from H; halo (F, Cl, Br or I); nitro ($NO_2$); cyano (CN); $R_{10}$; $OR_{11}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated (notably 5- or 6-membered saturated) heterocycle comprising one to three heteroatoms chosen from O and N, optionally substituted with one or several groups selected from halo (F, Cl, Br or I), nitro ($NO_2$), cyano (CN), oxo (=O), ($C_1$-$C_6$)alkyl, OH, $CO_2H$, ($C_1$-$C_6$)alkoxy, $CO_2$—($C_1$-$C_6$)alkyl and $NR_{24}R_{25}$, and $R_4$ and $R_6$ are, independently of one another, selected from H; halo (F, Cl, Br or I); nitro ($NO_2$); cyano (CN); $R_{10}$; $OR_{11}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated (notably 5- or 6-membered saturated) heterocycle comprising one to three heteroatoms chosen from O and N, optionally substituted with one or several groups selected from halo (F, Cl, Br or I), nitro ($NO_2$), cyano (CN), oxo (=O), ($C_1$-$C_6$)alkyl, OH, $CO_2H$, ($C_1$-$C_6$)alkoxy, $CO_2$—($C_1$-$C_6$)alkyl and $NR_{24}R_{25}$, or $R_4$ and $R_6$ form together a chain as defined previously, such as a chain of formula —$X_1$-A-$X_2$— or —($OCH_2CH_2$)$_n$O—.

In a third embodiment, $R_2$, $R_3$, $R_5$, $R_7$, $R_8$ and $R_9$ are, independently of one another, selected from H; halo (F, Cl, Br or I); nitro ($NO_2$); cyano (CN); $R_{10}$; $OR_{11}$; $NR_{15}R_{16}$; $OC(O)R_{19}$; $NR_{22}C(O)R_{23}$; and a 3- to 7-membered saturated or unsaturated (notably 5- or 6-membered saturated) heterocycle comprising one to three heteroatoms chosen from O and N, optionally substituted with one or several groups selected from halo (F, Cl, Br or I), nitro ($NO_2$), cyano (CN), oxo (=O), ($C_1$-$C_6$)alkyl, OH, ($C_1$-$C_6$)alkoxy and $NR_{24}R_{25}$, and $R_4$ and $R_6$ are, independently of each other, selected from H; halo (F, Cl, Br or I); nitro ($NO_2$); cyano (CN); $R_{10}$; $OR_{11}$; $NR_{15}R_{16}$; $OC(O)R_{19}$; $NR_{22}C(O)R_{23}$; and a 3- to 7-membered saturated or unsaturated (notably 5- or 6-membered saturated) heterocycle comprising one to three heteroatoms chosen from O and N, optionally substituted with one or several groups selected from halo (F, Cl, Br or I), nitro ($NO_2$), cyano (CN), oxo (=O), ($C_1$-$C_6$)alkyl, OH, ($C_1$-$C_6$)alkoxy and $NR_{24}R_{25}$ or $R_4$ and $R_6$ form together a chain as defined previously, such as a chain of formula —$X_1$-A-$X_2$— or —($OCH_2CH_2$)$_n$O—.

In the above mentioned embodiments, $R_5$ can be more particularly H, halo (F, Cl, Br or I), $(C_1\text{-}C_6)$alkyl or $(C_1\text{-}C_6)$alkoxy; preferably H or halo (F, Cl, Br or I) such as H or F.

In the above mentioned embodiments, $R_2$, $R_3$, $R_4$, $R_6$ and $R_9$ can be, independently of one another, H, halo (F, Cl, Br or I), $(C_1\text{-}C_6)$alkyl, OH, $(C_1\text{-}C_6)$alkoxy, $((C_1\text{-}C_6)$alkyl)-carbonyloxy, $NO_2$, $NH_2$, $(C_1\text{-}C_6)$alkylamino, di$(C_1\text{-}C_6)$alkylamino, $((C_1\text{-}C_6)$alkyl)-carbonylamino or $((C_1\text{-}C_6)$alkyl)-carbonyl$((C_1\text{-}C_6)$alkyl amino); in particular H, halo (F, Cl, Br or I), OH, $(C_1\text{-}C_6)$alkoxy, $NO_2$, $NH_2$, $(C_1\text{-}C_6)$alkylamino, di$(C_1\text{-}C_6)$alkylamino, $((C_1\text{-}C_6)$alkyl)-carbonylamino or $((C_1\text{-}C_6)$alkyl)-carbonyl$((C_1\text{-}C_6)$alkylamino). More particularly, $R_6$ and $R_9$ will represent, independently of each other, H, halo (F, Cl, Br or I), OH, $(C_1\text{-}C_6)$alkoxy, $NH_2$, $(C_1\text{-}C_6)$alkylamino or di$(C_1\text{-}C_6)$alkylamino, and $R_2$, $R_3$ and $R_4$ will represent, independently of one another, H, halo (F, Cl, Br or I), $(C_1\text{-}C_6)$alkyl, OH, $(C_1\text{-}C_6)$alkoxy, $((C_1\text{-}C_6)$alkyl)-carbonyloxy, $NO_2$, $NH_2$, $(C_1\text{-}C_6)$alkylamino, di$(C_1\text{-}C_6)$alkylamino, $((C_1\text{-}C_6)$alkyl)-carbonylamino or $((C_1\text{-}C_6)$alkyl)-carbonyl$((C_1\text{-}C_6)$alkyl amino); in particular H, halo (F, Cl, Br or I), OH, $(C_1\text{-}C_6)$alkoxy, $((C_1\text{-}C_6)$alkyl)-carbonyloxy, $NO_2$, $NH_2$, $(C_1\text{-}C_6)$alkylamino, di$(C_1\text{-}C_6)$alkylamino, $((C_1\text{-}C_6)$alkyl)-carbonylamino or $((C_1\text{-}C_6)$alkyl)-carbonyl$((C_1\text{-}C_6)$alkyl amino); notably H, OH, $(C_1\text{-}C_6)$alkoxy, $((C_1\text{-}C_6)$alkyl)-carbonyloxy, $NO_2$, $NH_2$, $(C_1\text{-}C_6)$alkylamino, di$(C_1\text{-}C_6)$alkylamino, $((C_1\text{-}C_6)$alkyl)-carbonylamino or $((C_1\text{-}C_6)$alkyl)-carbonyl$((C_1\text{-}C_6)$alkyl amino). More particularly, $R_2$ represents H, $R_3$ represents H, $NO_2$, $NH_2$, $(C_1\text{-}C_6)$alkylamino, di$(C_1\text{-}C_6)$alkylamino, $((C_1\text{-}C_6)$alkyl)-carbonylamino or $((C_1\text{-}C_6)$alkyl)-carbonyl$((C_1\text{-}C_6)$alkyl amino), and $R_4$ represents H, OH, $(C_1\text{-}C_6)$alkoxy or $((C_1\text{-}C_6)$alkyl)-carbonyloxy; notably H, OH or $(C_1\text{-}C_6)$alkoxy; such as H or $(C_1\text{-}C_6)$alkoxy.

In the above embodiments, $R_7$ and $R_8$ can be, independently of one another, H; halo (F, Cl, Br or I); nitro ($NO_2$); cyano (CN); $R_{10}$; $OR_{11}$; $NR_{15}R_{16}$; $OC(O)R_{19}$; $NR_{22}C(O)R_{23}$; or a 5- or 6-membered saturated or unsaturated (notably saturated) heterocycle comprising one or two heteroatoms chosen from O and N, optionally substituted with one or several groups selected from halo (F, Cl, Br or I), oxo (=O), $(C_1\text{-}C_6)$alkyl, OH, $(C_1\text{-}C_6)$alkoxy, $NH_2$, $(C_1\text{-}C_6)$alkylamino and di$(C_1\text{-}C_6)$alkylamino; notably H; halo (F, Cl, Br or I); cyano (CN); $R_{10}$; $OR_{11}$; $NR_{15}R_{16}$; or a 5- or 6-membered saturated heterocycle comprising one or two heteroatoms chosen from O and N, optionally substituted with one or several groups selected from halo (F, Cl, Br or I), oxo (=O), $(C_1\text{-}C_6)$alkyl, OH, $(C_1\text{-}C_6)$alkoxy, $NH_2$, $(C_1\text{-}C_6)$alkylamino and di$(C_1\text{-}C_6)$alkylamino; with:

$R_{10}$, $R_{11}$, $R_{19}$, $R_{22}$ and $R_{23}$ advantageously representing, independently of one another, H or a $(C_1\text{-}C_6)$alkyl group optionally substituted with one or several groups selected from halo (F, Cl, Br or I), OH, $(C_1\text{-}C_6)$alkoxy, and $NR_{26}R_{27}$, and $R_{15}$ and $R_{16}$ advantageously representing, independently of each other, H or a $(C_1\text{-}C_6)$alkyl group optionally substituted with one or several groups selected from halo (F, Cl, Br or I), OH, $(C_1\text{-}C_6)$alkoxy, and $NR_{26}R_{27}$, or $R_{15}$ and $R_{16}$ forming together, with the nitrogen atom which carries them, a 5- or 6-membered saturated or unsaturated, preferably saturated, heterocycle optionally comprising one heteroatom chosen from O and N in addition to the nitrogen atom carrying the $R_{15}$ and $R_{16}$ groups, optionally substituted with one or several groups selected from halo (F, Cl, Br or I), oxo (=O), $(C_1\text{-}C_6)$alkyl, OH, $(C_1\text{-}C_6)$alkoxy and $NR_{28}R_{29}$.

In the above mentioned embodiments for $R_2$, $R_3$, $R_4$, $R_5$, $R_6$, $R_7$, $R_8$ and $R_9$, the heterocycle can be a 3- to 7-membered saturated or unsaturated heterocycle comprising one to three, notably one or two, heteroatoms chosen from O, N and S, preferably chosen from O and N. In particular, it is a 5- to 7-membered, notably 5- or 6-membered, heterocycle, saturated or unsaturated, preferably saturated, comprising one or two heteroatoms chosen from O and N. The heterocycle can be selected from azetidine, oxetane, thiooxetane, pyrrolidine, pyrroline, tetrahydrofurane, dihydrofurane, tetrahydrothiophene, dihydrothiophene, piperidine, dihydropyridine, tetrahydropyridine, pyrane, dihydropyrane, tetrahydropyrane, thiopyrane, dihydrothiopyrane, tetrahydrothiopyrane, morpholine, thiomorpholine, piperazine, azepane, diazepane imidadole, imidazoline, pyrrole, pyrazole, pyridine, pyrazine, pyridazine piperidazine and pyrimidine. In particular, the heterocycle is selected from pyrrolidine, pyrroline, tetrahydrofurane, dihydrofurane, piperidine, dihydropyridine, tetrahydropyridine, pyrane, dihydropyrane, tetrahydropyrane, morpholine, piperazine, azepane, diazepane imidadole, imidazoline, pyrrole, pyrazole, pyridine, pyrazine, pyridazine, piperidazine, and pyrimidine. The heterocycle can notably be selected from pyrrolidine, tetrahydrofurane, piperidine, tetrahydropyrane, morpholine, piperazine, azepane, and diazepane. In particular, the heterocycle is selected from pyrrolidine, piperidine, morpholine, and piperazine.

In the above mentioned embodiments for $R_2$, $R_3$, $R_4$, $R_5$, $R_6$, $R_7$, $R_8$ and $R_9$, the $R_{10}$, $R_{11}$, $R_{12}$, $R_{13}$, $R_{14}$, $R_{17}$, $R_{18}$, $R_{19}$, $R_{22}$, $R_{23}$ and $R_{30}$ groups are as defined previously and advantageously are, independently of one another, H or a $(C_1\text{-}C_6)$alkyl group optionally substituted with one or several groups selected from halo (F, Cl, Br or I), nitro ($NO_2$), cyano (CN), OH, $CO_2H$, $(C_1\text{-}C_6)$alkoxy, $CO_2$—$(C_1\text{-}C_6)$alkyl and $NR_{26}R_{27}$, notably selected from halo (F, Cl, Br or I), nitro ($NO_2$), cyano (CN), OH, $(C_1\text{-}C_6)$alkoxy, and $NR_{26}R_{27}$, in particular selected from halo (F, Cl, Br or I), OH, $(C_1\text{-}C_6)$alkoxy, and $NR_{26}R_{27}$, and the $R_{15}$, $R_{16}$, $R_{20}$ and $R_{21}$ groups are as defined previously and advantageously are, independently of one another, H or a $(C_1\text{-}C_6)$alkyl group optionally substituted with one or several groups selected from halo (F, Cl, Br or I), nitro ($NO_2$), cyano (CN), OH, $CO_2H$, $(C_1\text{-}C_6)$alkoxy, $CO_2$—$(C_1\text{-}C_6)$alkyl and $NR_{26}R_{27}$, notably selected from halo (F, Cl, Br or I), nitro ($NO_2$), cyano (CN), OH, $(C_1\text{-}C_6)$alkoxy, and $NR_{26}R_{27}$, in particular selected from halo (F, Cl, Br or I), OH, $(C_1\text{-}C_6)$alkoxy, and $NR_{26}R_{27}$, or $R_{15}$ and $R_{16}$ and/or $R_{20}$ and $R_{21}$ form together, with the nitrogen atom which carries them, a 5- to 7-membered, notably 5- or 6-membered, saturated or unsaturated, preferably saturated, heterocycle optionally comprising one heteroatom chosen from O and N in addition to the nitrogen atom, optionally substituted with one or several groups selected from halo (F, Cl, Br or I), nitro ($NO_2$), cyano (CN), oxo (=O), $(C_1\text{-}C_6)$alkyl, OH, $CO_2H$, $(C_1\text{-}C_6)$alkoxy, $CO_2$—$(C_1\text{-}C_8)$alkyl and $NR_{28}R_{29}$, notably selected from halo (F, Cl, Br or I), nitro ($NO_2$), cyano (CN), oxo (=O), $(C_1\text{-}C_6)$alkyl, OH, $(C_1\text{-}C_6)$alkoxy and $NR_{28}R_{29}$, in particular selected from halo (F, Cl, Br or I), oxo (=O), $(C_1\text{-}C_6)$alkyl, OH, $(C_1\text{-}C_6)$alkoxy and $NR_{28}R_{29}$.

When $R_{15}$ and $R_{16}$ and/or $R_{20}$ and $R_{21}$ form a heterocycle together with the nitrogen atom which carries them, the heterocycle can be selected from azetidine, pyrrolidine, pyrroline, piperidine, dihydropyridine, tetrahydropyridine, morpholine, thiomorpholine, piperazine, azepane, diazepane, imidadole, imidazoline, pyrrole, pyrazole, and piperidazine. In particular, the heterocycle is selected from pyrrolidine, pyrroline, piperidine, dihydropyridine, tetrahydropyridine, morpholine, piperazine, azepane, and diazepane. The heterocycle can notably be selected from pyrrolidine, piperidine, morpholine, piperazine, azepane, and diazepane. In particular, the heterocycle is selected from pyrrolidine, piperidine, morpholine, and piperazine.

In the above mentioned embodiments for $R_{10}$ to $R_{23}$ and $R_{30}$, the $R_{24}$, $R_{25}$, $R_{26}$, $R_{27}$, $R_{28}$ and $R_{29}$ groups are as defined previously and advantageously are, independently of each other, H or a ($C_1$-$C_6$)alkyl group, or $R_{24}$ and $R_{25}$ and/or $R_{26}$ and $R_{27}$ and/or $R_{28}$ and $R_{29}$ form together, with the nitrogen atom which carries them, a 3- to 7-membered saturated or unsaturated heterocycle optionally comprising one or two heteroatoms chosen from O, N and S in addition to the nitrogen atom, optionally substituted with one or several groups selected from halo (F, Cl, Br or I), oxo (=O) and ($C_1$-$C_6$)alkyl, in particular a 5 or 6-membered saturated heterocycle optionally comprising one heteroatom chosen from O and N in addition to the nitrogen atom, optionally substituted with one or several groups selected from halo (F, Cl, Br or I), oxo (=O) and ($C_1$-$C_6$) alkyl.

When $R_{24}$ and $R_{25}$ and/or $R_{26}$ and $R_{27}$ and/or $R_{28}$ and $R_{29}$ form a heterocycle together with the nitrogen atom which carries them, the heterocycle can be selected from azetidine, pyrrolidine, pyrroline, piperidine, dihydropyridine, tetrahydropyridine, morpholine, thiomorpholine, piperazine, azepane, diazepane, imidadole, imidazoline, pyrrole, pyrazole, and piperidazine. In particular, the heterocycle is selected from pyrrolidine, pyrroline, piperidine, dihydropyridine, tetrahydropyridine, morpholine, piperazine, azepane, and diazepane. The heterocycle can notably be selected from pyrrolidine, piperidine, morpholine, piperazine, azepane, and diazepane. In particular, the heterocycle is selected from pyrrolidine, piperidine, morpholine, and piperazine.

$R_{30}$ can represent in particular H or a ($C_1$-$C_6$)alkyl group.

According to a first embodiment, $R_4$ and $R_6$ do not form together a chain as defined previously. Particularly, $R_4$ and $R_6$ are, independently of one another, selected from H; halo; nitro ($NO_2$); cyano (CN); $R_{10}$; $OR_{11}$; $NR_{15}R_{16}$; $OC(O)R_{19}$; $NR_{22}C(O)R_{23}$; and a 5- to 7-membered saturated or unsaturated heterocycle comprising one or two heteroatoms chosen from O and N, optionally substituted with one or several groups selected from halo, nitro ($NO_2$), cyano (CN), oxo (=O), ($C_1$-$C_6$)alkyl, OH, ($C_1$-$C_6$)alkoxy and $NR_{24}R_{25}$. $R_4$ and $R_6$ will be more particularly selected from H, halo (F, Cl, Br or I), $OR_{11}$ and $NR_{15}R_{16}$; preferably selected from H, halo (F, Cl, Br or I), OH, ($C_1$-$C_6$)alkoxy, $NH_2$, ($C_1$-$C_6$) alkylamino and di($C_1$-$C_6$)alkylamino.

According to a second embodiment, $R_4$ and $R_6$ form together a chain as defined previously, such as a chain of formula —$X_1$-A-$X_2$—, in particular of formula —$(OCH_2CH_2)_nO$—, as defined previously.

The compound according to the present invention can be in particular selected from the compounds C1 to C47 of the examples below and the pharmaceutically acceptable salts and solvates thereof.

The present invention relates also to a compound of formula (I) as defined previously for use as a drug, notably intended for the treatment of cancer.

The present invention concerns also the use of a compound of formula (I) as defined previously for the manufacture of a drug, notably intended for the treatment of cancer.

The present invention concerns also a method for treating cancer comprising the administration to a person in need thereof of an effective amount of a compound of formula (I) as defined previously.

The cancer can be more particularly in this case a colon cancer, breast cancer, kidney cancer, liver cancer, pancreas cancer, prostate cancer, lung cancer, ovarian cancer, head and neck cancer, glioblastoma, neuroblastoma, lymphoma, leukaemia, inflammatory myofibroblastic tumour, myelodysplastic syndrome, or myelofibrosis.

The present invention relates also to a pharmaceutical composition comprising at least one compound of formula (I) as defined previously and at least one pharmaceutically acceptable excipient.

The active principle can be administered in unitary dosage forms, in mixture with conventional pharmaceutical carriers, to animals and humans.

The pharmaceutical compositions according to the present invention are more particularly intended to be administered orally or parenterally (for ex. intravenously), notably to mammals including human beings.

Suitable unit dosage forms for administration comprise the forms for oral administration, such as tablets, gelatin capsules, powders, granules and oral solutions or suspensions.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

A preparation in the form of a syrup or an elixir may contain the active ingredient together with a sweetener, an antiseptic, or also a taste enhancer or a suitable coloring agent.

The water-dispersible powders or granules may contain the active ingredient mixed with dispersing agents or wetting agents, or suspending agents, and with flavor correctors or sweeteners.

For parenteral administration, aqueous suspensions, isotonic saline solutions or sterile and injectable solutions which contain pharmacologically compatible dispersing agents and/or wetting agents are used.

The active principle may also be formulated in the form of microcapsules, optionally with one or more carrier additives.

The compounds of the invention can be used in a pharmaceutical composition at a dose ranging from 0.01 mg to 1000 mg a day, administered in only one dose once a day or in several doses along the day, for example twice a day. The daily administered dose is advantageously comprises between 5 mg and 500 mg, and more advantageously between 10 mg and 200 mg. However, it can be necessary to use doses out of these ranges, which could be noticed by the person skilled in the art.

The pharmaceutical compositions according to the present invention can comprise further at least another active principle, such as an anticancer agent.

The present invention relates also to a pharmaceutical composition comprising:
(i) at least one compound of formula (I) as defined previously, and
(ii) at least another active principle, such as an anticancer agent,
as a combination product for a simultaneous, separate or sequential use.

The present invention relates also to a pharmaceutical composition as defined previously for use in the treatment of cancer.

The present invention concerns also a method for treating cancer comprising the administration to a person in need thereof of an effective amount of a pharmaceutical composition according to the invention.

The present invention relates also to a first process to prepare a compound of formula (I) as defined previously comprising a coupling reaction between:
a compound of the following formula (A):

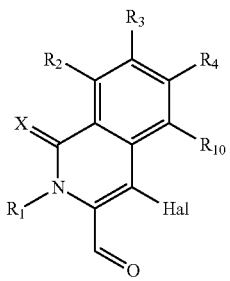

(A)

where X, $R_0$, $R_1$, $R_2$, $R_3$ and $R_4$ are as defined previously, the $R_2$, $R_3$ and $R_4$ groups being optionally in a protected form, and Hal is a halogen atom such as Br, and
a compound of the following formula (B):

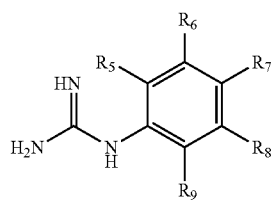

(B)

where $R_5$, $R_6$, $R_7$, $R_8$ and $R_9$ are as defined previously, said $R_5$ to $R_9$ groups being optionally in a protected form,
in the presence of a base,
followed by a deprotection of the $R_2$, $R_3$, $R_4$, $R_5$, $R_6$, $R_7$, $R_8$ and/or $R_9$ groups when they are in a protected form.

The base used in the coupling reaction can be in particular an inorganic base such as $K_2CO_3$, $Cs_2CO_3$ or $Na_2CO_3$.

This reaction can be carried out notably at a temperature comprised between room temperature and 150° C., notably between 50 and 120° C., typically at a temperature of about 90° C.

A solvent, such as ACN (acetonitrile), DMA (dimethylacetamide), DMF (dimethylformamide), acetone or a mixture thereof, can be used. It can be in particular DMF.

In a typical experiment, the compound of formula (A) is reacted with an excess of the compound of formula (B).

In this reaction, any $R_2$ to $R_9$ group which can react in the reaction conditions of the coupling between compounds of formula (A) and (B) has to be protected. Typically a group $NH_2$ will be protected, notably in the form of a $NO_2$ group. In this case, the deprotection step can be performed by reduction of the $NO_2$ group, notably by catalytic hydrogenation using Raney nickel or Pd/C under an hydrogen atmosphere in methanol; in the presence of NaSH in DMSO; or in the presence of iron powder in hot acetic acid. However, any other protecting group can be used, the protecting groups and deprotection conditions being well-known to the one skilled in the art.

The intermediates of formula (A) can be synthesized notably by one of the methods 1A to 3A described below.

Method 1A:

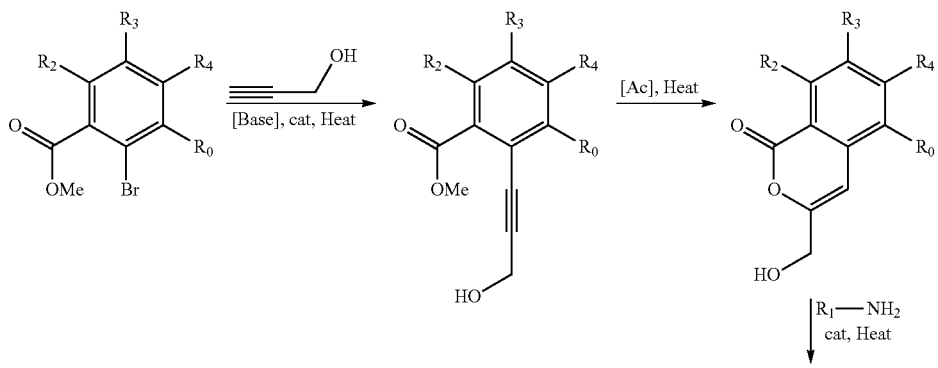

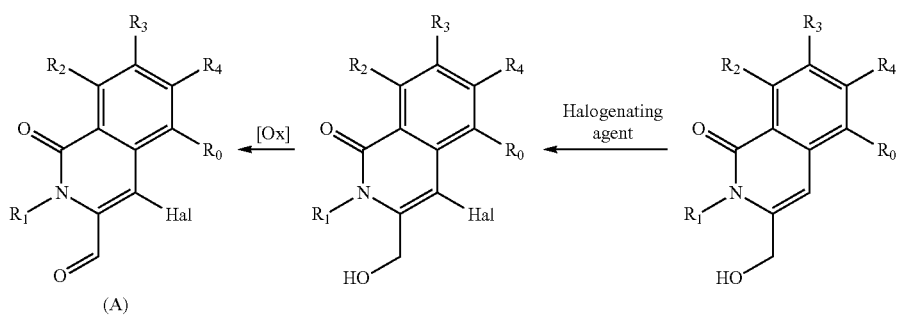

(A)

This method is mainly used when $R_1$ is different from hydrogen and is adapted from the methods described in WO 2012/102985. The main modification concerns the stepwise synthesis of the halolactame derivative from de-halogenated lactone intermediate and de-halogenated lactame, the latter being halogenated in a separate subsequent reaction. Originally, cyclisation and halogenation were reportedly conducted in a single one-step reaction.

The first step is thus classically realized via a Sonogashira reaction as exemplified hereunder.

The second step of cyclisation is typically realized by heating the substituted propargyl alcohol in a high boiling point solvent such as toluene in presence of an acidic catalyst such as TFA (trifluoroacetic acid).

The lactone to lactame conversion is realized by reaction of the lactone with an excess of the corresponding amine in presence of a catalyst such as pTSA (para-toluene sulfonic acid) and under heating.

Halogenation is realized in the presence of conventional halogenating agent. In the case of a bromination reaction, the reaction can be carried out with NBS (N-bromo-succinimide) using conditions compatible with an ionic mechanism.

Finally, the alcohol to aldehyde conversion can be realized using well-known methods of oxidation. The reaction can be carried out notably in the presence of PCC (pyridinium chlorochromate) in hot dichloromethane.

Method 2A:

Alternatively, the intermediate (A) wherein Hal=Br (intermediate (A-i)) can be synthesized as reported on the following scheme.

Method 3A:

When $R_1$ is an hydrogen, the preferred synthesis route is the one depicted in the following scheme.

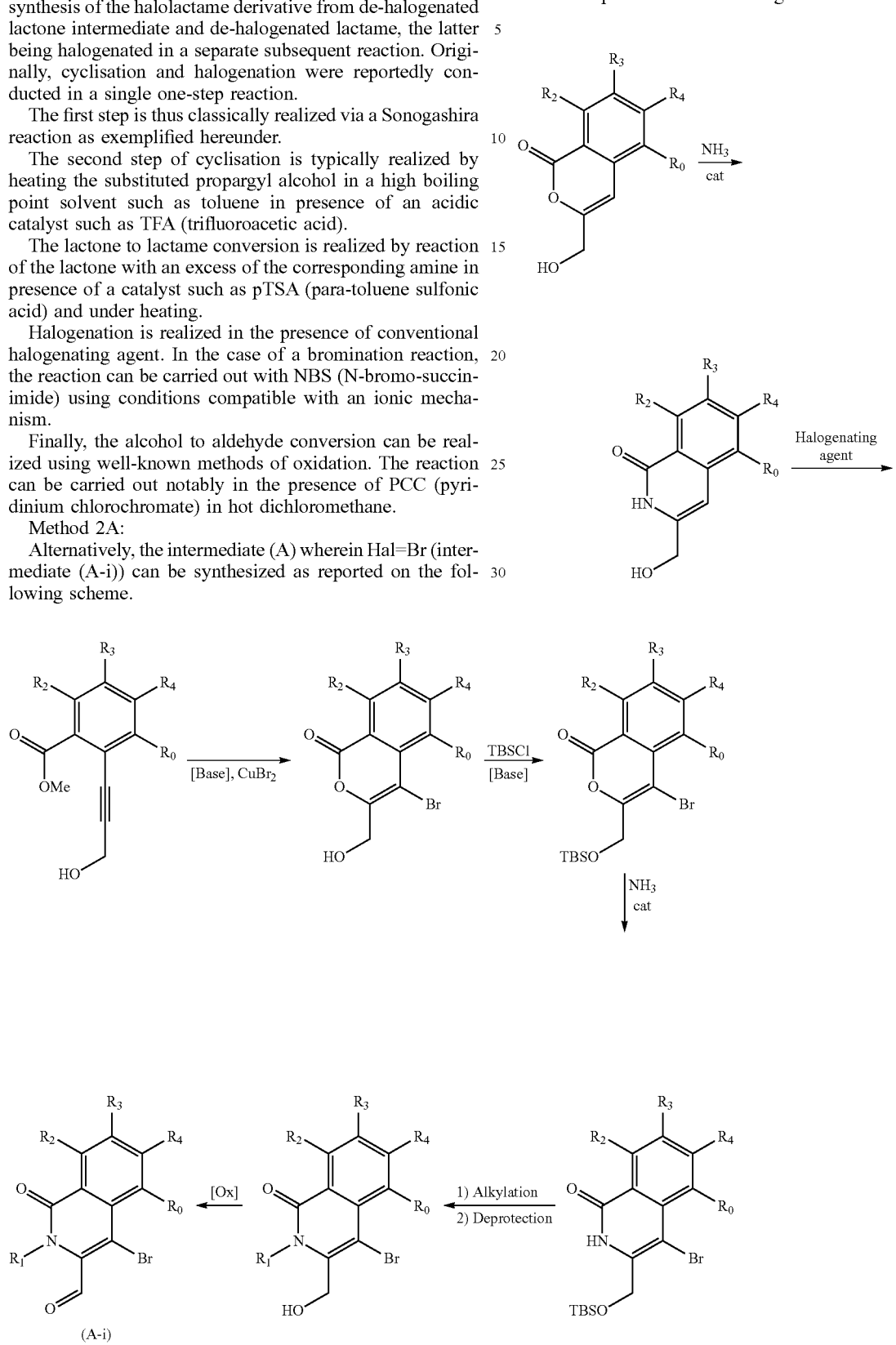

-continued

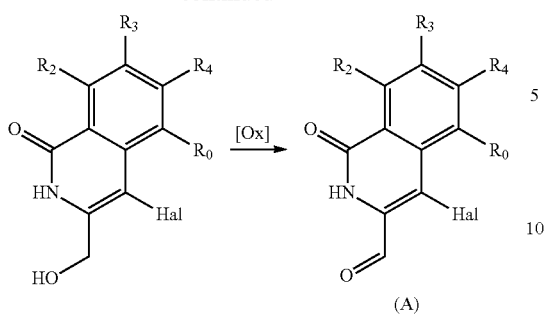

(A)

The lactone to lactame conversion is best conducted using ammonia-saturated THF (tetrahydrofurane) solutions at room temperature in the presence of an acidic catalyst such as pTSA.

Halogenation is realized in the presence of conventional halogenating agent. When Hal=Br, the bromination is preferentially uncatalyzed and conducted with NBS in THF.

The oxidation step is preferentially performed using Dess-Martin periodinane in THF.

The intermediates of formula (B) can be synthesized notably by one of the methods 1B and 2B described below.

Method 1B:

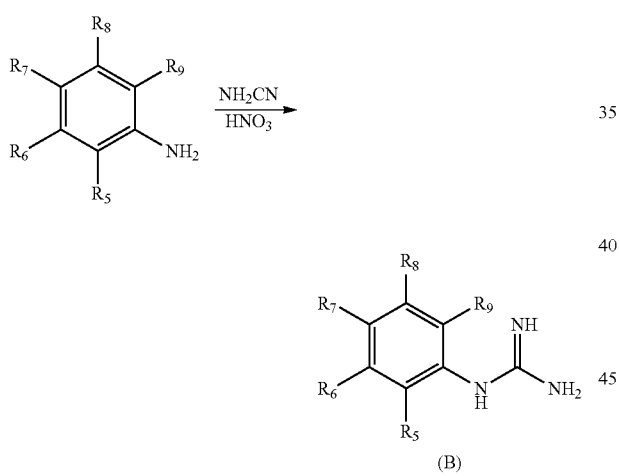

Functionalized anilines are reacted with cyanamide and stœchiometric nitric acid in hot ethanol as described notably in the examples below.

Method 2B:

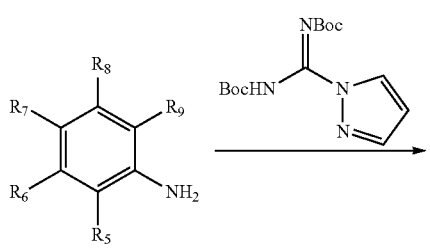

-continued

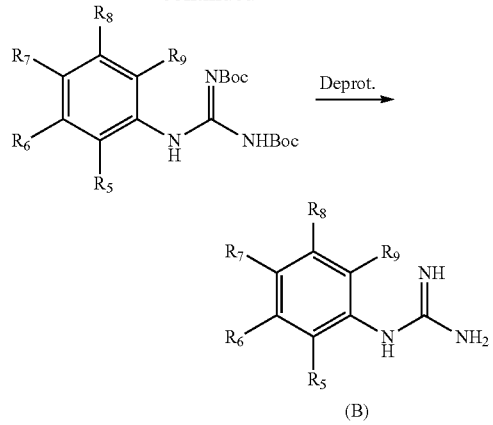

Alternatively guanidines may be synthesized stepwise by reaction of the corresponding anilines with tert-butyl (Z)-(((tert-butoxycarbonyl)imino)(1H-pyrazol-1-yl)methyl)carbamate or another activated amidine reagent, followed by a deprotection step using usual methods such as with trifluoroacetic acid in dichloromethane.

The present invention relates also to a second process to prepare a compound of formula (I) as defined previously, in which $R_4$ and $R_6$ form together a chain of formula —$X_1$-A-$X_2$— as defined above comprising a coupling reaction between:

a compound of the following formula (II):

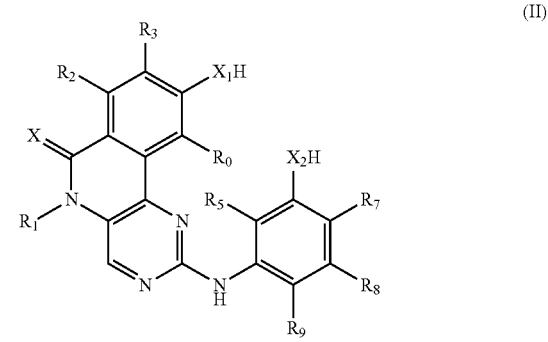

(II)

in which $X_1$, $X_2$, $R_6$, $R_1$, $R_2$, $R_3$, $R_5$, $R_7$, $R_8$ and $R_9$ are as defined previously, and a compound of the following formula (III):

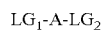  LG$_1$-A-LG$_2$  (III)

in which A is as defined previously and LG$_1$ and LG$_2$ are, independently of each other, a leaving group, in the presence of a base.

The term "leaving group" as used in the present invention refers to a chemical group which can be easily replaced with a nucleophile during a nucleophile substitution reaction, the nucleophile being in the present case an alcohol, i.e. a molecule carrying a group OH, a thiol, i.e. a molecule carrying a group SH, or an amine, i.e. a molecule carrying a group NH. Such a leaving group can be in particular a halogen atom or a sulfonate. The sulfonate is in particular a group —OSO$_2$—R$_{31}$ with R$_{31}$ representing a (C$_1$-C$_6$)alkyl, aryl, aryl-(C$_1$-C$_6$)alkyl or (C$_1$-C$_6$)alkyl-aryl group, the said group being optionally substituted with one or several halogen atoms such as fluorine atoms. The sulfonate can be notably a mesylate (CH$_3$—S(O$_2$)O—), a triflate (CF$_3$—S(O)$_2$O—) or a tosylate (p-Me—C$_6$H$_4$—S(O)$_2$O—).

Advantageously, LG$_1$ and LG$_2$ are, independently of each other, a halogen atom such as Br.

The base used in the coupling reaction can be in particular K$_2$CO$_3$, Cs$_2$CO$_3$ or Na$_2$CO$_3$.

The compound of formula (II) can be prepared notably by the process described previously and compound of formula (III) can be prepared by methods well-known to the person skilled in the art.

Further protection/deprotection steps or functionalization steps can be carried out in the two processes described above, such steps and their reaction conditions being well known to the one skilled in the art.

The compound obtained can be separated from the reaction medium by methods well known to the person skilled in the art, such as by extraction, evaporation of the solvent or by precipitation or crystallisation (followed by filtration).

The compound also can be purified if necessary by methods well known to the person skilled in the art, such as by recrystallisation, by distillation, by chromatography on a column of silica gel or by high performance liquid chromatography (HPLC).

The present invention is illustrated by the following non-limitative examples.

EXAMPLES

1. Synthesis of the Compounds According to the Invention

The following abbreviations are used in the following examples:
Boc=tert-butoxycarbonyl
br=broad
d=doublet
DMF=N,N-dimethylformamide
DMSO=N,N-dimethylsulfoxide
g=gram
h or hr=hour
HPLC=High Performance Liquid Chromatography
Hz=Hertz
J=coupling constant
LCMS=Liquid Chromatography-Mass Spectrometry
m=multiplet
M=Molar
M+H$^+$=parent mass spectrum peak plus H$^+$
mg=milligram
mL=milliliter
mM=millimolar
mmol=millimole
MS=mass spectrum
NBS=N-bromo-succinimide
nM=nanomolar
NMR=Nuclear Magnetic Resonance
PCC=pyridinium chlorochromate
Pd/C=Palladium on charcoal
ppm=part per million
RT=room temperature
s=singlet
sat.=saturated
t=triplet
TBS=tert-butyl-dimethyl-silyl
TEA=triethylamine
TFA=trifluoroacetic acid
TLC=thin layer chromatography
μL=microliter
μM=micromolar

1.1. Synthesis of the Intermediate Compounds

Compound A1: 4-bromo-2-methyl-7-nitro-1-oxo-1,2-dihydroisoquinoline-3-carbaldehyde

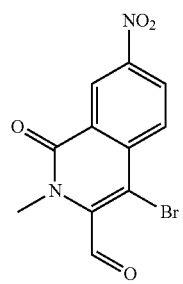 [SMILES: Cn1c(C=O)c(Br)c2ccc([N+](=O)[O-])cc2c1=O]

Step 1: methyl 2-(3-hydroxyprop-1-yn-1-yl)-5-nitrobenzoate

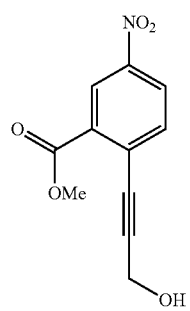 [SMILES: COC(=O)c1cc([N+](=O)[O-])ccc1C#CCO]

To a solution of methyl 2-bromo-5-nitrobenzoate (30 g, 0.1162 mole) in acetonitrile (300 ml) was added prop-2-yn-1-ol (9.72 g, 0.1735 mole) and TEA (23.48 g, 0.2325 mole). The reaction mixture was degassed under argon for 30 minutes. Bis(triphenylphosphine)palladium(II) dichloride (2.4 g, 0.0034 mole) and cupper iodide (0.438 g, 0.0022 mole) were added under argon and heated to 60° C. for 2 hrs. Solvent was evaporated, water (150 ml) was added and the solid was filtered and washed with water (50 ml×3). The solid was dried under vacuum to afford the title compound (25 g, Yield: 92.14%). $^1$H NMR (400 MHz, MeOD): δ 8.72 (s, 1H), 8.39 (dd, 1 J=2.4 Hz, 8.8 Hz, 1H), 7.81 (d, J=8.8 Hz, 1H), 4.50 (s, 2H), 3.99 (s, 3H), 3.33-3.32 (m, 1H)ppm.

Step 2: 3-(hydroxymethyl)-7-nitro-1H-isochromen-1-one

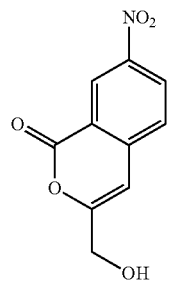 [SMILES: O=c1oc(CO)cc2ccc([N+](=O)[O-])cc12]

To a solution of methyl 2-(3-hydroxyprop-1-yn-1-yl)-5-nitrobenzoate (11.9 g, 0.050 mole) in toluene (120 ml) was added TFA (4 ml) and the mixture was heated overnight to reflux. The solvent was evaporated and the crude material was purified by column chromatography (ethyl acetate: hexane) to get title compound (7.5 g, Yield: 83.32%).

$^1$H NMR (400 MHz, DMSO-d$^6$): δ 8.77 (s, 1H), 8.59 (dd, 1 J=2.4 Hz, 8.8 Hz 1H), 7.93 (d, J=8.8 Hz, 1H), 6.96 (s, 1H), 5.81 (t, J=6 Hz, 1H), 4.35 (d, J=5.6 Hz, 2H) ppm.

Step 3: 3-(hydroxymethyl)-2-methyl-7-nitroisoquinolin-1(2H)-one

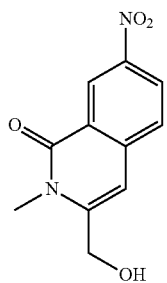 [SMILES: Cn1c(CO)cc2ccc([N+](=O)[O-])cc2c1=O]

A solution of 3-(hydroxymethyl)-7-nitro-1H-isochromen-1-one (8.5 g, 0.038 mole) in 2M solution of methylamine in THF (60 ml) was stirred at room temperature for 2 hrs. p-Toluene sulfonic acid (1 g) was added and the mixture was stirred for 2 hrs at 50° C. The solvent was evaporated under vacuum and water (80 ml) was added. The solid was filtered, washed with water (25 ml×3) and dried under vacuum to get title compound (7.5, Yield: 83.32%).

$^1$H NMR (400 MHz, DMSO-d$^6$): δ 8.92 (s, 1H), 8.43 (d, 1 J=7.2 Hz, 1H), 7.91 (d, J=9.2 Hz, 1H), 6.90 (s, 1H), 5.80 (s, 1H), 4.59 (s, 2H), 3.55 (s, 3H) ppm.

Step 4: 4-bromo-3-(hydroxymethyl)-2-methyl-7-nitroisoquinolin-1(2H)-one

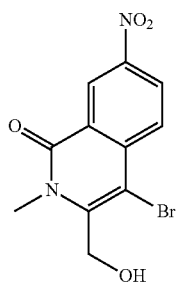 [SMILES: Cn1c(CO)c(Br)c2ccc([N+](=O)[O-])cc2c1=O]

To a solution of 3-(hydroxymethyl)-2-methyl-7-nitroisoquinolin-1(2H)-one (7.4 g, 0.031 mole) in THF (100 ml) at 0° C. was added NBS (5.6 g, 0.0316 mole). The reaction mixture was stirred for 2 hrs at 50° C. p-toluene sulfonic acid (1.5 g) was added and stirred for 2 hrs at 50° C. The solvent was evaporated under vacuum, water (50 ml) was added and the solid was filtered and washed with water (25 ml×3). The solid material was dried under vacuum to get title compound (7.0 g, Yield: 70.76%)

Step 5: Compound A1

To a solution of 4-bromo-3-(hydroxymethyl)-2-methyl-7-nitroisoquinolin-1(2H)-one (7 g, 0.022 mole) in dichloromethane (100 ml) at room temperature was added PCC (7.2 g, 0.033 mole). The reaction mixture was stirred for 3 hrs at 40° C., filtered and the solid was washed with dichloromethane (30 ml×3). The combined filtrates were washed with water (25 ml×3) and brine (25 ml×2). Organic layer was dried over sodium sulfate and evaporated to dryness. The obtained crude material was purified by column chromatography (ethyl acetate:hexane) to get pure title A1 compound (1.5 g, Yield: 21.57%).

$^1$H NMR (400 MHz, DMSO-d$^6$): δ 10.20 (s, 1H), 8.95 (d, J=2.4 Hz, 1H), 8.66 (dd, J=2.4 Hz, 8.8 Hz, 1H), 8.31 (d, J=9.2 Hz, 1H) 3.61 (s, 3H) ppm.

Compound A2: 4-bromo-6-methoxy-2-methyl-7-nitro-1-oxo-1,2-dihydroisoquinoline-3-carbaldehyde

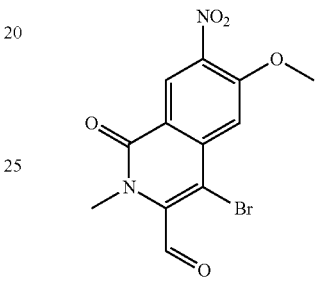

Step 1: methyl 2-bromo-4,5-dinitrobenzoate

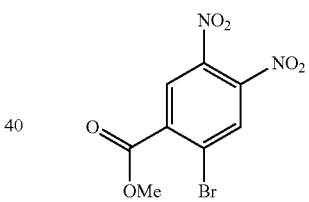

Nitric acid (15 ml) was dropwise added to a solution of methyl 2-bromo-4-nitrobenzoate (10 g, 0.03846 mole) in sulfuric acid (30 ml) at 0° C. The reaction mixture was heated at 50° C. for 1 hr, cooled and poured into ice cold water (300 ml). The solid was filtered, washed with water (50 ml×3) and dried under vacuum to get title compound (10 g, Yield: 85.25%).

$^1$H NMR (400 MHz, DMSO-d$^6$): δ 8.74 (s, 1H), 8.63 (s, 1H), 3.94 (s, 3H) ppm.

Step 2: methyl 2-bromo-4-methoxy-5-nitrobenzoate

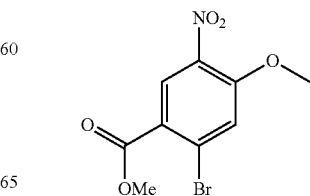

To a solution of methyl 2-bromo-4,5-dinitrobenzoate (10 g, 0.0327 mole) in methanol (80 ml) at 0° C. was dropwise added a solution of KOH (3.68 g, 0.0655 mole) in methanol (20 ml). The reaction mixture was stirred at room temperature for 1 hr. The solvent was evaporated to dryness, water (300 ml) was added and the solid was filtered and washed with water (50 ml×3). The solid was dried under vacuum to get title compound (7 g, Yield: 73.61%).

$^1$H NMR (400 MHz, DMSO-d$^6$): δ 8.39 (s, 1H), 7.76 (s, 1H), 4.04 (s, 3H), 3.86 (s, 3H) ppm.

Step 3: methyl 2-(3-hydroxyprop-1-yn-1-yl)-4-methoxy-5-nitrobenzoate

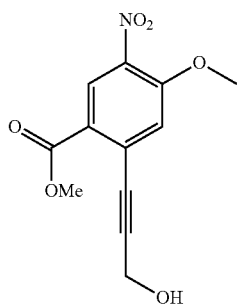 [SMILES: COC(=O)c1cc([N+](=O)[O-])c(OC)cc1C#CCO]

To a solution of methyl 2-bromo-4-methoxy-5-nitrobenzoate (4.7 g, 0.01482 mole) in acetonitrile (50 ml) was added prop-2-yn-1-ol (1.2 g, 0.0224 mole) and TEA (2.9 g, 0.029 mole). The reaction mixture was degassed for 30 minutes and placed under argon. Bis(triphenylphosphine)palladium (II) dichloride (0.31 g, 0.00044 mole) and cupper iodide (0.056 g, 0.00029 mole) were then added and the mixture was heated to 90° C. for 2 hrs. The solvent was evaporated and water (150 ml) was added. The solid was filtered and washed with water (50 ml×3). The solid was dried under vacuum to get title compound (3.7 g, Yield: 94.11%).

$^1$H NMR (400 MHz, CDCl3): δ 8.55 (s, 1H), 7.24 (s, 1H), 4.61 (d, J=4.8 Hz, 2H), 4.04 (s, 3H), 3.94 (s, 3H), 2.22 (s, 1H) ppm.

Step 4: 3-(hydroxymethyl)-6-methoxy-7-nitro-1H-isochromen-1-one

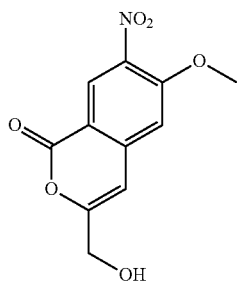 [SMILES: COc1cc2cc(CO)oc(=O)c2cc1[N+](=O)[O-]]

To a solution of methyl 2-(3-hydroxyprop-1-yn-1-yl)-4-methoxy-5-nitrobenzoate (3.7 g, 0.0013 mole) in toluene (50 ml) was added TFA (2 ml) and the mixture was heated to reflux overnight. The solvent was evaporated to dryness and the obtained crude material was purified by column chromatography (ethyl acetate:hexane) to get title compound (3.3 g, Yield: 94.17%).

LCMS: 95.90% ESI-MS (m/z): 249.9 [M−1]$^−$.

Step 5: 3-(hydroxymethyl)-6-methoxy-2-methyl-7-nitroisoquinolin-1(2H)-one

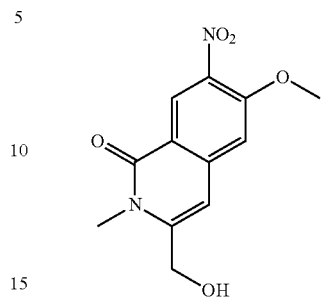

To a stirred solution of 3-(hydroxymethyl)-6-methoxy-7-nitro-1H-isochromen-1-one (3.3 g, 0.015 mole) in a 2M solution of methylamine in THF (30 ml) was added p-toluene sulfonic acid (1 g). The mixture was stirred 2 hrs at 50° C. The solvent was evaporated under dryness, water (50 ml) was added and the thus obtained solid was filtered and washed with water (25 ml×3). The solid was dried under vacuum to get title compound (2.8 g, Yield: 80.66%).

Step 6: 4-bromo-3-(hydroxymethyl)-6-methoxy-2-methyl-7-nitroisoquinolin-1(2H)-one

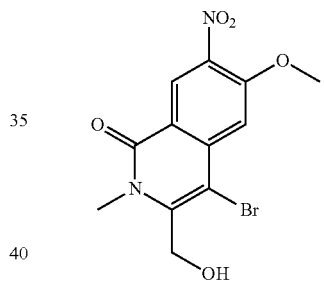

To a solution of 3-(hydroxymethyl)-6-methoxy-2-methyl-7-nitroisoquinolin-1(2H)-one (2.8 g, 0.0106 mole) at 0° C. in THF (30 ml) was added NBS (1.8 g, 0.0106 mole). The reaction mixture was stirred for 2 hrs at 50° C. p-Toluene sulfonic acid (1.5 g) was added and the mixture stirred for 2 hrs at 50° C. The solvent was evaporated under vacuum and water (50 ml) was added. The solid was filtered, washed with water (25 ml×3) and dried under vacuum to get title compound (2.5 g, Yield: 68.76%).

LCMS: 84.33% ESI-MS (m/z): 242.9 [M+1]$^+$.

Step 7: Compound A2

To a solution of 4-bromo-3-(hydroxymethyl)-6-methoxy-2-methyl-7-nitroisoquinolin-1(2H)-one (2.5 g, 0.0025 mole) in THF (100 ml) was added Dess-Martin periodinane (5.9 g, 0.05 mole). The reaction mixture was stirred for 3 hrs at room temperature, filtered and the residue was washed with dichloromethane (30 ml×3). The combined filtrates were washed with aqueous saturated NaHCO$_3$ solution (25 ml×3) and with brine (25 ml×2). The combined organic layers were dried over sodium sulfate and evaporated under vacuum to get crude material. The thus obtained crude material was purified by column chromatography (ethyl acetate:hexane) to get pure title compound (1.7 g, Yield: 68.40%).

¹H NMR (400 MHz, DMSO-d⁶): δ 10.18 (s, 1H), 8.72 (s, 1H), 7.66 (s, 1H), 5.76 (s, 1H), 4.14 (s, 3H), 3.57 (s, 3H) ppm.

Compound A3: 4-bromo-2-methyl-1-oxo-1,2-dihydroisoquinoline-3-carbaldehyde

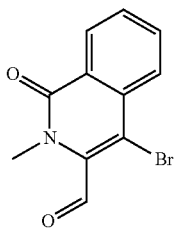

Step 1: methyl 2-(3-hydroxyprop-1-yn-1-yl)benzoate

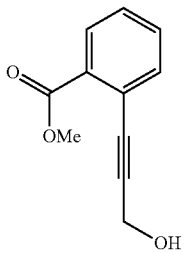 [SMILES: COC(=O)c1ccccc1C#CCO]

To a solution of methyl 2-bromobenzoate (30 g, 0.14 mole) in acetonitrile (300 ml) was added prop-2-yn-1-ol (11.72 g, 0.21 mole) and TEA (58 mL, 0.417 mole). The reaction mixture was degassed under argon for 30 minutes. Bis(triphenylphosphine)palladium(II) dichloride (2.9 g, 0.00417 mole) and copper iodide (0.52 g, 0.00278 mole) were added under argon and heated to 60° C. for 4 hrs. Solvent was evaporated, water (500 ml) was added and the product was extracted with ethyl acetate (300 ml×3). The combined organic layers were washed with brine (300 ml×3), dried over anhydrous sodium sulfate and evaporated to dryness. The obtained crude material was purified by column chromatography (ethyl acetate:hexane) to get pure title compound (10 g, Yield: 37.69%).

¹H NMR (400 MHz, DMSO-d⁶): δ 7.84 (d, J=0.8 Hz, 1H), 7.61-7.55 (m, 2H), 7.50-7.46 (m, 1H), 5.36 (t, J=6, 1H), 4.33 (d, J=6 Hz, 2H), 3.86 (s, 3H) ppm.

Step 2: 4-bromo-3-(hydroxymethyl)-1H-isochromen-1-one

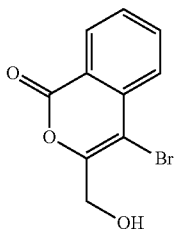 [SMILES: O=c1oc(CO)c(Br)c2ccccc12]

To a stirred solution of methyl 2-(3-hydroxyprop-1-yn-1-yl)benzoate (5 g, 0.0263 mole) in 1,2 dichloroethane (50 ml) was added dicyclohexyl amine (0.56 g, 0.00263 mole) and copper(II) bromide (8.8 g, 0.0394 mole). The reaction mixture was heated to reflux for 3 hrs. The solvent was evaporated to get crude material which was purified by column chromatography (ethyl acetate:hexane) to get title compound (2.5 g, Yield: 37.28%).

¹H NMR (400 MHz, DMSO-d⁶): δ 8.21 (d, J=8 Hz 1H), 8.00 (t, J=7.2 Hz, 1H), 7.85 (d, J=8 Hz 1H) 7.72 (t, J=7.2 Hz, 1H), 5.75 (t, J=6 Hz, 1H), 4.54 (d, J=6 Hz, 2H) ppm.

Step 3: 4-bromo-3-(((tert-butyldimethylsilyl)oxy)methyl)-1H-isochromen-1-one

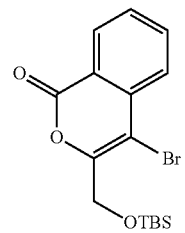 [SMILES: CC(C)(C)[Si](C)(C)OCc1oc(=O)c2ccccc2c1Br]

To a solution of 4-bromo-3-(hydroxymethyl)-1H-isochromen-1-one (1.8 g, 7.06 mmole) in dichloromethane (20 ml) was added TBSCl (1.06 g, 7.06 mmole) and imidazole (0.9 g, 14.12 mmole). The reaction mixture was stirred at room temperature for 2 hrs. Water (200 ml) was added and the product extracted with ethyl acetate (100 ml×3). The organic layer was washed with brine (30 ml×3), dried over anhydrous sodium sulfate and evaporated under vacuum to get pure title compound (2.2 g, Yield: 84.41%).

¹H NMR (400 MHz, CDCl₃): δ 8.33 (d, J=8.4 Hz 1H), 7.89-7.82 (m, 1H), 7.63-7.59 (m, 1H), 4.79 (s, 2H), 0.95 (s, 9H), 0.19 (s, 6H) ppm.

Step 4: 4-bromo-3-(((tert-butyldimethylsilyl)oxy)methyl)isoquinolin-1(2H)-one

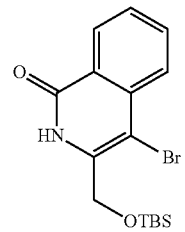 [SMILES: CC(C)(C)[Si](C)(C)OCc1[nH]c(=O)c2ccccc2c1Br]

To a stirred solution of 4-bromo-3-(((tert-butyldimethylsilyl)oxy)methyl)-1H-isochromen-1-one (2.2 g, 5.96 mmole) was added ethanolic ammonia (30 ml). The mixture was stirred for 2 hrs, p-toluene sulfonic acid (250 mg) was then added and the mixture was stirred for 2 hrs at room temperature. The solvent was evaporated to dryness added with 3N HCl solution in ethyl acetate (30 ml). Organic layer was washed with brine solution (20 ml×3) and dried over anhydrous sodium sulfate. Solvent was evaporated under vacuum to get pure title compound (1.5 g, Yield: 68.36%).

$^1$H NMR (400 MHz, CDCl$_3$): δ 9.15 (bs, 1H), 8.44 (d, J=8 Hz, 1H), 7.90 (d, J=8.4 Hz, 1H), 7.77 (t, J=8 Hz, 1H), 7.55 (t, J=7.2 Hz, 1H), 4.79 (s, 2H), 1.00 (s, 9H), 0.22 (s, 6H) ppm.

Step 5: 4-bromo-3-(hydroxymethyl)-2-methylisoquinolin-1(2H)-one

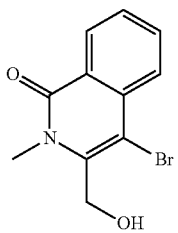

To a solution of 4-bromo-3-(((tert-butyldimethylsilyl)oxy)methyl)isoquinolin-1(2H)-one (1.5 g, 4.07 mmole) in methanol (15 ml) at room temperature was added K$_2$CO$_3$ (1.66 g, 6.52 mmole) and sulfuric acid dimethyl ester (2.57 g, 0.0203 mole). The reaction mixture was stirred for 3 hrs at 60° C. Water (200 ml) was added and the crude product was extracted with ethyl acetate (20 ml×3). Organic layers were combined, washed with brine solutions (20 ml×3), dried over anhydrous sodium sulfate and evaporated under vacuum to get pure title compound (0.9 g, Yield: 82.43%).

Step 6: Compound A3

To a solution of 4-bromo-3-(hydroxymethyl)-2-methylisoquinolin-1(2H)-one (0.9 g, 0.0036 mole) in dichloromethane (30 ml) at room temperature was added Dess-Martin periodinane (2.1 g, 0.0056 mole). The reaction mixture was stirred for 3 hrs at room temperature, filtered and washed with dichloromethane (30 ml×3). The filtrate was washed with saturated NaHCO$_3$ solutions (20 ml×3) and brine (25 ml×2). The combined organic layers were dried over sodium sulfate and evaporated under vacuum to get crude material. The obtained crude material was purified by column chromatography (ethyl acetate:hexane) to get pure title compound (0.8 g, Yield: 89.56%).

$^1$H NMR (400 MHz, DMSO-d$^6$): δ 10.25 (s, 1H), 8.35 (d, J=7.2 Hz, 1H), 8.14 (d, J=8 Hz 1H), 7.98 (t, J=7.2 Hz, 1H), 7.81 (t, J=7.2 Hz, 1H), 3.61 (s, 3H) ppm.

Compound A4: 4-bromo-7-nitro-1-oxo-1,2-dihydroisoquinoline-3-carbaldehyde

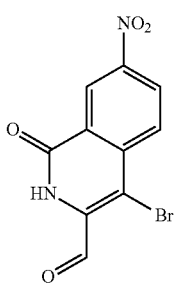 [SMILES: O=Cc1[nH]c(=O)c2cc([N+](=O)[O-])ccc2c1Br]

Step 1: 3-(hydroxymethyl)-7-nitroisoquinolin-1(2H)-one

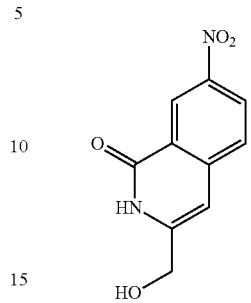

A solution of 3-(hydroxymethyl)-7-nitro-1H-isochromen-1-one (3 g, 0.0135 mole) in 2M ammonia solution in THF (60 ml) was stirred at room temperature for 2 hrs. pT sulfonic acid (1 g) was added and the mixture stirred for 2 hrs at 50° C. The solvent was evaporated under vacuum and water (80 ml) was added. The solid was filtered, washed with water (50 ml×3) and dried under vacuum to get title compound (2.8 g, Yield: 93.75%).

LCMS: 97.41% ESI-MS (m/z): 220.9 [M−1]$^-$.

Step 2: 4-bromo-3-(hydroxymethyl)-7-nitroisoquinolin-1(2H)-one

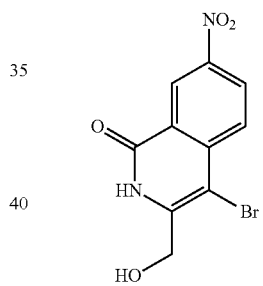

To a solution of 3-(hydroxymethyl)-7-nitroisoquinolin-1(2H)-one (1 g, 0.0044 mole) in THF (10 ml) at 0° C. was added NBS (0.8 g, 0.0044 mole). The reaction mixture was stirred for 1 hr at room temperature. The solvent was evaporated under vacuum and water (50 ml) was added. The solid was filtered, washed with water (25 ml×3) and dried under vacuum to get title compound (0.9 g, Yield: 66.26%).

LCMS: 99.38% ESI-MS (m/z): 296.9 [M−1]$^-$.

Step 3: Compound A4

To a solution of 4-bromo-3-(hydroxymethyl)-7-nitroisoquinolin-1(2H)-one (0.9 g, 3.03 mmole) in THF at room temperature (10 ml) was added Dess-Martin periodinane (2.5 g, 6.1 mmole). The reaction mixture was stirred for 3 hrs at room temperature. The reaction crude was filtered and the solid was washed with ethyl acetate (30 ml×3). Filtrates were combined and washed with saturated NaHCO$_3$ solutions (100 ml×3) and brine (100 ml×2). Combined organic layers were dried over sodium sulfate and evaporated to dryness. Obtained crude material was purified by column chromatography (ethyl acetate:hexane) to get pure title compound (0.5 g, Yield: 55.93%).

¹H NMR (400 MHz, DMSO-d⁶): δ 10.12 (s, 1H), 8.94 (d, J=2.4 Hz, 1H), 8.69 (dd, J=2.4 Hz, 8.8 Hz, 1H), 8.39 (d, J=8.8 Hz, 1H) ppm.

Compound B1: 1-(3-aminophenyl)guanidine

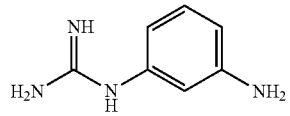

Method 1

Step 1: 1-(3-nitrophenyl)guanidine

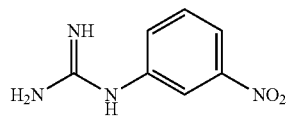 [SMILES: N=C(N)Nc1cccc([N+](=O)[O-])c1]

To a stirred solution of 3-nitroaniline (1 g, 7.24 mmole) in ethanol (10 ml) was added cyanamide (0.35 g, 8.33 mmole) and 70% nitric acid (0.65 ml, 7.24 mmole). The reaction mixture was heated at reflux overnight. The reaction was monitored by TLC (dichloromethane:methanol 9:1), cooled to room temperature and the solvent was concentrated. The reaction mixture was poured into diethyl ether and the resulting precipitate was filtered and dried to afford the title compound as a gray solid (0.9 g, Yield: 69%). LCMS: 98.3% ESI-MS (m/z): 180.91 [M+1]+.

Step 2: Compound B1

To a stirred suspension of Pd/C (400 mg) in methanol (30 ml) was added 1-(3-nitrophenyl)guanidine (4.2 g, 23.3 mmole). Hydrogen gas was purged in for 2 hrs. The reaction mass was filtered through Celite® bed and washed with methanol (3×20 ml). Filtrates were evaporated under vacuum to get title compound (3.5 g, Yield: 99.97%).
LCMS: 84.55% ESI-MS (m/z): 151.10 [M+1]⁺.

Method 2

Step 1: 2-(3-nitrophenyl)-1,3-diBoc-guanidine

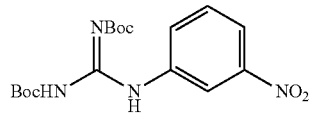

To a stirred solution of 3-nitroaniline (1 g, 7.24 mmole) in DMF (10 ml) was added tert-butyl (Z)-(((tert-butoxycarbonyl)imino) (1H-pyrazol-1-yl)methyl)carbamate (2.25 g, 7.24 mmole). The reaction mixture was stirred overnight at room temperature. Water (15 ml) was added and the solid filtered, washed with water (3×15 ml) and dried under vacuum to get title compound (2.1 g, Yield: 76.25%).

Step 2: 2-(3-aminophenyl)-1,3-diBoc-guanidine

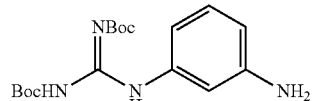

To a suspension of Pd/C (200 mg) in methanol (20 ml) was added 2-(3-nitrophenyl)-1,3-diBoc-guanidine (2.1 g, 5.52 mmole) and hydrogen gas was purged for 2 hrs. The reaction mass was filtered through Celite® bed and washed with methanol (3×20 ml). Filtrate was evaporated under vacuum to get title compound (1.8 g, Yield: 93. 05%).
LCMS: 100% ESI-MS (m/z): 351.23 [M+1]⁺.

Step 3: Compound B1

To a stirred solution of 2-(3-aminophenyl)-1,3-diBoc-guanidine (1.8 g, 5.14 mmole) in dichloromethane (25 ml) was added TFA (5 ml) and the mixture stirred at room temperature overnight. The solvent was evaporated and the residue triturated with ethyl acetate, filtered and dried under vacuum to get TFA salt of title compound which was used as it is (1.8 g, Yield: 100%).

Compound B2:
1-(3-amino-5-methoxyphenyl)guanidine

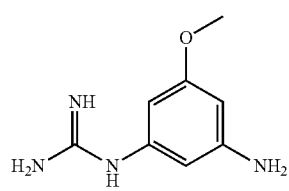

Step 1: 2-(3-nitrophenyl)-1,3-diBoc-guanidine

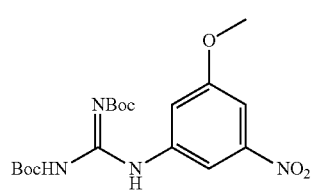

To a stirred solution of 3-methoxy-5-nitroaniline (1 g, 5.95 mmole) in DMF (10 ml) was added tert-butyl (Z)-(((tert-butoxycarbonyl)imino)(1H-pyrazol-1-yl)methyl)carbamate (1.8 g, 5.95 mmole). The reaction mixture was stirred for 48 h at room temperature. Water (15 ml) was added and the solid was filtered and washed with water (3×15 ml). The isolated solid was dried under vacuum to get title compound (500 mg, Yield: 20.49%).

¹H NMR (400 MHz, CDCl3): δ 11.60 (s, 1H), 10.59 (s, 1H), 8.03 (t, J=2 Hz, 1H), 7.80 (t, J=2 Hz, 1H), 7.51 (t, J=2 Hz, 1H), 3.91 (s, 3H), 1.55 (s, 18H) ppm.

Step 2: 1-(3-amino-5-methoxyphenyl)-2,3-diBoc-guanidine

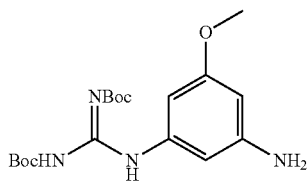

To a suspension of Pd/C (200 mg) in methanol (20 ml) was added 2-(3-nitrophenyl)-1,3-diBoc-guanidine (500 mg, 1.22 mmole). Hydrogen gas was purged in for 2 hrs. The reaction mass was filtered through Celite® bed and washed with methanol (3×20 ml). Filtrates were evaporated under vacuum to get title compound (400 mg, Yield: 86.30%).

$^1$H NMR (400 MHz, CDCl3): δ 11.62 (s, 1H), 10.24 (s, 1H), 6.76 (s, 1H), 6.57 (s, 1H), 6.03 (t, J=2 Hz, 1H), 3.77 (s, 3H), 1.53 (s, 18H) ppm.

Step 3: Compound B2

To a stirred solution of 1-(3-amino-5-methoxyphenyl)-2,3-diBoc-guanidine (400 mg, 1.05 mmole) in dichloromethane (10 ml) was added TFA (3 ml) and the thus obtained mixture was stirred at room temperature overnight. The solvent was evaporated and the solid triturated with ethyl acetate, dried under vacuum to get TFA salt of title compound which was used as it is (300 mg, Yield: 100%).

Compound B3: 1-(5-amino-2-fluorophenyl)guanidine

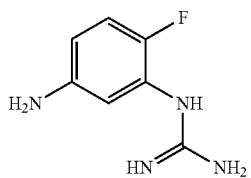 [SMILES: N=C(N)Nc1cc(N)ccc1F]

Step 1: 1-(2-fluoro-5-nitrophenyl)-2,3-diBoc-guanidine

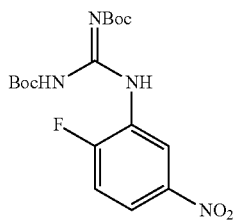

To a stirred solution of 2-fluoro-5-nitroaniline (1 g, 6.41 mmole) in DMF (10 ml) was added tert-butyl (Z)-(((tert-butoxycarbonyl)imino)(1H-pyrazol-1-yl)methyl)carbamate (2 g, 6.41 mmole). The reaction mixture was stirred for 48 hrs at 50° C., water (15 ml) was added and the crude was extracted with ethyl acetate (20 ml×3). Combined organic layers were washed with water (20 ml×3) and brine (20 ml×3) and dried over sodium sulfate. The organic fraction was evaporated under vacuum to get crude material which was purified by trituration with ethyl acetate and hexane to get pure title compound (860 mg, Yield: 33.70%).

LCMS: 85.92% ESI-MS (m/z): 399[M+1]$^+$.

Step 2: 1-(5-amino-2-fluorophenyl)-2,3-diBoc-guanidine

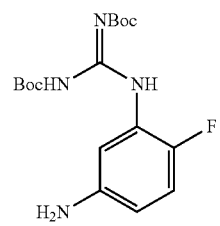

To a stirred suspension of Pd/C (100 mg) in methanol (20 ml) was added 1-(2-fluoro-5-nitrophenyl)-2,3-diBoc-guanidine (860 mg, 2.16 mmole). Hydrogen gas was purged in for 2 hrs. The reaction mass was filtered through Celite® bed and washed with methanol (3×20 ml). Filtrates were evaporated under vacuum to get title compound (750 mg, Yield: 94.33%).

LCMS: 87.59% ESI-MS (m/z): 369.1[M+1]$^+$.

Step 3: Compound B3

To a stirred solution of 1-(5-amino-2-fluorophenyl)-2,3-diBoc-guanidine (750 mg, 2.03 mmole) in dichloromethane (10 ml) was added TFA (2 ml) and the mixture was stirred at room temperature overnight. The solvent was evaporated, the crude mixture was triturated with ethyl acetate, filtered and dried under vacuum to get TFA salt of title compound (500 mg, Yield: Quantitative).

Compound B4: 1-(3-amino-5-fluorophenyl)guanidine

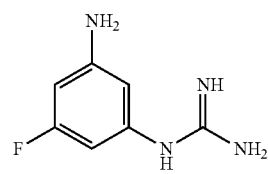 [SMILES: N=C(N)Nc1cc(N)cc(F)c1]

Step 1: 1-(3-fluoro-5-nitrophenyl)-2,3-diBoc-guanidine

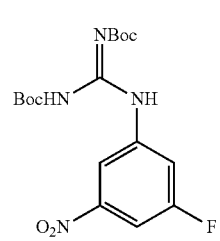

To a solution of 3-fluoro-5-nitroaniline (1 g, 6.41 mmole) in DMF (10 ml) was added tert-butyl (Z)-(((tert-butoxycarbonyl)imino)(1H-pyrazol-1-yl)methyl)carbamate (2 g, 6.41 mmole). The reaction mixture was stirred for 48 hrs at 50° C. Water (15 ml) was added and the crude product was extracted with ethyl acetate (20 ml×3). Combined organic layers were washed with water (20 ml×3) and brine (20 ml×3). Ethyl acetate layers were dried over sodium sulfate and evaporated under vacuum to get crude material. The obtained crude was purified by column chromatography to get pure title compound (590 mg, Yield: 23.13%).

LCMS: 89.45% ESI-MS (m/z): 399.1[M+1]$^+$.

Step 2:
1-(3-amino-5-fluorophenyl)-2,3-diBoc-guanidine

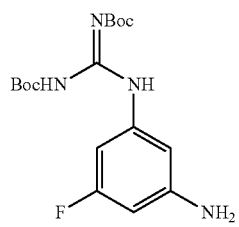

To a suspension of Pd/C (100 mg) in methanol (20 ml) was added 1-(3-fluoro-5-nitrophenyl)-2,3-diBoc-guanidine (590 mg, 1.48 mmole) and hydrogen gas was purged for 2 hrs. The reaction mass was filtered through Celite® bed and washed with methanol (20 ml×3). Filtrate was evaporated under vacuum to get title compound (520 mg, Yield: 95.41%).

LCMS: 93.21% ESI-MS (m/z): 369.3[M+1]$^+$.

Step 3: Compound B4

To a stirred solution of 1-(3-amino-5-fluorophenyl)-2,3-diBoc-guanidine (520 mg, 1.41 mmole) at room temperature in dichloromethane (10 ml) was added TFA (2 ml). The reaction mixture was stirred overnight. The solvent was evaporated and the residue triturated with ethyl acetate, filtered, dried under vacuum to give TFA salt of title compound (500 mg, Yield: Quantitative).

Compound B5:
1-(3-amino-4-fluorophenyl)guanidine

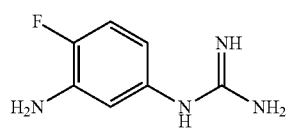 [SMILES: N=C(N)Nc1ccc(F)c(N)c1]

Step 1:
1-(4-fluoro-3-nitrophenyl)-2,3-diBoc-guanidine

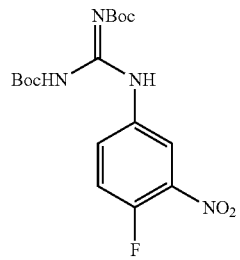

To a solution of 4-fluoro-3-nitroaniline (1 g, 6.41 mmole) in DMF (10 ml) was added tert-butyl (Z)-(((tert-butoxycarbonyl)imino)(1H-pyrazol-1-yl)methyl)carbamate (2 g, 6.41 mmole). The reaction mixture was stirred for 48 hrs at 50° C. Water (15 ml) was added and the expected product was extracted with ethyl acetate (20 ml×3). Combined organic layers were washed with water (20 ml×3) and brine (20 ml×3), dried over sodium sulfate and evaporated to dryness. The obtained crude was purified by trituration with ethyl acetate and hexane to get pure title compound (930 mg, Yield: 36.40%).

LCMS: 88.16% ESI-MS (m/z): 399.2[M+1]$^+$.

Step 2:
1-(3-amino-4-fluorophenyl)-2,3-diBoc-guanidine

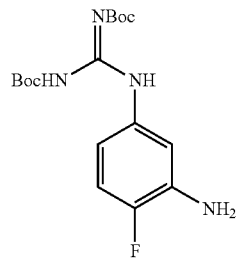

To a stirred suspension of Pd/C (100 mg) in methanol (20 ml) was added 1-(4-fluoro-3-nitrophenyl)-2,3-diBoc-guanidine (930 mg, 2.33 mmole). Hydrogen gas was purged for 2 hrs in the mixture. The reaction mass was filtered through Celite® and washed with methanol (20 ml×3). Filtrates were combined and evaporated to dryness to get title compound (850 mg, Yield: 98.83%).

LCMS: 91.67% ESI-MS (m/z): 369.1[M+1]$^+$.

Step 3: Compound B5

To a stirred solution of 1-(3-amino-4-fluorophenyl)-2,3-diBoc-guanidine (850 mg, 2.30 mmole) in dichloromethane (10 ml) was added TFA (2 ml). The reaction mixture was left to stirring overnight at room temperature. Solvent was concentrated and the precipitate was triturated with ethyl acetate, filtered, dried under vacuum to get the TFA salt of title compound (530 mg, Yield: Quantitative).

Compound B6: 1-(4-cyanophenyl)guanidine

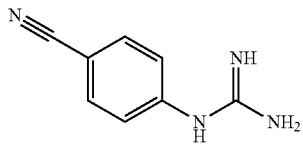 [SMILES: N#Cc1ccc(NC(=N)N)cc1]

Step 1: 1-(4-cyanophenyl)-2,3-diBoc-guanidine

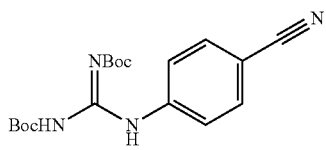

To a stirred solution of 4-aminobenzonitrile (980 mg, 8.29 mmole) in DMF (10 ml) was added tert-butyl (Z)-(((tert-butoxycarbonyl)imino)(1H-pyrazol-1-yl)methyl)carbamate (2.5 g, 8.29 mmole). The reaction mixture was stirred for 48 hrs at 50° C. Water (15 ml) was added and the crude product extracted by ethyl acetate (20 ml×3). Combined organic layers were washed with water (20 ml×3) and brine (20 ml×3), concentrated to dryness, dried over sodium sulfate and concentrated under vacuum to get crude material. The obtained solid was purified by column chromatography (400 mg, Yield: 13.37%).

LCMS: 99.65% ESI-MS (m/z): 361[M+1]$^+$.

Step 2: Compound B6

To a stirred solution of 1-(4-cyanophenyl)-2,3-diBoc-guanidine (400 mg, 1.10 mmole) in dichloromethane (10 ml) was added TFA (2 ml). The reaction mixture was left overnight to stirring at room temperature. The solvent was concentrated to dryness and the solid residue was triturated with ethyl acetate, filtered, dried under vacuum to get the TFA salt of title compound (350 mg, Yield: Quantitative).

Compound B7: 1-(3-cyanophenyl)guanidine

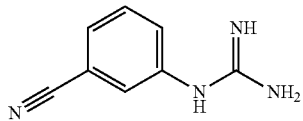 [SMILES: N#Cc1cccc(NC(=N)N)c1]

Step 1: 1-(3-cyanophenyl)-2,3-diBoc-guanidine

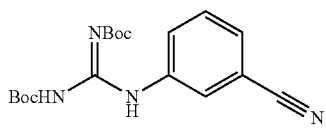

To a stirred solution of 4-aminobenzonitrile (950 mg, 8.04 mmole) in DMF (10 ml) was added tert-butyl (Z)-(((tert-butoxycarbonyl)imino)(1H-pyrazol-1-yl)methyl)carbamate (2.5 g, 8.04 mmole). The reaction mixture was stirred for 36 hrs at 50° C. Water (15 ml) was added and the expected product was extracted with ethyl acetate (20 ml×3). Combined organic layers were washed with water (20 ml×3) and brine (20 ml×3), dried over sodium sulfate and concentrated under vacuum to get crude material. This obtained crude was purified by column chromatography to get pure title compound (980 mg, Yield: 33.91%).

LCMS: 84.39% ESI-MS (m/z): 361.1[M+1]$^+$.

Step 2: Compound B7

To a stirred solution of 1-(3-cyanophenyl)-2,3-diBoc-guanidine (980 mg, 2.72 mmole) in dichloromethane (10 ml) was added TFA (2 ml). The reaction mixture was stirred at room temperature overnight. The solvent was concentrated and the residue was triturated with ethyl acetate, filtered, dried under vacuum to get TFA salt of title compound (820 mg, Yield: Quantitative).

Compound B8: 1-(4-(2-(pyrrolidin-1-yl)ethoxy)phenyl)guanidine

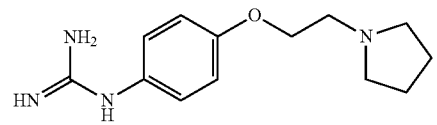 [SMILES: N=C(N)Nc1ccc(OCCN2CCCC2)cc1]

Step 1: 1-(2-(4-nitrophenoxy)ethyl)pyrrolidine

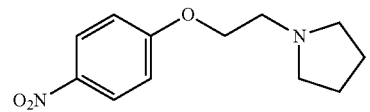

To a stirred solution of 1-fluoro-4-nitrobenzene (10 g, 0.0708 mole) in DMF (40 ml) was added Cs$_2$CO$_3$ (34.6 g, 0.1063 mole). 2-(Pyrrolidin-1-yl)ethan-1-ol (9.79 gm, 0.0850 mole) was added and stirred for 3 hrs at 90° C. Water (40 ml) was added and the expected product was extracted with ethyl acetate (150 ml×3). Combined organic layers were washed with brine (150 ml×3), dried over sodium sulfate and concentrated under vacuum to get crude material. The obtained crude was purified by column chromatography to get pure title compound (10 g, Yield: 59.77%).

LCMS: 99.43% ESI-MS (m/z): 237.05 [M+1]$^+$.

Step 2: 4-(2-(pyrrolidin-1-yl)ethoxy)aniline

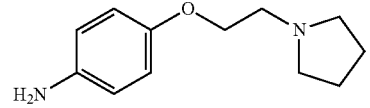 [SMILES: O=[N+]([O-])c1ccc(OCCN2CCCC2)cc1]

To a stirred suspension of Pd/C (220 mg) in methanol at 50° C. was added 1-(2-(4-nitrophenoxy)ethyl) pyrrolidine (2.2 g, 0.0093 mole). Hydrogen gas was flushed into the reaction mixture for 3 hrs. The reaction mass was filtered through Celite® and washed with methanol (3×15 ml). Filtrates were combined and evaporated under vacuum to get title compound (1.8 g, Yield: 93.71%).

LCMS: 97.52% ESI-MS (m/z): 206.87[M+1]$^+$.

Step 3: 1-(4-(2-(pyrrolidin-1-yl)ethoxy)phenyl)-2,3-diBoc-guanidine

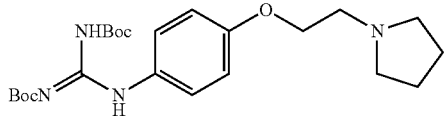

To a stirred solution of 4-(2-(pyrrolidin-1-yl)ethoxy)aniline (4 g, 0.0165 mole) in DMF (20 ml) was added tert-butyl (Z)-(((tert-butoxycarbonyl)imino)(1H-pyrazol-1-yl)methyl)carbamate (5.12 g, 0.0165 mole). The reaction mixture was stirred overnight at RT. Water (50 ml) was added and the thus obtained solid was filtered, washed with water (3×20 ml) and dried under vacuum to get title compound (6.5 g, Yield: 74.73%).

LCMS: 86.41%, ESI-MS (m/z): 449.3[M+1]$^+$.

Step 4: Compound B8

To a solution of 1-(4-(2-(pyrrolidin-1-yl)ethoxy)phenyl)-2,3-diBoc-guanidine (600 mg, 1.33 mmole) in dichloromethane (10 ml) was added TFA (5 ml) and the mixture stirred at room temperature for 2 hrs. The solvent was concentrated and triturated with ethyl acetate. The filtered solid was dried under vacuum to get TFA salt of title compound (500 mg, Yield: quantitative).

Compound B9: 1-(3-methoxy-4-(2-(pyrrolidin-1-yl)ethoxy)phenyl)guanidine

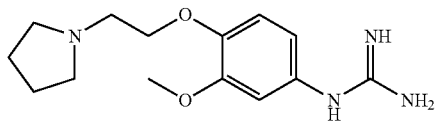 [SMILES: COc1cc(NC(=N)N)ccc1OCCN1CCCC1]

Step 1:
1-(2-(2-methoxy-4-nitrophenoxy)ethyl)pyrrolidine

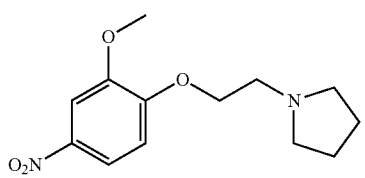

To a stirred solution of 1-fluoro-2-methoxy-4-nitrobenzene (1 g, 5.84 mmole) in DMF (10 ml) was added Cs$_2$CO$_3$ (2.85 g, 8.76 mmole) and 2-(pyrrolidin-1-yl)ethan-1-ol (807 mg, 7.012 mmole). The reaction mixture was stirred for 2 hrs at 90° C. Water (25 ml) was added and the crude product was extracted with ethyl acetate (25 ml×3). Combined organic layers were washed with brine (25 ml×3), dried over sodium sulfate and evaporated under vacuum to get crude material. The obtained crude was purified by flash chromatography to get pure title compound (840 mg, Yield: 54.19%).

LCMS: 99.65% ESI-MS (m/z): 266.97[M+1]$^+$.

Step 2:
3-methoxy-4-(2-(pyrrolidin-1-yl)ethoxy)aniline

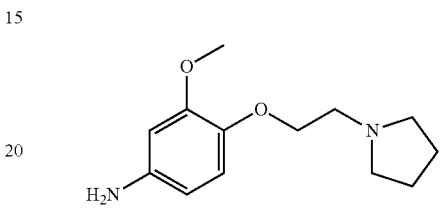

To a stirred suspension of Pd/C (100 mg) in methanol (10 ml) was added 1-(2-(2-methoxy-4-nitrophenoxy)ethyl)pyrrolidine (840 mg, 3.15 mmole). Hydrogen gas was purged within the reaction mixture for 3 hrs at 50° C. The reaction mass was filtered through Celite® and washed with methanol (10 ml×3). Filtrates were combined, evaporated under vacuum to get title compound (710 mg, Yield: 95.30%).

LCMS: 100%, ESI-MS (m/z): 237.08[M+1]$^+$.

Step 3: 1-(3-methoxy-4-(2-(pyrrolidin-1-yl)ethoxy)phenyl)-2,3-diBoc-guanidine

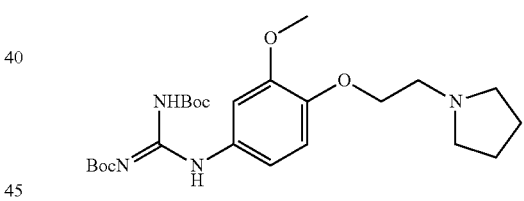

To a stirred solution of 3-methoxy-4-(2-(pyrrolidin-1-yl)ethoxy)aniline (710 mg, 3.008 mmole) in DMF (10 ml) was added tert-butyl (Z)-(((tert-butoxycarbonyl)imino)(1H-pyrazol-1-yl)methyl) carbamate (932 mg, 3.008 mmole). The reaction mixture was stirred overnight at RT. Water (20 ml) was added and the expected product was extracted with ethyl acetate (20 ml×3). Combined organic layers were washed with brine (25 ml×3), dried over sodium sulfate, evaporated under vacuum to get crude material. The obtained crude was purified by flash chromatography to get pure title compound (800 mg, Yield: 55.94%).

LCMS: 98.16%, ESI-MS (m/z): 479.46 [M+1]$^+$.

Step 4: Compound B9

To a stirred solution of 1-(3-methoxy-4-(2-(pyrrolidin-1-yl)ethoxy)phenyl)-2,3-diBoc-guanidine (800 mg, 1.67 mmole) in dichloromethane (20 ml) was added TFA (3 ml). The reaction mixture was left to stirring at room temperature for 2 hrs. The solvent was evaporated and the residue was triturated with ethyl acetate, filtered and dried under vacuum to get TFA salt of title compound (750 mg, Yield: Quantitative).

Compound B10: 1-(2-methoxy-4-(2-(pyrrolidin-1-yl)ethoxy)phenyl)guanidine

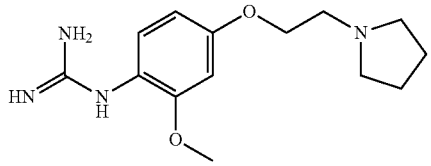 [SMILES: COc1cc(OCCN2CCCC2)ccc1NC(=N)N]

Step 1:
1-(2-(3-methoxy-4-nitrophenoxy)ethyl)pyrrolidine

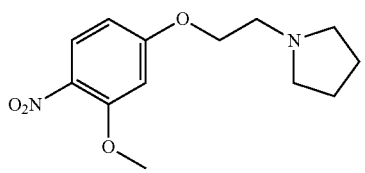 [SMILES: COc1cc(OCCN2CCCC2)ccc1[N+](=O)[O-]]

To a stirred solution of 4-fluoro-2-methoxy-1-nitrobenzene (5 g, 0.0292 mole) in DMF (20 ml) was added $Cs_2CO_3$ (14.3 g, 0.0438 mole) and 2-(pyrrolidin-1-yl)ethan-1-ol (4 gm, 0.0351 mole). The mixture was agitated 2 hrs at 90° C. The solvent was evaporated to dryness and water (50 ml) was added. The thus obtained crude precipitate was extracted with ethyl acetate (50 ml×3). Combined organic layers were washed with brine (50 ml×3), dried over sodium sulfate and evaporated under vacuum. The obtained crude was purified by column chromatograph (3.92 g, Yield: 51%).

LCMS: 99.58% ESI-MS (m/z): 267.48 [M+1]$^+$.

Step 2:
2-methoxy-4-(2-(pyrrolidin-1-yl)ethoxy)aniline

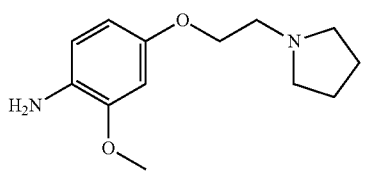

To a stirred suspension of Pd/C (390 mg) in methanol (30 ml) was added 1-(2-(3-methoxy-4-nitrophenoxy)ethyl)pyrrolidine (3.9 g, 0.0146 mole). Hydrogen gas was purged into the reaction mixture for 3 hrs at 50° C. The reaction mass was filtered through Celite® and washed with methanol (15 ml×3). Combined filtrates were evaporated under vacuum to get title compound (3.2 g, Yield: 92.21%).

Step 3: 1-(2-methoxy-4-(2-(pyrrolidin-1-yl)ethoxy)phenyl)-2,3-diBoc-guanidine

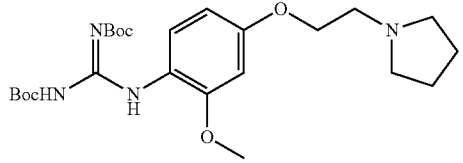

To a solution of 2-methoxy-4-(2-(pyrrolidin-1-yl)ethoxy)aniline (4.4 g, 0.0186 mole) in DMF (30 ml) was added tert-butyl (Z)-(((tert-butoxycarbonyl)imino)(1H-pyrazol-1-yl)methyl) carbamate (5.77 g, 0.0186 mole). The reaction mixture was stirred overnight at RT. Water (100 ml) was then added and the crude product was extracted with ethyl acetate (100 ml×3). Combined organic layers were washed with brine (100 ml×3), dried over sodium sulfate and evaporated under vacuum to get title compound (6 g, Yield: 67.34%).

LCMS: 88.62% ESI-MS (m/z): 479 [M+1]$^+$.

Step 4: Compound B10

To a stirred solution of 1-(2-methoxy-4-(2-(pyrrolidin-1-yl)ethoxy)phenyl)-2,3-diBoc-guanidine (500 mg, 0.0010 mole) in dichloromethane (5 ml) was added TFA (1 ml). The reaction mixture is stirred at room temperature for 2 hrs. The solvent was evaporated and the residue was triturated with ethyl acetate, filtered and dried under vacuum to get TFA salt of title compound (500 g, Yield: Quantitative).

Compound B11:
1-(4-(4-methylpiperazin-1-yl)phenyl)guanidine

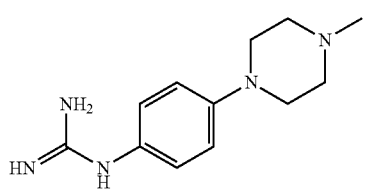 [SMILES: CN1CCN(c2ccc(NC(=N)N)cc2)CC1]

Step 1: 1-(4-(4-methylpiperazin-1-yl)phenyl)-2,3di-Boc-guanidine

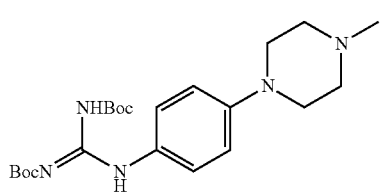

To a stirred solution of 4-(4-methylpiperazin-1-yl)aniline (0.7 g, 3.66 mmole) in DMF (20 ml) was added tert-butyl (Z)-(((tert-butoxycarbonyl)imino)(1H-pyrazol-1-yl)methyl) carbamate (0.90 g, 2.9 mmole). The reaction mixture was stirred overnight at RT. Water (50 ml) was then added and the solid residue was filtered and washed with water (20 ml×3). The solid was dried under vacuum to get title compound (1 g, Yield: 63.03%).

LCMS: 98.31% ESI-MS (m/z): 434.3[M+1]⁺.

Step 2: Compound B11

To a stirred solution of 1-(4-(4-methylpiperazin-1-yl) phenyl)-2,3-diBoc-guanidine (1 g, 0.0022 mole) in dichloromethane (10 ml) was added TFA (5 ml). The mixture is then stirred at room temperature for 2 hrs. Solvent was evaporated and the solid triturated with ethyl acetate, filtered and dried under vacuum to get TFA salt of title compound (700 mg, Yield: quantitative).

Compound B12:
1-(3-(4-methylpiperazin-1-yl)phenyl)guanidine

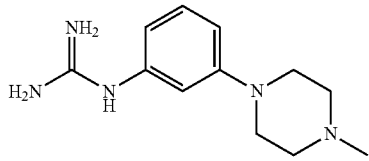 [SMILES: CN1CCN(c2cccc(NC(=N)N)c2)CC1]

Step 1: 1-(3-(4-methylpiperazin-1-yl)phenyl)-2,3-diBoc-guanidine

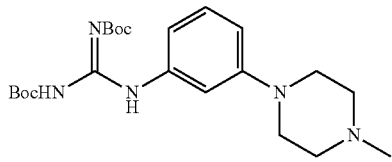

To a stirred solution of 3-(4-methylpiperazin-1-yl)aniline (0.7 g, 3.66 mmole) in DMF (20 ml) was added tert-butyl (Z)-(((tert-butoxycarbonyl)imino)(1H-pyrazol-1-yl)methyl) carbamate (0.90 g, 2.9 mmole). The reaction mixture was stirred overnight at RT. Water (50 ml) was then added and the thus obtained solid was filtered and washed with water (20 ml×3). The solid was dried under vacuum to get title compound (1 g, Yield: 63.03%).

LCMS: 100% ESI-MS (m/z): 434.2[M+1]⁺.

Step 2: Compound B12

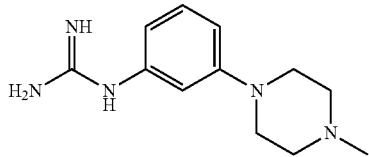 [SMILES: CN1CCN(c2cccc(NC(=N)N)c2)CC1]

To a stirred solution of 1-(3-(4-methylpiperazin-1-yl) phenyl)-2,3-diBoc-guanidine (1 g, 0.22 mmole) in dichloromethane (10 ml) was added TFA (5 ml). The reaction mixture is then stirred at room temperature for 2 hrs. The solvent was then evaporated and the residue was triturated with ethyl acetate, filtered and dried under vacuum to get TFA salt of title compound (700 mg, Yield: quantitative).

1.2. Synthesis of the Compounds of the Invention

Compound C1: 2-((3-aminophenyl)amino)-5-methyl-8-nitropyrimido[5,4-c]isoquinolin-6(5H)-one

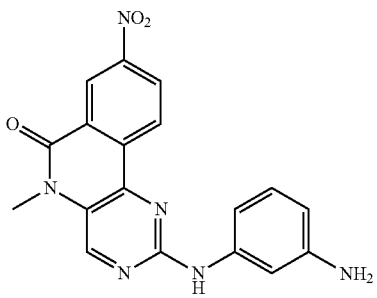

To a stirred solution of 4-bromo-2-methyl-7-nitro-1-oxo-1,2-dihydroisoquinoline-3-carbaldehyde (A1) (1.5 g, 0.0048 mole) in DMF (10 ml) was added 1-(3-aminophenyl)guanidine (B1) (1.09 g, 0.0072 mole). $K_2CO_3$ (1.31 g, 0.0096 mole) was then added and the reaction mixture heated at 90° C. for 2 hrs. Water was added and the solid was filtered, washed with water (25 ml×3), triturated into hexane and dried under vacuum to get crude product (1.35 g, Yield: 77.27%).

LCMS: 77.91% ESI-MS (m/z): 363.12[M+1]⁺

Compound C2: 8-amino-2-((3-aminophenyl)amino)-5-methylpyrimido[5,4-c]isoquinolin-6(5H)-one

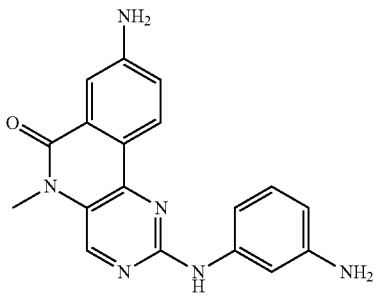 [SMILES: Cn1c(=O)c2cc([N+](=O)[O-])ccc2c2nc(Nc3cccc(N)c3)ncc21]

To a stirred solution of 2-((3-aminophenyl)amino)-5-methyl-8-nitropyrimido[5,4-c]isoquinolin-6(5H)-one (C1) (1.35 gm, 0.0037 mole) in DMSO was added NaSH (1.04 gm, 0.0186 mole). The reaction mixture was heated at 80° C. for 1 hr. Water was then added and the crude product was extracted with ethyl acetate (100 ml×2). Combined organic layers were washed with brine (50 ml×2), dried over sodium sulfate and evaporated under vacuum. The obtained crude material was triturated into diethyl ether and filtered to get pure title compound (642 mg, Yield: 51.85%).

$^1$H NMR (400 MHz, DMSO-d⁶): δ 9.23 (s, 1H), 8.66 (s, 1H), 8.45-8.43 (d, J=8.4 Hz, 1H) 7.47-7.46 (d, J=2.4 Hz, 1H), 7.31 (s, 1H), 7.15-7.13 (dd, J=2.4, 8.8 Hz, 1H), 6.25 (s, 2H), 6.20-6.18 (d, J=7.6 Hz, 1H), 5.02 (s, 2H), 3.68 (s, 3H) ppm.

LCMS: 92.39% ESI-MS (m/z): 333.16 [M+1]⁺. HPLC: 90.38%

Compound C3: 5-methyl-2-((4-(4-methylpiperazin-1-yl)phenyl)amino)-8-nitropyrimido[5,4-c]isoquinolin-6(5H)-one

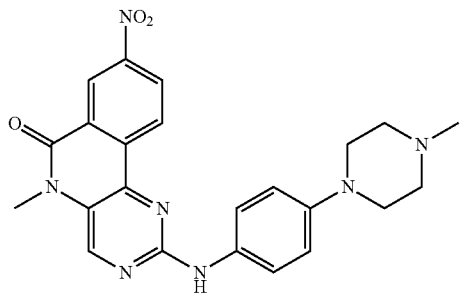

To a stirred solution of 4-bromo-2-methyl-7-nitro-1-oxo-1,2-dihydroisoquinoline-3-carbaldehyde (A1) (150 mg, 0.482 mmole) in DMF (1 ml) was added 1-(4-(4-methylpiperazin-1-yl)phenyl)guanidine (B11) (225 mg, 0.964 mmole). K₂CO₃ (199 mg, 1.4 mmole) was then added and the reaction mixture was heated at 90° C. for 2 hrs. Water (10 ml) was added and the thus obtained solid was filtered, washed with water (10 ml×3) and dried under vacuum to get crude material. This crude was suspended and triturated into hexane, filtered and dried to get title compound (150 mg, Yield: 46.55%).

LCMS: 100% ESI-MS (m/z): 446.15 [M+1]⁺.

Compound C4: 8-amino-5-methyl-2-((4-(4-methylpiperazin-1-yl)phenyl)amino)pyrimido[5,4-c]isoquinolin-6(5H)-one

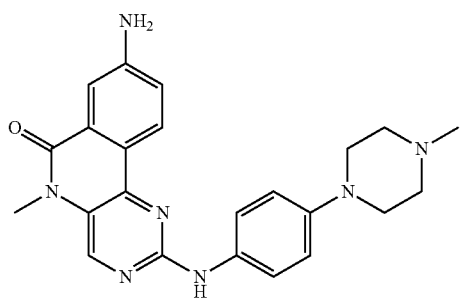

To a stirred solution of 5-methyl-2-((4-(4-methylpiperazin-1-yl)phenyl)amino)-8-nitropyrimido[5,4-c]isoquinolin-6(5H)-one (C3) (150 mg, 0.336 mmole) in acetic acid (5 ml) was added iron powder (94 mg, 1.68 mmole) and the mixture was heated at 90° C. for 2 hrs. Ethyl acetate (10 ml) was then added and the solid was filtered. Filtrates were washed with saturated NaHCO₃ solution (10 ml×3), dried over anhydrous sodium sulfate and evaporated under vacuum to get a crude material which was triturated with hexane and filtered to get title compound (100 mg, Yield: 71.48%).

¹H NMR (400 MHz, DMSO-d⁶): δ 9.29 (s, 1H), 8.65 (s, 1H), 8.38 (d, J=8.8 Hz, 1H), 7.72 (d, J=8.8 Hz, 2H), 7.46 (d, J=2 Hz, 1H), 7.12 (d, J=8.4 Hz, 1H), 6.94 (d, J=8.8 Hz, 2H), 6.26 (s, 2H), 3.67 (s, 3H), 3.08 (s, 4H), 2.47 (s, 4H), 2.23 (s, 3H) ppm.

LCMS: 99.52% ESI-MS (m/z): 416.45 [M+1]⁺. HPLC: 98.99%.

Compound C5: 5-methyl-2-((3-(4-methylpiperazin-1-yl)phenyl)amino)-8-nitropyrimido[5,4-c]isoquinolin-6(5H)-one

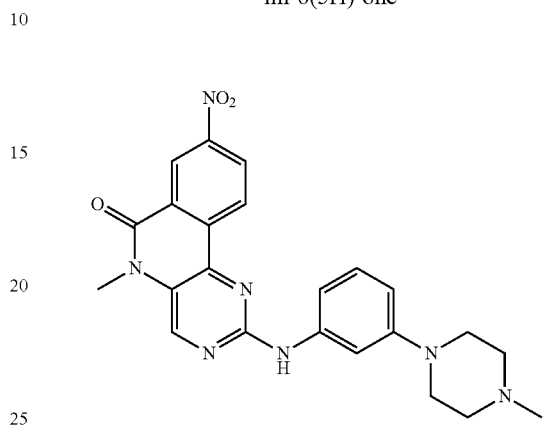

To a stirred solution of 4-bromo-2-methyl-7-nitro-1-oxo-1,2-dihydroisoquinoline-3-carbaldehyde (A1) (150 mg, 0.482 mmole) in DMF (1 ml) was added 1-(3-(4-methylpiperazin-1-yl)phenyl) guanidine (B12) (225 mg, 0.964 mmole). K₂CO₃ (199 mg, 1.4 mmole) was then added and the mixture was heated at 90° C. for 2 hrs. Water (10 ml) was added and the thus obtained solid was filtered, washed with water (10 ml×3), dried under and triturated with hexane to get title compound (150 mg, Yield: 46.55%).

LCMS: 97.72% ESI-MS (m/z): 446.15 [M+1]⁺.

Compound C6: 8-amino-5-methyl-2-((3-(4-methylpiperazin-1-yl)phenyl)amino)pyrimido[5,4-c]isoquinolin-6(5H)-one

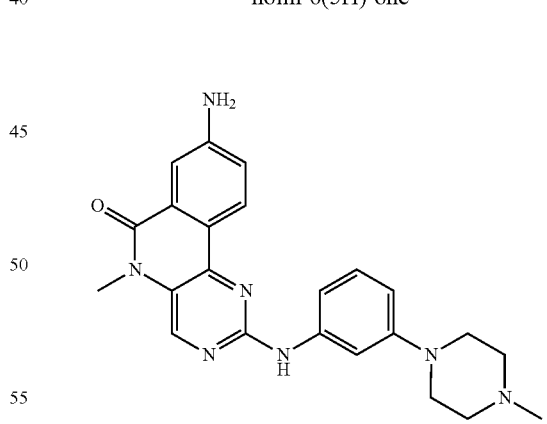

To a stirred solution of 5-methyl-2-((3-(4-methylpiperazin-1-yl)phenyl)amino)-8-nitropyrimido[5,4-c]isoquinolin-6(5H)-one (C5) (150 mg, 0.336 mmole) in acetic acid (5 ml) was added iron powder (94 mg, 1.68 mmole) and the mixture was heated at 90° C. for 2 hrs. Ethyl acetate (10 ml) was added and the solid was filtered. Filtrates were washed with saturated NaHCO₃ solutions (10 ml×3), dried over anhydrous sodium sulfate and evaporated under vacuum to get a crude material which was triturated with hexane and ethyl acetate to get title compound (100 mg, Yield: 71.48%).

¹H NMR (400 MHz, DMSO-d⁶): δ 9.40 (s, 1H), 8.69 (s, 1H), 8.41 (d, J=8.8 Hz, 1H), 7.74 (s, 1H), 7.47 (d, J=2 Hz, 1H), 7.23 (d, J=8 Hz, 1H), 7.16-7.10 (m, 2H), 6.55 (d, J=7.2 Hz, 1H), 6.28 (s, 2H), 3.68 (s, 3H), 3.19 (s, 4H), 2.47 (s, 4H), 2.26 (s, 3H) ppm.

LCMS: 98.13% ESI-MS (m/z): 416.19 [M+1]⁺. HPLC: 97.11%.

Compound C7: 2-((3-aminophenyl)amino)-9-methoxy-5-methyl-8-nitropyrimido[5,4-c]isoquinolin-6(5H)-one

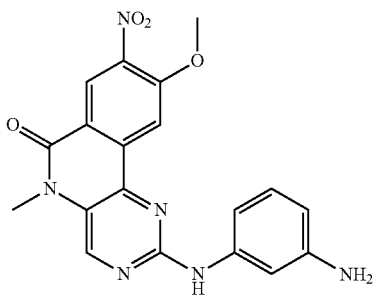

To a stirred solution of 4-bromo-6-methoxy-2-methyl-7-nitro-1-oxo-1,2-dihydroisoquinoline-3-carbaldehyde (A2) (150 mg, 0.439 mmole) in DMF (1 ml) was added 1-(3-aminophenyl)guanidine (B1) (132 mg, 0.879 mmole). K₂CO₃ (182 mg, 1.32 mmole) was added and the mixture was heated at 90° C. for 2 hrs. Water (10 ml) was added and the solid was filtered. The solid was washed with water (10 ml×3), dried under vacuum and triturated with hexane to get title compound (80 mg, Yield: 46.37%).

LCMS: 81.89% ESI-MS (m/z): 393.14 [M+1]⁺.

Compound C8: 8-amino-2-((3-aminophenyl)amino)-9-methoxy-5-methylpyrimido[5,4-c]isoquinolin-6(5H)-one

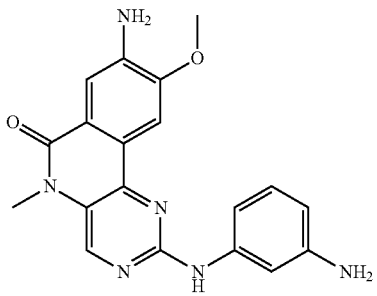 [SMILES: COc1cc2c(cc1[N+](=O)[O-])c(=O)n(C)c1cnc(Nc3cccc(N)c3)nc21]

To a stirred solution of 2-((3-aminophenyl)amino)-9-methoxy-5-methyl-8-nitropyrimido[5,4-c]isoquinolin-6(5H)-one (C7) (80 mg, 0.203 mmole) in acetic acid (5 ml) was added iron powder (56.93 mg, 1.02 mmole) and the mixture was heated at 90° C. for 2 hrs. Ethyl acetate (10 ml) was added and the solid was filtered. Filtrates were combined and washed with saturated NaHCO₃ solution (10 ml×3), dried over anhydrous sodium sulfate and evaporated under vacuum to a get crude material which was purified by preparative HPLC (water:acetonitrile with TFA as a modifier: 15 mg, Yield: 20.30%).

¹H NMR (400 MHz, DMSO-d⁶): δ 9.30 (s, 1H), 8.68 (s, 1H), 8.00 (s, 1H), 7.53 (s, 1H), 7.30 (s, 1H), 6.97-6.91 (q, J=7.6 Hz, 15.6 Hz, 2H), 6.19 (d, J=7.2 Hz, 1H), 5.93 (s, 2H), 4.96 (s, 2H), 4.05 (s, 3H), 3.68 (s, 3H) ppm.

LCMS: 97.80% ESI-MS (m/z): 363.13 [M+1]⁺. HPLC: 97.87%

Compound C9: 9-methoxy-5-methyl-2-((4-(4-methylpiperazin-1-yl)phenyl)amino)-8-nitropyrimido[5,4-c]isoquinolin-6(5H)-one

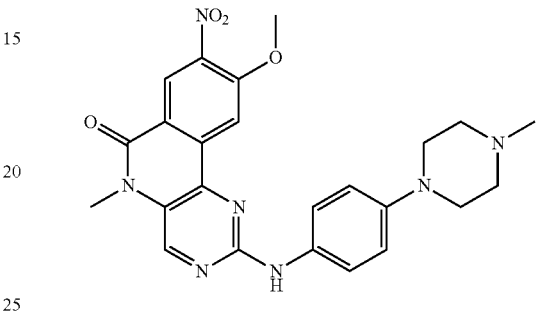

To a stirred solution of 4-bromo-6-methoxy-2-methyl-7-nitro-1-oxo-1,2-dihydroisoquinoline-3-carbaldehyde (A2) (150 mg, 0.439 mmole) in DMF (1 ml) was added 1-(4-(4-methylpiperazin-1-yl)phenyl)guanidine (B11) (205 mg, 0.879 mmole). K₂CO₃ (182 mg, 1.32 mmole) was then added and the mixture heated at 90° C. for 2 hrs. Water (10 ml) was added and the solid was filtered, washed with water (10 ml×3) and dried under vacuum to get a crude material which was triturated with hexane to get title compound (90 mg, Yield: 43.04%).

LCMS: 97.29% ESI-MS (m/z): 476.36 [M+1]⁺.

Compound C10: 8-amino-9-methoxy-5-methyl-2-((4-(4-methylpiperazin-1-yl)phenyl)amino) pyrimido[5,4-c]isoquinolin-6(5H)-one

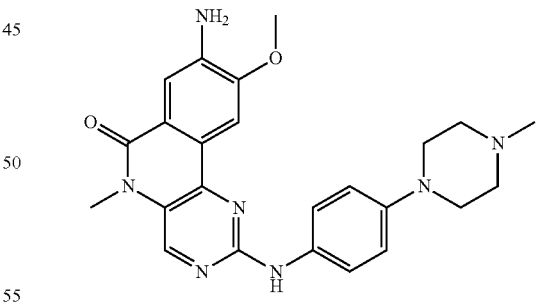

To a stirred solution of 9-methoxy-5-methyl-2-((4-(4-methylpiperazin-1-yl)phenyl)amino)-8-nitropyrimido[5,4-c]isoquinolin-6(5H)-one (C9) (90 mg, 0.189 mmole) in acetic acid (5 ml) was added iron powder (52 mg, 0.946 mmole) and the mixture was heated at 90° C. for 2 hrs. Ethyl acetate (10 ml) was added and the solid was filtered. Combined filtrates were washed with saturated NaHCO₃ solutions (10 ml×3), dried over anhydrous sodium sulfate and evaporated under vacuum to get a crude material which was triturated with hexane and ethyl acetate to get title compound (40 mg, Yield: 47.44%).

¹H NMR (400 MHz, DMSO-d⁶): δ 9.31 (s, 1H), 8.66 (s, 1H), 7.96 (s, 1H), 7.73 (d, J=9.2 Hz, 2H), 7.53 (s, 1H), 6.93 (d, J=8.8 Hz, 2H), 5.91 (s, 2H), 4.03 (s, 3H), 3.67 (s, 3H), 3.07 (t, J=5.2 Hz, 4H), 2.47 (t, J=5.2 Hz, 4H), 2.23 (s, 3H) ppm.

LCMS: 97.56% ESI-MS (m/z): 446.20 [M+1]⁺. HPLC: 98.29%.

Compound C11: 9-methoxy-5-methyl-2-((3-(4-methylpiperazin-1-yl)phenyl)amino)-8-nitropyrimido[5,4-c]isoquinolin-6(5H)-one

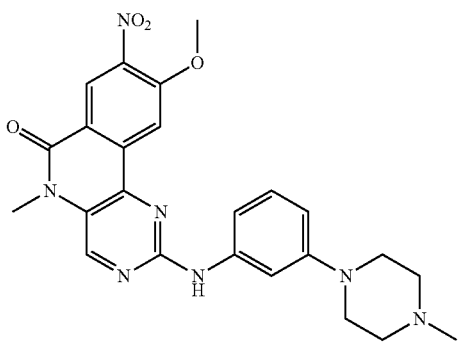 [SMILES: COc1cc2c(cc1[N+](=O)[O-])c(=O)n(C)c1cnc(Nc3cccc(N4CCN(C)CC4)c3)nc21]

To a stirred solution of 4-bromo-6-methoxy-2-methyl-7-nitro-1-oxo-1,2-dihydroisoquinoline-3-carbaldehyde (A2) (150 mg, 0.439 mmole) in DMF (1 ml) was added 1-(3-(4-methylpiperazin-1-yl)phenyl)guanidine (B12) (205 mg, 0.879 mmole). K₂CO₃ (182 mg, 1.32 mmole) was then added and the mixture heated at 90° C. for 2 hrs. Water (10 ml) was added and the solid filtered, washed with water (10 ml×3) and dried under vacuum to get a crude material which was triturated with hexane to get title compound (90 mg, Yield: 43.04%).

LCMS: 96.82% ESI-MS (m/z): 476.31 [M+1]⁺.

Compound C12: 8-amino-9-methoxy-5-methyl-2-((3-(4-methylpiperazin-1-yl)phenyl)amino) pyrimido[5,4-c]isoquinolin-6(5H)-one

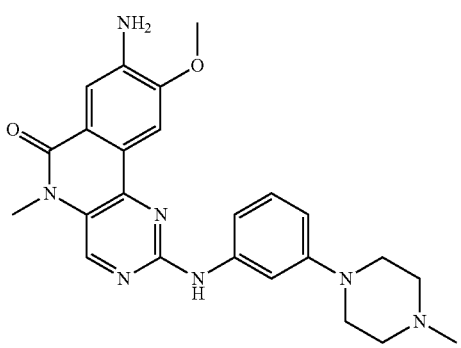

To a stirred solution of 9-methoxy-5-methyl-2-((3-(4-methylpiperazin-1-yl)phenyl)amino)-8-nitropyrimido[5,4-c]isoquinolin-6(5H)-one (C11) (90 mg, 0.189 mmole) in acetic acid (5 ml) was added iron powder (52 mg, 0.946 mmole) and the mixture was heated at 90° C. for 2 hrs. Ethyl acetate (10 ml) was added and the solid was filtered. Combined filtrates were washed with saturated NaHCO₃ solutions (10 ml×3), dried over anhydrous sodium sulfate and evaporated under vacuum to get a crude material which was triturated with hexane and ethyl acetate to get title compound (40 mg, Yield: 47.44%).

¹H NMR (400 MHz, DMSO-d⁶): δ 9.38 (s, 1H), 8.71 (s, 1H), 7.96 (s, 1H), 7.54 (s, 1H), 7.45 (d, J=7.2 Hz, 1H), 7.38 (s, 1H), 7.15 (t, J=8 Hz, 1H), 6.56 (d, J=7.6 Hz, 1H), 5.96 (s, 2H), 4.01 (s, 3H), 3.68 (s, 3H), 3.13 (s, 4H), 2.33 (s, 4H), 2.23 (s, 3H) ppm.

LCMS: 97.01% ESI-MS (m/z): 446.30 [M+1]⁺. HPLC: 95.62%.

Compound C13: 2-((3-amino-5-methoxyphenyl)amino)-5-methyl-8-nitropyrimido[5,4-c]isoquinolin-6(5H)-one

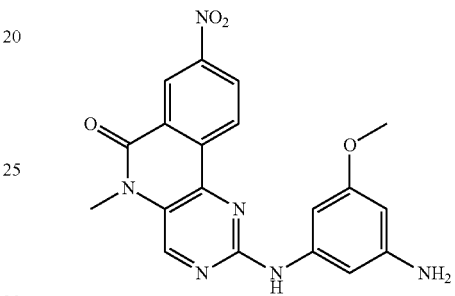

To a stirred solution of 4-bromo-2-methyl-7-nitro-1-oxo-1,2-dihydroisoquinoline-3-carbaldehyde (A1) (150 mg, 0.485 mmole) in DMF (3 ml) was added 1-(3-amino-5-methoxyphenyl)guanidine (B2) (250 mg, 0.481 mmole) and K₂CO₃ (230 mg, 1.66 mmole). The reaction mixture was heated at 90° C. for 2 hrs. Water was then added and the solid was filtered, washed with water (10 ml×3) and dried under vacuum. The crude product was triturated with hexane and dried to get title compound (160 mg, Yield: 84.21%).

LCMS: 89.47% ESI-MS (m/z): 393.24 [M+1]+.

Compound C14: 8-amino-2-((3-amino-5-methoxyphenyl)amino)-5-methylpyrimido[5,4-c]isoquinolin-6(5H)-one

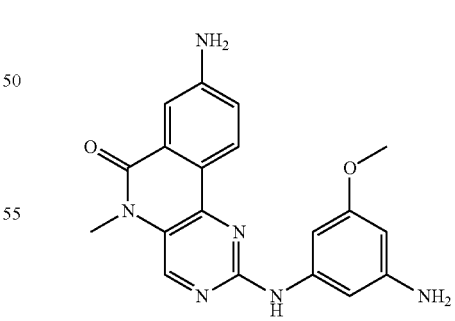

To a stirred solution of 2-((3-amino-5-methoxyphenyl)amino)-5-methyl-8-nitropyrimido[5,4-c]isoquinolin-6(5H)-one (C13) (160 mg, 0.407 mmole) in DMSO (2 ml) was added NaSH (68.4 mg, 1.22 mmole). The reaction mixture was stirred for 2 hrs at RT. Water (10 ml) was then added and the crude mixture was extracted with ethyl acetate (10 ml×2). Combined organic layers were washed with brine (10 ml×2), dried over sodium sulfate and evaporated under vacuum to get a crude material. The obtained crude material was purified by column chromatography (8 mg, Yield: 5.4%).

$^1$H NMR (400 MHz, DMSO-d6): δ 9.22 (s, 1H), 8.66 (s, 1H), 8.43 (d, J=8.4 Hz, 1H), 7.47 (d, J=2.4 Hz, 1H), 7.14 (dd, J=8.4 Hz, 2.4 Hz 1H), 6.80 (d, J=9.6 Hz, 2H) 6.25 (s, 2H), 5.81 (s, 1H), 5.04 (s, 2H), 3.70 (s, 3H), 3.68 (s, 3H) ppm.

LCMS: 98.48% ESI-MS (m/z): 363.33 [M+1]+. HPLC: 98.47%.

Compound C15: 2-((3-amino-5-methoxyphenyl)amino)-9-methoxy-5-methyl-8-nitropyrimido [5,4-c]isoquinolin-6(5H)-one

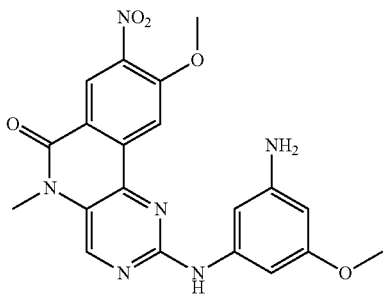 [SMILES: COc1cc(N)cc(Nc2ncc3c(n2)c2cc(OC)c([N+](=O)[O-])cc2c(=O)n3C)c1]

To a stirred solution of 4-bromo-6-methoxy-2-methyl-7-nitro-1-oxo-1,2-dihydroisoquinoline-3-carbaldehyde (A2) (150 mg, 0.439 mole) in DMF (2 ml) was added 1-(3-amino-5-methoxyphenyl)guanidine (B2) (158 mg, 0.879 mmole) and K$_2$CO$_3$ (182 mg, 1.32 mmole). The reaction mixture was heated at 90° C. for 2 hrs. Water (10 ml) was added and the thus obtained solid was filtered, washed with water (10 ml×3) and dried under vacuum to get a crude material which was triturated with hexane to get title compound (80 mg, Yield: 43.07%).

LCMS: 90.25% ESI-MS (m/z): 423.3. [M+1]$^+$.

Compound C16: 8-amino-2-((3-amino-5-methoxyphenyl)amino)-9-methoxy-5-methylpyrimido [5,4-c]isoquinolin-6(5H)-one

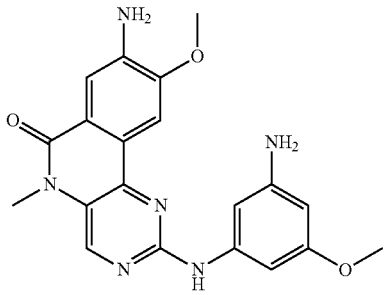

To a stirred solution of 2-((3-amino-5-methoxyphenyl)amino)-9-methoxy-5-methyl-8-nitropyrimido[5,4-c]isoquinolin-6(5H)-one (C15) (80 mg, 0.189 mmole) in DMSO (5 ml) was added NaSH (53.08 mg, 0.94 mmole) and the reaction mixture was stirred at RT for 1 hr. Water (10 ml) was then added and the crude was extracted with ethyl acetate (20 ml×3). Organic layers were washed with brine (20 ml×3), dried over sodium sulfate and evaporated under reduced pressure to get a crude material which was purified by Column chromatography (15 mg, Yield: 20.18%).

$^1$H NMR (400 MHz, DMSO-d$^6$): δ 9.27 (s, 1H), 8.68 (s, 1H), 8.00 (s, 1H), 7.53 (s, 1H), 6.81 (d, J=2 Hz, 2H), 5.93 (s, 2H), 5.83 (d, J=2 Hz, 1H), 4.98 (s, 2H), 4.04 (s, 3H), 3.68 (s, 3H), 3.67 (s, 3H) ppm.

LCMS: 99.32% ESI-MS (m/z): 393.49 [M+1]$^+$. HPLC: 98.91%.

Compound C17: 2-((5-amino-2-fluorophenyl)amino)-5-methyl-8-nitropyrimido[5,4-c]isoquinolin-6(5H)-one

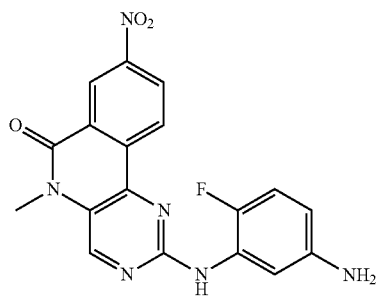

To a stirred solution of 4-bromo-2-methyl-7-nitro-1-oxo-1,2-dihydroisoquinoline-3-carbaldehyde (A1) (120 mg, 0.387 mmole) in DMF (2 ml) was added 1-(5-amino-2-fluorophenyl)guanidine (B3) (77 mg, 0.464 mmole) and K$_2$CO$_3$ (106 mg, 0.774 mmole). The reaction mixture was heated at 90° C. for 2 hrs. Water (5 ml) was then added and the thus obtained solid was filtered, washed with water (10 ml×3) and dried under vacuum. The crude product was triturated with hexane to get title compound (50 mg, Yield: 34.08%).

Compound C18: 8-amino-2-((5-amino-2-fluorophenyl)amino)-5-methylpyrimido[5,4-c]isoquinolin-6(5H)-one

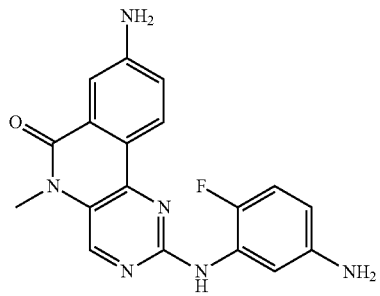 [SMILES: Cn1c(=O)c2cc([N+](=O)[O-])ccc2c2nc(Nc3cc(N)ccc3F)ncc21]

To a stirred solution of 2-((5-amino-2-fluorophenyl)amino)-5-methyl-8-nitropyrimido[5,4-c]isoquinolin-6(5H)-one (C17) (50 mg, 0.131 mmole) in DMSO (1 ml) was added NaSH (36 mg, 0.657 mmole). The reaction mixture was stirred for 1 hr. Water (2 ml) was added and the crude product was extracted with ethyl acetate (10 ml×2). Combined organic layers were washed with brine (10 ml×2), dried over sodium sulfate and evaporated under vacuum to get the crude material which was purified by column chromatography (12 mg, Yield: 26.05%).

¹H NMR (400 MHz, DMSO-d6): δ 8.63 (s, 1H), 8.51 (s, 1H), 8.35 (d, J=8.8 Hz, 1H), 7.45 (d, J=2.4 Hz, 1H), 7.28 (dd, J=8.4 Hz, 2.4 Hz 1H), 7.09 (dd, J=8.4 Hz, 2.4 HZ, 1H) 6.91-6.83 (m, 1H), 6.27 (s, 2H), 4.99 (s, 2H), 3.67 (s, 3H) ppm.

LCMS: 97.26% ESI-MS (m/z): 351.33 [M+1]+. HPLC: 97.01%

Compound C19: 2-((3-amino-5-fluorophenyl)amino)-5-methyl-8-nitropyrimido[5,4-c]isoquinolin-6(5H)-one

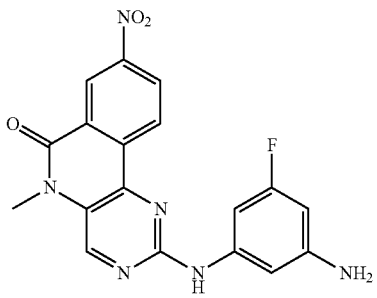 [SMILES: Cn1c(=O)c2cc([N+](=O)[O-])ccc2c2nc(Nc3cc(N)cc(F)c3)ncc21]

To a stirred solution of 4-bromo-2-methyl-7-nitro-1-oxo-1,2-dihydroisoquinoline-3-carbaldehyde (A1) (100 mg, 0.322 mmole) in DMF (2 ml) was added 1-(3-amino-5-fluorophenyl)guanidine (B4) (77 mg, 0.387 mole) and K₂CO₃ (88 mg, 0.645 mmole). The reaction mixture was heated at 90° C. for 2 hrs, water (3 ml) was added and the thus obtained precipitate was filtered. The solid was washed with water (10 ml×3), dried under vacuum and triturated with hexane (80 mg, Yield: 65.43%).

Compound C20: 8-amino-2-((3-amino-5-fluorophenyl)amino)-5-methylpyrimido[5,4-c]isoquinolin-6(5H)-one

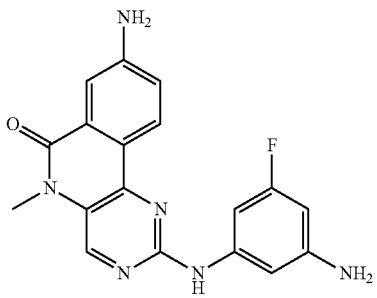

To a stirred solution of 2-((3-amino-5-fluorophenyl)amino)-5-methyl-8-nitropyrimido[5,4-c]isoquinolin-6(5H)-one (C19) (80 mg, 0.21 mmole) in DMSO (1 ml) was added NaSH (59 mg, 1.05 mmole). The reaction mixture was stirred for 1 hr. Water was added and the crude mixture was extracted with ethyl acetate (20 ml×2). Combined organic layers were washed with brine (20 ml×2), dried over sodium sulfate and evaporated under vacuum to get a crude material which was purified by column chromatography (12 mg, Yield: 26.05%).

1H NMR (400 MHz, DMSO-d6): δ 9.47 (s, 1H) 8.69 (s, 1H), 8.40 (d, J=8.4 Hz, 1H), 7.47 (d, J=2.4 Hz, 1H), 7.14 (dd, J=8.4 Hz, 2.4 Hz 1H), 6.97-6.93 (m, 2H), 6.29 (s, 2H), 5.95 (d, J=11.2 Hz, 1H), 5.37 (s, 2H), 3.68 (s, 3H) ppm.

LCMS: 99.42% ESI-MS (m/z): 351.07 [M+1]+. HPLC: 98.85%.

Compound C21: 2-((3-amino-4-fluorophenyl)amino)-5-methyl-8-nitropyrimido[5,4-c]isoquinolin-6(5H)-one

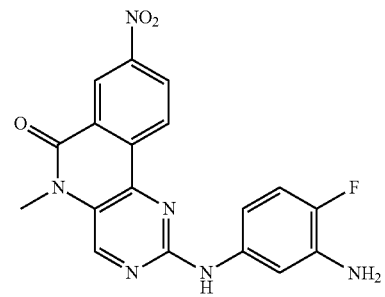 [SMILES: Cn1c(=O)c2cc([N+](=O)[O-])ccc2c2nc(Nc3ccc(F)c(N)c3)ncc21]

To a stirred solution of 4-bromo-2-methyl-7-nitro-1-oxo-1,2-dihydroisoquinoline-3-carbaldehyde (A1) (80 mg, 0.258 mmole) in DMF (1 ml) was added 1-(3-amino-4-fluorophenyl)guanidine (B5) (52 mg, 0.309 mmole) and K₂CO₃ (71.2 mg, 0.516 mmole). The mixture was heated at 90° C. for 2 hrs. Water (5 ml) was added and the thus obtained solid was filtered, washed with water (10 ml×3) and dried under vacuum. The crude product was triturated with hexane to get title compound (75 mg, Yield: 76.53%).

Compound C22: 8-amino-2-((3-amino-4-fluorophenyl)amino)-5-methylpyrimido[5,4-c]isoquinolin-6(5H)-one

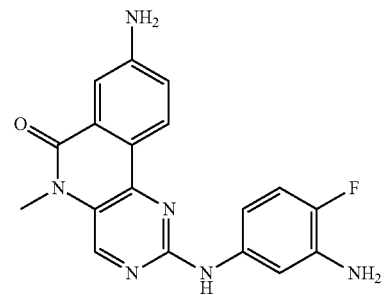 [SMILES: Cn1c(=O)c2cc(N)ccc2c2nc(Nc3ccc(F)c(N)c3)ncc21]

To a stirred solution of 2-((3-amino-4-fluorophenyl)amino)-5-methyl-8-nitropyrimido[5,4-c]isoquinolin-6(5H)-one (C21) (75 mg, 0.197 mmole) in DMSO (1 ml) was added NaSH (55.26 mg, 0.986 mmole). The reaction mixture was stirred for 1 hr. Water (3 ml) was added and the crude product was extracted with ethyl acetate (20 ml×3). Combined organic layers were washed with brine (20 ml×3), dried over sodium sulfate and evaporated under vacuum to get a crude material which was triturated with ethyl acetate and hexane to get the pure expected compound (35 mg, Yield: 50.72%).

¹H NMR (400 MHz, DMSO-d6): δ 9.29 (s, 1H), 8.65 (s, 1H), 8.43 (d, J=8.4 Hz, 1H), 7.47 (d, J=2.4 Hz, 1H), 7.38

(dd, J=8 Hz, 2.4 Hz 1H), 7.13 (dd, J=8.4 Hz, 2.4 HZ, 1H) 6.96-6.89 (m, 2H), 6.26 (s, 2H), 5.11 (s, 2H), 3.69 (s, 3H) ppm.

LCMS: 91.06% ESI-MS (m/z): 351.13 [M+1]+. HPLC: 91.33%.

Compound C23: 2-((5-amino-2-fluorophenyl)amino)-9-methoxy-5-methyl-8-nitropyrimido[5,4-c]isoquinolin-6(5H)-one

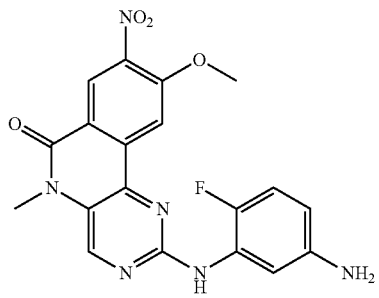 [SMILES: COc1cc2c(cc1[N+](=O)[O-])c(=O)n(C)c1cnc(Nc3cc(N)ccc3F)nc21]

To a stirred solution of 4-bromo-6-methoxy-2-methyl-7-nitro-1-oxo-1,2-dihydroisoquinoline-3-carbaldehyde (A2) (150 mg, 0.439 mmole) in DMF (1 ml) was added 1-(5-amino-2-fluorophenyl)guanidine (B3) (147 mg, 0.879 mmole) and K$_2$CO$_3$ (182 mg, 1.32 mmole). The mixture was heated at 90° C. for 2 hrs. Water (10 ml) was added and the solid was filtered, washed with water (10 ml×3), dried under vacuum to get a crude material which was triturated with hexane to get the expected compound (80 mg, Yield: 46.37%).

Compound C24: 8-amino-2-((5-amino-2-fluorophenyl)amino)-9-methoxy-5-methylpyrimido [5,4-c]isoquinolin-6(5H)-one

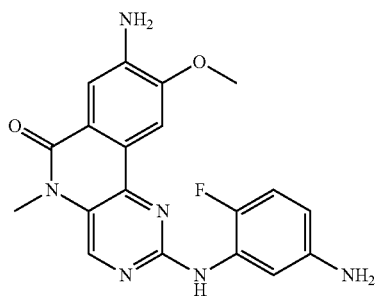

To a stirred solution of 2-((5-amino-2-fluorophenyl)amino)-9-methoxy-5-methyl-8-nitropyrimido[5,4-c]isoquinolin-6(5H)-one (C23) (80 mg, 0.194 mmole) in DMSO (5 ml) was added NaSH (56.93 mg, 1.02 mmole) and the mixture stirred at room temperature for 1 hr. Water (20 ml) was then added and the crude product was extracted with ethyl acetate (20 ml×3). Combined organic layers were washed with brine (20 ml×3), dried over sodium sulfate and evaporated under reduced pressure to get a crude material which was purified by column chromatography to get the expected compound (15 mg, Yield: 20.30%).

$^1$H NMR (400 MHz, DMSO-d$^6$): δ 8.66 (d, J=9.6 Hz, 2H), 7.95 (s, 1H), 7.52 (s, 1H), 7.40 (dd, J=2.8 Hz, 7.2 Hz, 1H), 6.87 (dd, J=8.8 Hz, 11.2 Hz, 1H), 6.26-6.22 (m, 1H), 5.93 (s, 2H), 4.93 (s, 2H), 4.01 (s, 3H), 3.67 (s, 3H) ppm.

LCMS: 97.25% ESI-MS (m/z): 381.28 [M+1]$^+$. HPLC: 97.19%.

Compound C25: 2-((3-amino-5-fluorophenyl)amino)-9-methoxy-5-methyl-8-nitropyrimido[5,4-c]isoquinolin-6(5H)-one

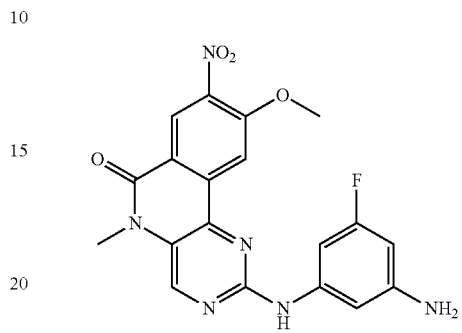

To a stirred solution of 4-bromo-6-methoxy-2-methyl-7-nitro-1-oxo-1,2-dihydroisoquinoline-3-carbaldehyde (A2) (150 mg, 0.439 mmole) in DMF (1 ml) was added 1-(3-amino-5-fluorophenyl)guanidine (B4) (147 mg, 0.879 mmole) and K$_2$CO$_3$ (182 mg, 1.32 mmole). The mixture was heated at 90° C. for 2 hrs, water (10 ml) was added and the thus obtained solid was filtered, washed with water (10 ml×3) and dried under vacuum to get a crude material which was triturated with hexane to get the expected compound (80 mg, Yield: 46.37%).

LCMS: 88.18% ESI-MS (m/z): 411.15 [M+1]$^+$.

Compound C26: 8-amino-2-((3-amino-5-fluorophenyl)amino)-9-methoxy-5-methylpyrimido [5,4-c]isoquinolin-6(5H)-one

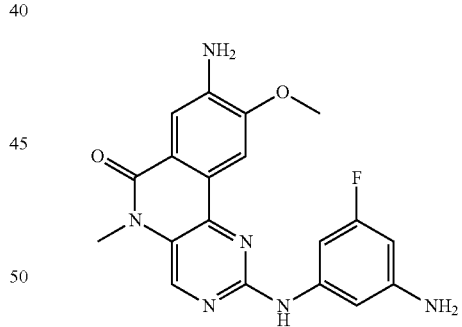

To a stirred solution of 2-((3-amino-5-fluorophenyl)amino)-9-methoxy-5-methyl-8-nitropyrimido[5,4-c]isoquinolin-6(5H)-one (C25) (80 mg, 0.194 mmole) in DMSO (5 ml) was added NaSH (56.93 mg, 1.02 mmole) and the mixture was stirred at RT for 1 hr. Water (10 ml) was then added and the crude product was extracted with ethyl acetate (20 ml×3). Combined organic layers were washed with brine (20 ml×3), dried over sodium sulfate and concentrated under reduced pressure to get a crude material which was purified by flash chromatography (30 mg, Yield: 40.60%).

$^1$H NMR (400 MHz, DMSO-d$^6$): δ 9.53 (s, 1H), 8.71 (s, 1H), 7.98 (s, 1H), 7.53 (s, 1H), 7.12 (d, J=12 Hz, 1H), 6.88 (s, 1H), 5.96 (s, 2H), 5.30 (s, 2H), 4.04 (s, 3H), 3.68 (s, 3H) ppm.

LCMS: 98.58% ESI-MS (m/z): 381.19 [M+1]+. HPLC: 95.92%.

Compound C27: 2-((3-amino-4-fluorophenyl)amino)-9-methoxy-5-methyl-8-nitropyrimido[5,4-c]isoquinolin-6(5H)-one

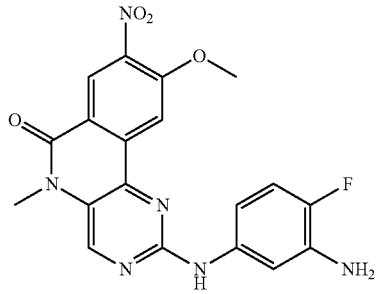 [SMILES: COc1cc2c(cc1[N+](=O)[O-])c(=O)n(C)c1cnc(Nc3ccc(F)c(N)c3)nc21]

To a stirred solution of 4-bromo-6-methoxy-2-methyl-7-nitro-1-oxo-1,2-dihydroisoquinoline-3-carbaldehyde (A2) (150 mg, 0.439 mmole) in DMF (1 ml) was added 1-(3-amino-4-fluorophenyl)guanidine (B5) (147 mg, 0.879 mmole) and K₂CO₃ (182 mg, 1.32 mmole). The reaction mixture was heated at 90° C. for 2 hrs. Water (10 ml) was then added and the solid was filtered, washed with water (10 ml×3) and dried under vacuum. The crude material was triturated with hexane to get the expected compound (80 mg, Yield: 46.37%).

Compound C28: 8-amino-2-((3-amino-4-fluorophenyl)amino)-9-methoxy-5-methylpyrimido[5,4-c]isoquinolin-6(5H)-one

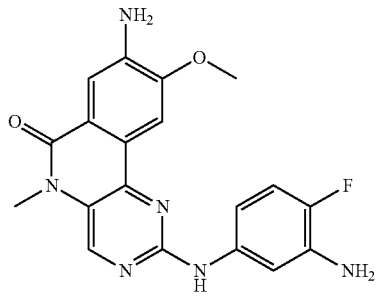

To a stirred solution of 2-((3-amino-4-fluorophenyl)amino)-9-methoxy-5-methyl-8-nitropyrimido[5,4-c]isoquinolin-6(5H)-one (C27) (80 mg, 0.194 mmole) in DMSO (5 ml) was added NaSH (56.93 mg, 1.02 mmole) and the reaction mixture was stirred at RT for 1 hr. Water (20 ml) was then added and the thus obtained crude product was extracted with ethyl acetate (20 ml×3). Combined organic layers were washed with brine (20 ml×3), dried over sodium sulfate and evaporated under reduced pressure to get crude material which was purified by flash chromatography (15 mg, Yield: 20.30%).

$^1$H NMR (400 MHz, DMSO-d$^6$): δ 9.34 (s, 1H), 8.67 (s, 1H), 7.99 (s, 1H), 7.53 (s, 1H), 7.44 (d, J=7.6 Hz, 1H), 6.93-6.91 (m, 2H), 5.93 (s, 2H), 5.05 (s, 2H), 4.05 (s, 3H), 3.67 (s, 3H) ppm.

LCMS: 99.39% ESI-MS (m/z): 381.09[M+1]+. HPLC: 98.61%.

Compound C29: 3-((9-methoxy-5-methyl-8-nitro-6-oxo-5,6-dihydropyrimido[5,4-c]isoquinolin-2-yl)amino)benzonitrile

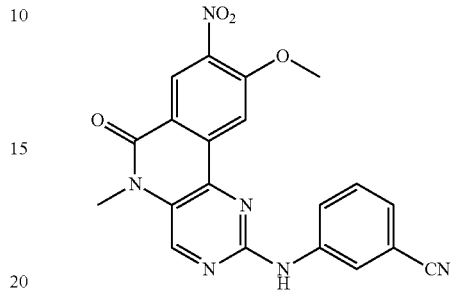

To a stirred solution of 4-bromo-6-methoxy-2-methyl-7-nitro-1-oxo-1,2-dihydroisoquinoline-3-carbaldehyde (A2) (150 mg, 0.439 mmole) in DMF (2 ml) was added 1-(3-cyanophenyl)guanidine (B7) (140 mg, 0.879 mmole) and K₂CO₃ (180 mg, 1.31 mmole). The reaction mixture was heated at 90° C. for 2 hrs. Water (3 ml) was then added and the thus obtained solid was filtered, washed with water (10 ml×3), dried under vacuum to get a crude product which was triturated with hexane to get the pure expected compound (80 mg, Yield: 45.21%).

LCMS: 68.27% ESI-MS (m/z): 401.20[M−1]−.

Compound C30: 8-amino-2-((3-(aminomethyl)phenyl)amino)-9-methoxy-5-methylpyrimido[5,4-c]isoquinolin-6(5H)-one

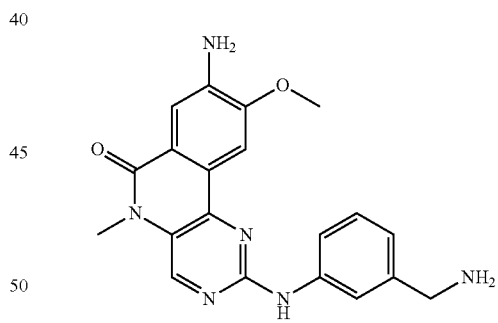

To a stirred suspension of Raney nickel (30 mg) in methanol (2 ml) was added 3-((9-methoxy-5-methyl-8-nitro-6-oxo-5,6-dihydropyrimido[5,4-c]isoquinolin-2-yl)amino)benzonitrile (C29) (80 mg, 0.206 mmole) in methanolic ammonia (10 ml). The reaction mixture was stirred overnight at RT over 50 psi of H₂ gas. The reaction mixture was filtered through Celite® and washed with methanol (20 ml×3). Combined filtrates were evaporated under vacuum to get a crude material which purified by flash chromatography (20 mg, Yield: 25.79%).

$^1$H NMR (400 MHz, DMSO-d6): δ 9.77 (s, 1H) 8.74 (s, 1H), 8.20 (s, 1H), 8.00 (s, 1H), 7.73 (m, 3H), 7.55 (s, 1H), 7.37 (s, 1H), 7.09 (s, 1H), 5.99 (s, 2H), 4.07 (s, 3H), 3.99 (s, 2H), 3.69 (s, 3H) ppm.

LCMS: 96.33% ESI-MS (m/z): 377.19 [M+1]+. HPLC: 95.18%.

Compound C31: 24(3-aminophenyl)amino)-8-nitropyrimido[5,4-c]isoquinolin-6(5H)-one

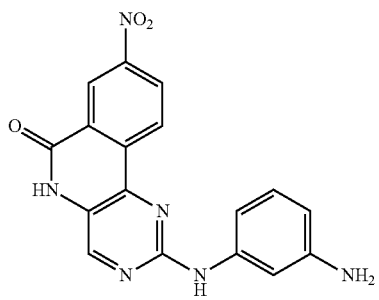 [SMILES: Nc1cccc(Nc2ncc3[nH]c(=O)c4cc([N+](=O)[O-])ccc4c3n2)c1]

To a stirred solution of 4-bromo-7-nitro-1-oxo-1,2-dihydroisoquinoline-3-carbaldehyde (A4) (0.15 g, 0.54 mmole) in DMF (10 ml) was added 1-(3-aminophenyl)guanidine (B1) (0.151 g, 1.1 mmole) and $K_2CO_3$ (0.209 g, 1.51 mmole). The reaction mixture was heated at 90° C. for 2 hrs. Water
(10 ml) was then added and the solid was filtered. The solid was then washed with water (15 ml×3), dried under vacuum and triturated with hexane to get the expected compound (0.08 g, Yield: 45.48%).

LCMS: 67.08% ESI-MS (m/z): 347.12 [M−1]⁻.

Compound C32: 8-amino-2-((3-aminophenyl)amino)pyrimido[5,4-c]isoquinolin-6(5H)-one

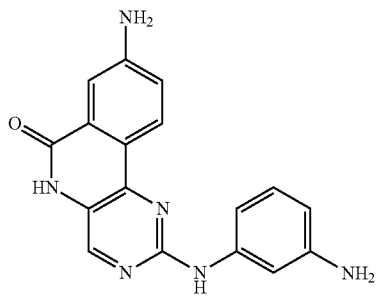

To a stirred solution of 2-((3-aminophenyl)amino)-8-nitropyrimido[5,4-c]isoquinolin-6(5H)-one (C32) (80 mg, 0.22 mmole) in DMSO (1 ml) was added NaSH (61 mg, 1.1 mmole). The reaction mixture was stirred a room temperature for 1 hr. Water (8 ml) was then added and the thus obtained suspension was extracted with ethyl acetate (10 ml×2). Combined organic layers were washed with brine (10 ml×2), dried over sodium sulfate and evaporated under vacuum to get a crude material which was purified by flash chromatography (15 mg, Yield: 20.40%).

$^1$H NMR (400 MHz, DMSO-d$^6$): δ 11.35 (s, 1H), 9.19 (s, 1H), 8.40 (t, J=8.4 Hz, 2H), 7.41 (s, 1H), 7.24 (s, 1H), 7.15 (d, J=9.2 Hz, 1H), 6.97-9.93 (m, 2H), 6.24 (s, 2H), 6.17 (d, J=6 Hz, 1H), 5.03 (s, 2H) ppm.

LCMS: 98.25% ESI-MS (m/z): 319 [M+1]⁺. HPLC: 97.08%.

Compound C33: 5-methyl-8-nitro-2-((4-(2-(pyrrolidin-1-yl)ethoxy)phenyl)amino)pyrimido[5,4-c]isoquinolin-6(5H)-one

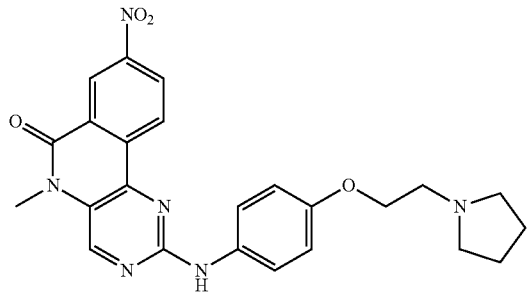 [SMILES: Cn1c(=O)c2cc([N+](=O)[O-])ccc2c2nc(Nc3ccc(OCCN4CCCC4)cc3)ncc21]

To a stirred solution of 4-bromo-2-methyl-7-nitro-1-oxo-1,2-dihydroisoquinoline-3-carbaldehyde (A1) (800 mg, 2.58 mmole) in DMF (10 ml) was added 1-(4-(2-(pyrrolidin-1-yl)ethoxy) phenyl)guanidine (B8) (830 mg, 3.36 mmole) and $K_2CO_3$ (1.06 gm, 7.74 mmole). The reaction mixture was heated at 90° C. for 2 hrs. Water was then added and the solid was filtered, washed with water (25 ml×3), dried under vacuum and triturated with hexane to get the expected compound (550 mg, Yield: 46.21%).

Compound C34: 8-amino-5-methyl-2-((4-(2-(pyrrolidin-1-yl)ethoxy)phenyl)amino)pyrimido[5,4-c]isoquinolin-6(5H)-one

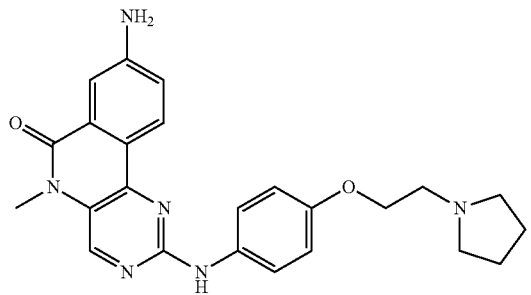 [SMILES: Cn1c(=O)c2cc(N)ccc2c2nc(Nc3ccc(OCCN4CCCC4)cc3)ncc21]

To a stirred solution of 5-methyl-8-nitro-2-((4-(2-(pyrrolidin-1-yl)ethoxy)phenyl)amino)pyrimido[5,4-c]isoquinolin-6(5H)-one (C33) (400 mg, 0.86 mmole) in acetic acid (5 ml) was added iron powder (200 mg, 4.34 mmole). The reaction mixture was stirred 1 hour at 90° C. Ethyl acetate was then added, the solid was filtered and washed with ethyl acetate (ml×3). Combined filtrates were evaporated under vacuum and the thus obtained solid was triturated with ethyl acetate and hexane to get the pure expected compound (300 mg, Yield: 80.42%).

$^1$H NMR (400 MHz, DMSO-d$^6$): δ 9.36 (s, 1H), 8.66 (s, 1H), 8.38 (d, J=8.4 Hz, 1H), 7.76 (d, J=9.2 Hz, 2H), 7.47 (d, J=2.4 Hz, 1H), 7.12 (dd, J=2.4, 8.8 Hz, 1H), 6.95 (d, J=9.2 Hz, 2H), 6.26 (s, 2H), 4.05 (t, J=5.6 Hz, 2H), 3.72 (s, 3H), 2.79 (t, J=4.8 Hz, 2H), 2.54 (s, 4H), 1.69 (s, 4H) ppm.

LCMS: 98.09% ESI-MS (m/z): 431.45 [M+1]⁺. HPLC: 97.53%.

Compound C35: N-(5-methyl-6-oxo-2-((4-(2-(pyrrolidin-1-yl)ethoxy)phenyl)amino)-5,6 dihydropyrimido[5,4-c]isoquinolin-8-yl)acetamide

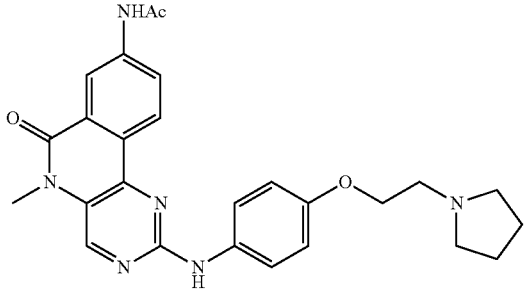 [SMILES: CC(=O)Nc1ccc2c(c1)c(=O)n(C)c1cnc(Nc3ccc(OCCN4CCCC4)cc3)nc21]

A stirred solution of 8-amino-5-methyl-2-((4-(2-(pyrrolidin-1-yl)ethoxy)phenyl)amino)pyrimido[5,4-c]isoquinolin-6(5H)-one (C34) (150 mg, 0.348 mmole) in acetic anhydride (2 ml) was heated at 90° C. for 2 hrs. Solvent was removed under vacuum and the crude material was triturated with hexane and ethyl acetate to get the expected compound (40 mg, Yield: 24.29%).

$^1$H NMR (400 MHz, DMSO-d$^6$): δ 10.54 (s, 1H), 9.55 (s, 1H), 8.82 (s, 1H), 8.63 (d, J=8 Hz 2H), 8.19 (d, J=8.8 Hz, 1H), 7.78 (d, J=8.8 Hz, 2H), 6.96 (d, J=8.8 Hz, 2H), 4.06 (t, J=5.6 Hz, 2H), 3.71 (s, 3H), 2.83 (s, 2H), 2.57 (s, 4H), 2.14 (s, 4H) ppm.

LCMS: 96.03% ESI-MS (m/z): 473.21[M+1]$^+$. HPLC: 95.80%.

Compound C36: 5-methyl-2-((4-(2-(pyrrolidin-1-yl)ethoxy)phenyl)amino)pyrimido[5,4-c]isoquinolin-6(5H)-one (C37)

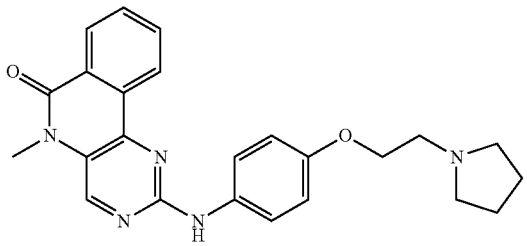

To a stirred solution of 4-bromo-2-methyl-1-oxo-1,2-dihydroisoquinoline-3-carbaldehyde (A3) (0.15 g, 0.566 mmole) in DMF (10 ml) was added 1-(4-(2-(pyrrolidin-1-yl)ethoxy)phenyl)guanidine (B8) (0.28 g, 1.13 mmole) and Cs$_2$CO$_3$ (0.55 gm, 1.69 mmole). The reaction mixture was heated at 90° C. for 2 hrs. Water was then added and the thus obtained solid was filtered, washed with water (25 ml×3), dried under vacuum and triturated by hexane and ethyl acetated to get the expected compound (0.03 g, Yield: 12.80%).

$^1$H NMR (400 MHz, DMSO-d$^6$): δ 9.87 (s, 1H), 9.44 (s, 1H), 8.45 (d, J=7.2 Hz 1H), 8.28 (d, J=8.4 Hz 1H), 7.82 (t, J=8 Hz, 1H), 7.72 (d, J=8.4 Hz, 2H), 7.54 (t, J=6.8 Hz, 1H), 6.95 (d, J=8.4 Hz, 2H), 4.05 (s, 2H), 3.70 (s, 3H), 2.76 (s, 4H), 1.99 (s, 4H), 1.70 (s, 4H) ppm.

LCMS: 91.48% ESI-MS (m/z): 461.19 [M+1]$^+$. HPLC: 92.36%.

Compound C37: 9-methoxy-2-((3-methoxy-4-(2-(pyrrolidin-1-yl)ethoxy)phenyl)amino)-5-methyl-8-nitropyrimido[5,4-c]isoquinolin-6(5H)-one

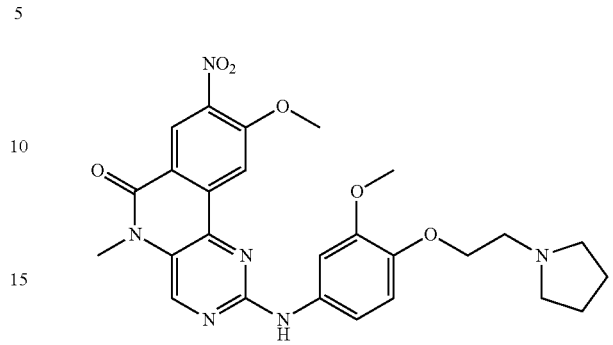

To a stirred solution of 4-bromo-6-methoxy-2-methyl-7-nitro-1-oxo-1,2-dihydroisoquinoline-3-carbaldehyde (A2) (200 mg, 0.586 mmole) in DMF (2 ml) was added 1-(3-methoxy-4-(2-(pyrrolidin-1-yl)ethoxy)phenyl)guanidine (B9) (326 mg, 1.17 mmole) and K$_2$CO$_3$ (243 mg, 1.76 mmole). The reaction mixture was heated at 90° C. for 2 hrs. Water (10 ml) was added and the thus obtained solid was filtered, washed with water (10 ml×3) and dried under vacuum to get a crude mixture which was triturated with hexane to get the expected compound (150 mg, Yield: 49.15%).

LCMS: 77.14% ESI-MS (m/z): 521.29 [M+1]$^+$.

Compound C38: 8-amino-9-methoxy-2-((3-methoxy-4-(2-(pyrrolidin-1-yl)ethoxy)phenyl)amino)-5-methylpyrimido[5,4-c]isoquinolin-6(5H)-one

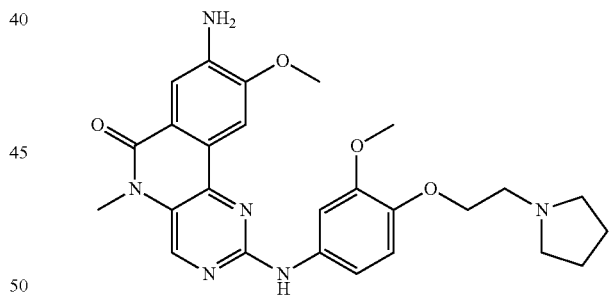

To a stirred solution of 9-methoxy-2-((3-methoxy-4-(2-(pyrrolidin-1-yl)ethoxy)phenyl)amino)-5-methyl-8-nitropyrimido[5,4-c]isoquinolin-6(5H)-one (C38) (150 mg, 0.288 mmole) in acetic acid (5 ml) was added iron powder (80 mg, 1.44 mmole). The reaction mixture was heated at 90° C. for 2 hrs. Ethyl acetate (10 ml) was added and the solid was filtered, Combined filtrates were washed with saturated NaHCO$_3$ solution (10 ml×3), dried over anhydrous sodium sulfate and evaporated under vacuum to get a crude product which was purified by preparative HPLC (15 mg, Yield: 10.16%).

$^1$H NMR (400 MHz, DMSO-d$^6$): δ 9.38 (s, 1H), 8.70 (s, 1H), 7.95 (s, 1H), 7.54 (d, J=6.4 Hz, 1H), 7.44 (d, J=8.4 Hz, 1H), 6.94 (d, J=8.8 Hz, 1H), 5.95 (s, 2H), 4.01 (s, 4H), 3.79 (s, 3H), 3.68 (s, 3H), 2.77 (s, 4H), 1.72 (s, 4H) ppm.

LCMS: 100% ESI-MS (m/z): 491.62 [M+1]+. HPLC: 100%.

Compound C39: 9-methoxy-2-((2-methoxy-4-(2-(pyrrolidin-1-yl)ethoxy)phenyl)amino)-5-methyl-8-nitropyrimido[5,4-c]isoquinolin-6(5H)-one

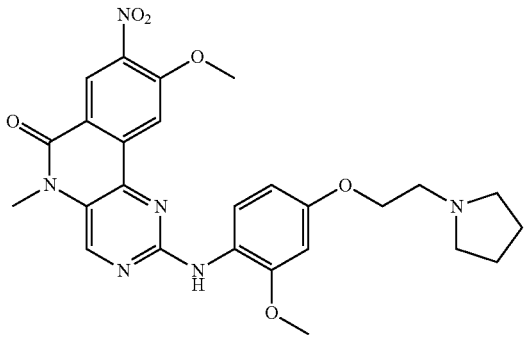

To a stirred solution of 4-bromo-6-methoxy-2-methyl-7-nitro-1-oxo-1,2-dihydroisoquinoline-3-carbaldehyde (A2) (200 mg, 0.586 mmole) in DMF (2 ml) was added 1-(2-methoxy-4-(2-(pyrrolidin-1-yl)ethoxy)phenyl)guanidine (B10) (326 mg, 1.17 mmole) and $K_2CO_3$ (243 mg, 1.76 mmole). The reaction was heated at 90° C. for 2 hrs. Water (15 ml) was then added and the solid was filtered, washed with water (10 ml×3) and dried under vacuum to get a crude material which was triturated with hexane (150 mg, Yield: 49.15%).

LCMS: 80.43% ESI-MS (m/z): 521.19 [M+1]+.

Compound C40: 8-amino-9-methoxy-2-((2-methoxy-4-(2-(pyrrolidin-1-yl)ethoxy)phenyl)amino)-5-methylpyrimido[5,4-c]isoquinolin-6(5H)-one

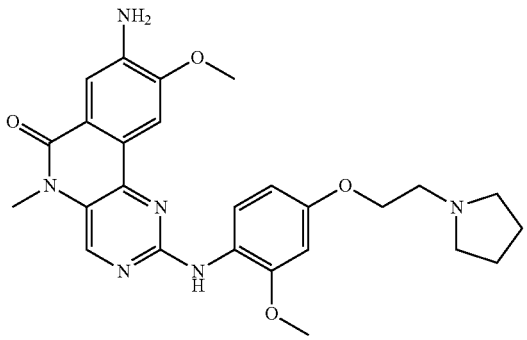

To a stirred solution of 9-methoxy-2-((2-methoxy-4-(2-(pyrrolidin-1-yl)ethoxy)phenyl)amino)-5-methyl-8-nitropyrimido[5,4-c]isoquinolin-6(5H)-one (C39) (150 mg, 0.288 mmole) in acetic acid (5 ml) was added iron powder (80 mg, 1.44 mmole). The reaction mixture was heated at 90° C. for 2 hrs. Ethyl acetate (10 ml) was then added and the solid was filtered and washed with saturated $NaHCO_3$ solutions (10 ml×3). The combined organic layers were dried over anhydrous sodium sulfate and evaporated under vacuum to get a crude material which was purified by preparative HPLC (15 mg, Yield: 10.16%).

$^1$H NMR (400 MHz, DMSO-d$^6$): δ 8.64 (s, 1H), 8.18 (d, J=8.4 Hz, 1H), 7.93 (s, 2H), 7.53 (s, 1H), 6.75 (s, 1H), 6.67 (t, J=7.6 Hz, 1H), 5.95 (s, 2H), 4.30 (s, 2H), 4.02 (s, 3H), 3.88 (s, 3H), 3.66 (s, 3H), 3.57-3.51 (m, 4H), 1.93 (s, 4H) ppm.

LCMS: 100% ESI-MS (m/z): 491.33 [M+1]+. HPLC: 99.42%.

Compound C41: 9-methoxy-5-methyl-8-nitro-2-((4-(2-(pyrrolidin-1-yl)ethoxy)phenyl)amino) pyrimido[5,4-c]isoquinolin-6(5H)-one

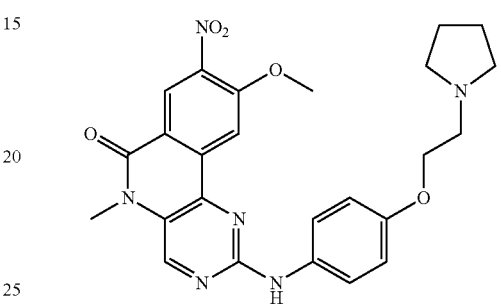

To a stirred solution of 4-bromo-6-methoxy-2-methyl-7-nitro-1-oxo-1,2-dihydroisoquinoline-3-carbaldehyde (A2) (100 mg, 0.294 mmole) in DMF (2 ml) was added 1-(4-(2-(pyrrolidin-1-yl)ethoxy)phenyl)guanidine (B8) (87.5 mg, 0.352 mmole) and $K_2CO_3$ (81.1 mg, 0.588 mmole). The reaction mixture was heated at 90° C. for 2 hrs. Water (10 ml) was then added and the solid was filtered, washed with water (10 ml×3), and dried under vacuum to get a crude product which was triturated with hexane to get the expected compound (75 mg, Yield: 52.16%).

LCMS: 92.90% ESI-MS (m/z): 491.47 [M+1]+.

Compound C42: 8-amino-9-methoxy-5-methyl-2-((4-(2-(pyrrolidin-1-yl)ethoxy)phenyl)amino) pyrimido[5,4-c]isoquinolin-6(5H)-one

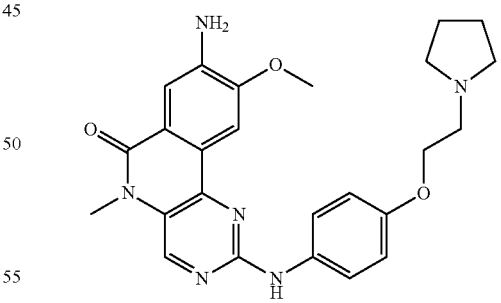

To a stirred solution of 9-methoxy-5-methyl-8-nitro-2-((4-(2-(pyrrolidin-1-yl)ethoxy)phenyl)amino) pyrimido[5,4-c]isoquinolin-6(5H)-one (C41) (75 mg, 0.153 mmole) in acetic acid (5 ml) was added iron powder (42.7 mg, 0.765 mmole). The reaction mixture was heated at 90° C. for 1 hr. Ethyl acetate (10 ml) was added and the solid was filtered and washed with ethyl acetate (10 ml×3). Combined filtrates were evaporated under vacuum to get a crude product which was triturated with ethyl acetate and hexane to get the pure expected compound (35 mg, Yield: 50%).

¹H NMR (400 MHz, DMSO-d⁶): δ 9.48 (s, 1H), 8.69 (s, 1H), 7.96 (s, 1H), 7.84 (d, J=8.8 Hz, 2H), 7.54 (s, 1H), 7.01 (d, J=8.8 Hz, 2H), 5.97 (s, 2H), 4.31 (t, J=4.4 Hz, 2H), 4.03 (s, 3H), 3.68 (s, 3H), 3.58 (br, 4H), 3.17-3.13 (m, 2H), 2.03 (Br, 2H), 1.91 (Br, 2H) ppm.

LCMS: 89.90% ESI-MS (m/z): 461.61 [M+1]⁺. HPLC: 89.33%.

Compound C43: 2-((3-methoxy-4-(2-(pyrrolidin-1-yl)ethoxy)phenyl)amino)-5-methyl-8-nitro pyrimido[5,4-c]isoquinolin-6(5H)-one

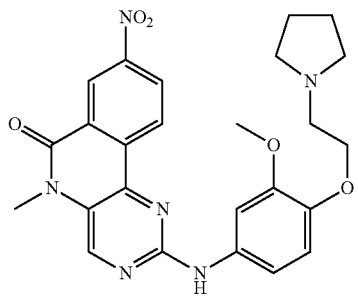

To a solution of 4-bromo-2-methyl-7-nitro-1-oxo-1,2-dihydroisoquinoline-3-carbaldehyde (A1) (200 mg, 0.6451 mmole) in DMF (1 ml) was added 1-(3-methoxy-4-(2-(pyrrolidin-1-yl)ethoxy)phenyl)guanidine (B9) (270 mg, 0.9676 mmole). K₂CO₃ (176 mg, 1.29 mmole) was added and heated at 90° C. for 2 hrs. Water was added and solid was filtered, solid was washed with water (10 ml×3) and dried under vacuum to get crude product which was triturated by hexane to get title compound. (100 mg Yield: 31.71%).

Compound C44: 8-amino-2-((3-methoxy-4-(2-(pyrrolidin-1-yl)ethoxy)phenyl)amino)-5-methyl pyrimido[5,4-c]isoquinolin-6(5H)-one

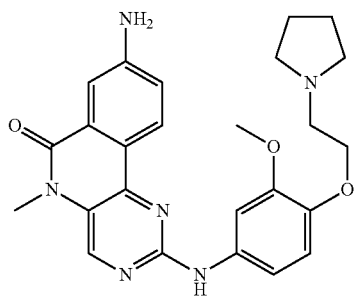

To a stirred solution of 2-((3-methoxy-4-(2-(pyrrolidin-1-yl)ethoxy)phenyl)amino)-5-methyl-8-nitropyrimido[5,4-c]isoquinolin-6(5H)-one (C43) (100 mg, 0.2040 mmole) in acetic acid (5 ml) was added iron powder (100 mg, 2.040 mmole). The reaction mixture was heated at 90° C. and stirred for 1 hr. Ethyl acetate (10 ml) was then added and the solid was filtered and washed with ethyl acetate (10 ml×3). Combined filtrates were evaporated under vacuum to get a crude product which was purified by preparative HPLC (60 mg, Yield: 63.61%).

¹H NMR (400 MHz, DMSO-d⁶): δ 9.47 (s, 1H), 8.69 (s, 1H), 8.40 (d, J=8.4 Hz, 1H), 7.74 (s, 1H), 7.47 (s, 1H), 7.39 (d, J=7.6 Hz, 1H), 7.12-7.05 (m, 2H), 4.20 (s, 2H), 3.93 (s, 3H), 3.54 (s, 3H), 3.49-3.40 (m, 2H), 3.15 (s, 4H), 2.05 (s, 2H), 1.91 (s, 2H) ppm.

LCMS: 97.23% ESI-MS (m/z): 461.26 [M+1]⁺. HPLC: 96.33%.

Compound C45: 2-((2-methoxy-4-(2-(pyrrolidin-1-yl)ethoxy)phenyl)amino)-5-methyl-8-nitro pyrimido[5,4-c]isoquinolin-6(5H)-one

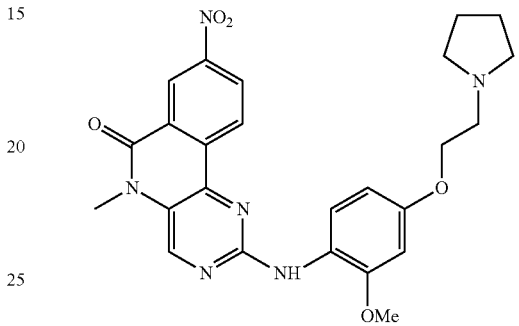

To a stirred solution of 4-bromo-2-methyl-7-nitro-1-oxo-1,2-dihydroisoquinoline-3-carbaldehyde (A1) (100 mg, 0.3225 mmole) in DMF (1 ml) was added 1-(2-methoxy-4-(2-(pyrrolidin-1-yl)ethoxy)phenyl)guanidine (B10) (134 mg, 0.4838 mmole) and K₂CO₃ (88 mg, 0.6451 mmole). The reaction mixture was heated at 90° C. for 2 hrs. Water was then added, the solid was filtered, washed with additional water (10 ml×3) and dried under vacuum to get a crude product which was triturated with hexane (107 mg, Yield: 67.86%).

Compound C46: 8-amino-2-((3-methoxy-4-(2-(pyrrolidin-1-yl)ethoxy)phenyl)amino)-5-methyl pyrimido[5,4-c]isoquinolin-6(5H)-one

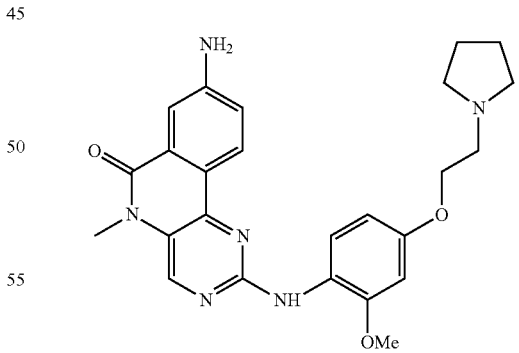

To a stirred solution of 2-((2-methoxy-4-(2-(pyrrolidin-1-yl)ethoxy)phenyl)amino)-5-methyl-8-nitropyrimido[5,4-c]isoquinolin-6(5H)-one (C45) (100 mg, 0.2040 mmole) in acetic acid (5 ml) was added iron powder (100 mg, 2.040 mmole). The reaction mixture was heated at 90° C. for 1 hour. Ethyl acetate (10 ml) was added, the solid was filtered and washed with ethyl acetate (10 ml×3). Combined filtrates were evaporated under vacuum to get a crude product which was triturated with methanol to get the pure expected compound (18 mg, Yield: 17.92%).

$^1$H NMR (400 MHz, DMSO-d$^6$): δ 9.76 (s, 1H), 8.63 (s, 1H), 8.34 (d, J=8.8 Hz, 1H), 8.18 (d, J=8.8 Hz, 1H), 7.91 (s, 1H), 7.47 (d, J=2.4 Hz, 1H), 7.10 (dd, J=2.4 Hz, 8.8 Hz, 1H), 6.75-6.69 (m, 2H), 4.32 (t, J=4.8 Hz, 2H), 3.87 (s, 3H), 3.66 (s, 2H), 3.65-3.59 (m, 2H), 3.18-3.13 (m, 2H), 2.08 (s, 2H), 1.91 (s, 2H) ppm.

LCMS: 99.43% ESI-MS (m/z): 461.26 [M+1]$^+$. HPLC: 98.01%.

2. Biological Activity of the Compounds According to the Invention

The following abbreviations are used in the following examples:

$EC_{50}$=Concentration of a compound where 50% of its maximal effect is observed FCS=Foetal calf serum $IC_{50}$=Concentration of a compound which induces 50% inhibition IMDM=Iscove's Modified Dulbecco's Medium PSFG=Penicilin streptomycin fungizone RPMI=Roswell Park Memorial Institute medium

2.1. Enzymatic Assays

Recombinant FLT3 (#PV3182), JAK2 (#PV4210) and JAK3 (#PV3855) enzymes were purchased from Life Technologies. FLT3-ITD (#0778-0000-1) and FLT3$^{D835Y}$ (#14-610) were respectively purchased from Proquinase and Merck Millipore.

The assays were conducted in 384-well plates based on Life Technologies Lanthascreen® TR-FRET methodologies.

FLT3-ITD or FLT3$^{D835Y}$ assays: 15 nM of FLT3-ITD or FLT3$^{D835Y}$, 3 nM of the 236 kinase tracker (Life Technologies #PV5592) and 6 nM of the Europium-tagged anti-GST Lanthascreen® antibody are mixed into 15 μL total volume reaction mixture.

FLT3 assays: 15 nM of FLT3, 3 nM of the 236 kinase tracker (Life Technologies #PV5592) and 6 nM of the Europium-tagged anti-His Lanthascreen® antibody are mixed into 15 μL total volume reaction mixture.

JAK2 assays: 15 nM of JAK2, 150 nM of the 236 kinase tracker (Life Technologies #PV5592) and 6 nM of the Europium-tagged anti-GST Lanthascreen® antibody are mixed into 15 μL total volume reaction mixture.

JAK3 assays: 15 nM of JAK2, 3 nM of the 236 kinase tracker (Life Technologies #PV5592) and 6 nM of the Europium-tagged anti-GST Lanthascreen® antibody are mixed into 15 μL total volume reaction mixture.

$IC_{50}$s were determined from a 8-point dose-response curve spanning a >1000 fold concentration range using a 10 mM compound solution stock into pure DMSO (Sigma #D8418). The overall DMSO concentrations of tested solutions were 1%. Reaction were left to proceed 1 hour at 25° C. and revealed with a Perkin Elmer Envision spectrometer according to Life Technologies recommendations.

$IC_{50}$s were generated with the software Prism (Graphpad). Results are present in Table 1.

TABLE 1

$IC_{50}$ < 25 nM: A; 25 nM ≤ $IC_{50}$ < 100 nM: B; 100 nM ≤ $IC_{50}$ < 1 μM: C; $IC_{50}$ ≥ 1 μM: D.

| | Enzymology ($IC_{50}$) | | | | |
|---|---|---|---|---|---|
| Ex. | FLT3 wt | FLT3-ITD | FLT3 D835Y | JAK2 | JAK3 |
| C2 | B | A | A | B | B |
| C4 | B | A | A | C | B |
| C6 | B | A | A | C | B |
| C10 | B | A | A | C | B |
| C22 | C | A | A | C | B |
| C26 | C | B | B | C | C |
| C28 | C | A | B | C | C |
| C34 | B | A | A | C | C |
| C42 | C | A | A | C | C |

2.2. Antiproliferative Activity Assays

Cell lines MV4-11 and MOLM-13 are grown according to conditions depicted in Table 2 following the provider recommendations.

TABLE 2

| | | Growing conditions | | | |
|---|---|---|---|---|---|
| Cell Lines | Provider | Pathology | Oncogene Status | Medium of Culture | Seeding density |
| MV4-11 | DSMZ | Acute Myeloid Leukemia (AML) | FLT3-ITD | IMDM, 10% FCS, PSFG | 0.4 10$^5$ cells/well (100 μl) |
| MOLM-13 | DSMZ | Acute Myeloid Leukemia (AML) | FLT3-ITD | RPMI 1640, 15% FCS, PSFG | 0.3 10$^5$ cells/well (100 μl) |

Assays are being run into 96-well plates. Cells are passaged at Day 0, seeded at Day 1 and added with increasing quantities of the compounds to evaluate. Plates are incubated for 72 h at 37° C. under a 5% CO$_2$ atmosphere.

Half-logarithmic dilutions from compounds stock solutions in DMSO (Sigma #D8414) were done in order to obtain 0.1% DMSO solutions.

Cellular viability is measured at Day 4 with the ATPLite (Perkin Elmer #6016947) kit.

$EC_{50}$s was calculated using an internally developed curve fitting software and presented in Table 3.

TABLE 3

$EC_{50}$ < 25 nM: A; 25 nM ≤ $EC_{50}$ < 100 nM: B; 100 nM ≤ $EC_{50}$ < 1 μM: C; $EC_{50}$ ≥ 1 μM: D.

| | Inhibition of proliferation (EC50) | |
|---|---|---|
| Compound | MV411 | MOLM13 |
| C2 | B | B |
| C4 | A | A |
| C6 | B | B |
| C10 | A | C |
| C22 | C | C |
| C26 | B | B |
| C28 | B | C |
| C34 | C | C |
| C42 | C | C |

The invention claimed is:

1. A compound of the following formula (I):

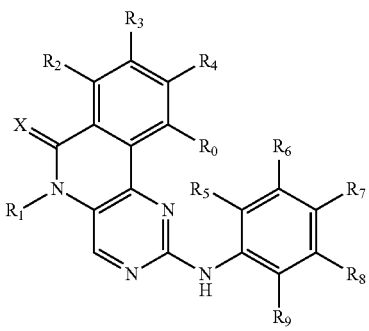

or a pharmaceutically acceptable salt thereof,
wherein:
X is selected from O, NH and S,
$R_0$ is H; halo; $(C_1-C_6)$alkyl; $(C_1-C_6)$haloalkyl; $(C_1-C_6)$alkoxy; or $(C_1-C_6)$haloalkoxy,
$R_1$ is selected from H and $(C_1-C_3)$alkyl,
$R_2$, $R_3$, $R_5$, $R_7$, $R_8$ and $R_9$ are, independently of one another, selected from H; halo; nitro $(NO_2)$; cyano (CN); $R_{10}$; $OR_{11}$; $SR_{12}$; $S(O)R_{13}$; $SO_2R_{14}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated heterocycle, comprising one to three heteroatoms chosen from O, N and S, optionally substituted with one or several groups selected from halo, nitro $(NO_2)$, cyano (CN), oxo (=O), $(C_1-C_6)$alkyl, OH, $CO_2H$, $(C_1-C_6)$alkoxy, $CO_2$—$(C_1-C_6)$alkyl and $NR_{24}R_{25}$,
$R_4$ and $R_6$ are, independently of each other, selected from H; halo; nitro $(NO_2)$; cyano (CN); $R_{10}$; $OR_{11}$; $SR_{12}$; $S(O)R_{13}$; $SO_2R_{14}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated heterocycle comprising one to three heteroatoms chosen from O, N and S, optionally substituted with one or several groups selected from halo, nitro $(NO_2)$, cyano (CN), oxo (=O), $(C_1-C_6)$alkyl, OH, $CO_2H$, $(C_1-C_6)$alkoxy, $CO_2$—$(C_1-C_6)$alkyl and $NR_{24}R_{25}$, or
$R_4$ and $R_6$ form together a hydrocarbon chain comprising 4 to 10 carbon atoms optionally substituted with one or several groups selected from halo and $(C_1-C_6)$alkyl, where one or several non-adjacent carbon atoms of the saturated hydrocarbon chain are optionally replaced with O, S or $NR_{30}$;
$R_{10}$, $R_{11}$, $R_{12}$, $R_{13}$, $R_{14}$, $R_{17}$, $R_{18}$, $R_{19}$, $R_{22}$, $R_{23}$ and $R_{30}$ are, independently of one another, H or a $(C_1-C_6)$alkyl, $(C_2-C_6)$alkenyl or $(C_2-C_6)$alkynyl group optionally substituted with one or several groups selected from halo, nitro $(NO_2)$, cyano (CN), OH, $CO_2H$, $(C_1-C_6)$alkoxy, $CO_2$—$(C_1-C_6)$alkyl and $NR_{26}R_{27}$,
$R_{15}$, $R_{16}$, $R_{20}$ and $R_{21}$ are, independently of one another, H or a $(C_1-C_6)$alkyl, $(C_2-C_6)$alkenyl or $(C_2-C_6)$alkynyl group optionally substituted with one or several groups selected from halo, nitro $(NO_2)$, cyano (CN), OH, $CO_2H$, $(C_1-C_6)$alkoxy, $CO_2$—$(C_1-C_6)$alkyl and $NR_{26}R_{27}$, or $R_{15}$ and $R_{16}$ and/or $R_{20}$ and $R_{21}$ form together, with the nitrogen atom which carries them, a 3- to 7-membered saturated or unsaturated heterocycle optionally comprising one or two heteroatoms chosen from O, N and S in addition to the nitrogen atom, optionally substituted with one or several groups selected from halo, nitro $(NO_2)$, cyano (CN), oxo (=O), $(C_1-C_6)$alkyl, OH, $CO_2H$, $(C_1-C_6)$alkoxy, $CO_2$—$(C_1-C_6)$alkyl and $NR_{28}R_{29}$,
$R_{24}$, $R_{25}$, $R_{26}$, $R_{27}$, $R_{28}$ and $R_{29}$ are, independently of each other, H or a $(C_1-C_6)$alkyl group, or $R_{24}$ and $R_{25}$ and/or $R_{26}$ and $R_{27}$ and/or $R_{28}$ and $R_{29}$ form together, with the nitrogen atom which carries them, a 3- to 7-membered saturated or unsaturated heterocycle optionally comprising one or two heteroatoms chosen from O, N and S in addition to the nitrogen atom, optionally substituted with one or several groups selected from halo, oxo (=O) and $(C_1-C_6)$alkyl.

2. The compound according to claim 1, wherein X is O.

3. The compound according to claim 1, wherein $R_2$, $R_3$, $R_5$, $R_7$, $R_8$ and $R_9$ are, independently of one another, selected from H; halo; nitro $(NO_2)$; cyano (CN); $R_{10}$; $OR_{11}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated heterocycle comprising one to three heteroatoms chosen from O and N, optionally substituted with one or several groups selected from halo, nitro $(NO_2)$, cyano (CN), oxo (=O), $(C_1-C_6)$alkyl, OH, $CO_2H$, $(C_1-C_6)$alkoxy, $CO_2$—$(C_1-C_6)$alkyl and $NR_{24}R_{25}$, and
$R_4$ and $R_6$ are, independently of each other, selected from H; halo; nitro $(NO_2)$; cyano (CN); $R_{10}$; $OR_{11}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated heterocycle comprising one to three heteroatoms chosen from O and N, optionally substituted with one or several groups selected from halo, nitro $(NO_2)$, cyano (CN), oxo (=O), $(C_1-C_6)$alkyl, OH, $CO_2H$, $(C_1-C_6)$alkoxy, $CO_2$—$(C_1-C_6)$alkyl and $NR_{24}R_{25}$, or
$R_4$ and $R_6$ form together a hydrocarbon chain comprising 4 to 10 carbon atoms optionally substituted with one or several groups selected from halo and $(C_1-C_6)$alkyl, where one or several non-adjacent carbon atoms of the saturated hydrocarbon chain are substituted with O, S or $NR_{30}$.

4. The compound according to claim 1, wherein $R_0$ is H and $R_2$, $R_3$, $R_5$, $R_7$, $R_8$ and $R_9$ are, independently of one another, selected from H; halo; nitro $(NO_2)$; cyano (CN); $R_{10}$; $OR_{11}$; $NR_{15}R_{16}$; $OC(O)R_{19}$; $NR_{22}C(O)R_{23}$; and a 5- to 7-membered saturated or unsaturated heterocycle comprising one or two heteroatoms chosen from O and N, optionally substituted with one or several groups selected from halo, nitro $(NO_2)$, cyano (CN), oxo (=O), $(C_1-C_6)$alkyl, OH, $(C_1-C_6)$alkoxy and $NR_{24}R_{25}$, and
$R_4$ and $R_6$ are, independently of one another, selected from H; halo; nitro $(NO_2)$; cyano (CN); $R_{10}$; $OR_{11}$; $NR_{15}R_{16}$; $OC(O)R_{19}$; $NR_{22}C(O)R_{23}$; and a 5- to 7-membered saturated or unsaturated heterocycle comprising one or two heteroatoms chosen from O and N, optionally substituted with one or several groups selected from halo, nitro $(NO_2)$, cyano (CN), oxo (=O), $(C_1-C_6)$alkyl, OH, $(C_1-C_6)$alkoxy and $NR_{24}R_{25}$, or
$R_4$ and $R_6$ form together a saturated hydrocarbon chain comprising 4 to 10 carbon atoms optionally substituted with one or several groups selected from halo and $(C_1-C_6)$alkyl, where one or several non-adjacent carbon atoms of the saturated hydrocarbon chain are substituted with O, S or $NR_{30}$.

5. The compound according to claim 1, wherein $R_{10}$, $R_{11}$, $R_{12}$, $R_{13}$, $R_{14}$, $R_{17}$, $R_{18}$, $R_{19}$, $R_{22}$, $R_{23}$ and $R_{30}$ are, independently of one another, H or a ($C_1$-$C_6$)alkyl group optionally substituted with one or several groups selected from halo, nitro ($NO_2$), cyano (CN), OH, $CO_2H$, ($C_1$-$C_6$)alkoxy, $CO_2$—($C_1$-$C_6$)alkyl and $NR_{26}R_{27}$, and $R_{15}$, $R_{16}$, $R_{20}$ and $R_{21}$ are, independently of one another, H or a ($C_1$-$C_6$)alkyl group optionally substituted with one or several groups selected from halo, nitro ($NO_2$), cyano (CN), OH, $CO_2H$, ($C_1$-$C_6$)alkoxy, $CO_2$—($C_1$-$C_6$)alkyl and $NR_{26}R_{27}$, or $R_{15}$ and $R_{16}$ and/or $R_{20}$ and $R_{21}$ form together, with the nitrogen atom which carries them, a 5- to 7-membered saturated or unsaturated heterocycle optionally comprising one heteroatom chosen from O and N in addition to the nitrogen atom, optionally substituted with one or several groups selected from halo, nitro ($NO_2$), cyano (CN), oxo (=O), ($C_1$-$C_6$)alkyl, OH, $CO_2H$, ($C_1$-$C_6$)alkoxy, $CO_2$—($C_1$-$C_6$)alkyl and $NR_{28}R_{29}$.

6. The compound according to claim 1, wherein:
$R_0$ and $R_5$ are independently of each other, H or halo,
$R_2$, $R_3$ and $R_4$ are, independently of one another, H, halo, OH, ($C_1$-$C_6$)alkoxy, (($C_1$-$C_6$)alkyl)-carbonyloxy, $NO_2$, $NH_2$, ($C_1$-$C_6$)alkylamino, di($C_1$-$C_6$)alkylamino, (($C_1$-$C_6$)alkyl)-carbonylamino or (($C_1$-$C_6$)alkyl)-carbonyl (($C_1$-$C_6$)alkyl amino),
$R_6$ and $R_9$ are, independently of each other, H, halo, OH, ($C_1$-$C_6$)alkoxy, $NH_2$, ($C_1$-$C_6$)alkylamino or di($C_1$-$C_6$)alkylamino, and
$R_7$ and $R_8$ are, independently of one another, selected from H; halo; cyano (CN); $R_{10}$; $OR_{11}$; $NR_{15}R_{16}$; and a 5- or 6-membered saturated heterocycle comprising one or two heteroatoms chosen from O and N, optionally substituted with one or several groups selected from halo, oxo (=O), ($C_1$-$C_6$)alkyl, OH, ($C_1$-$C_6$)alkoxy, $NH_2$, ($C_1$-$C_6$)alkylamino and di($C_1$-$C_6$)alkylamino; with:
$R_{10}$, $R_{11}$, $R_{19}$, $R_{22}$ and $R_{23}$ being, independently of one another, H or a ($C_1$-$C_6$)alkyl group optionally substituted with one or several groups selected from halo, OH, ($C_1$-$C_6$)alkoxy, and $NR_{26}R_{27}$, and
$R_{15}$ and $R_{16}$ being, independently of each other, H or a ($C_1$-$C_6$)alkyl group optionally substituted with one or several groups selected from halo, OH, ($C_1$-$C_6$)alkoxy, and $NR_{26}R_{27}$, or
$R_{15}$ and $R_{16}$ forming together, with the nitrogen atom which carries them, a 5- or 6-membered saturated heterocycle optionally comprising one heteroatom chosen from O and N in addition to the nitrogen atom carrying the $R_{15}$ and $R_{16}$ groups, optionally substituted with one or several groups selected from halo, oxo (=O), ($C_1$-$C_6$)alkyl, OH, ($C_1$-$C_6$)alkoxy and $NR_{28}R_{29}$.

7. The compound according to claim 1, wherein, in the definition of $R_2$, $R_3$, $R_4$, $R_5$, $R_6$, $R_7$, $R_8$ and $R_9$, the heterocycle is selected from pyrrolidine, tetrahydrofurane, piperidine, tetrahydropyrane, morpholine, piperazine, azepane and diazepane, and in the definitions of $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$ and $R_{30}$, the heterocycle is selected from pyrrolidine, piperidine, morpholine, piperazine, azepane and diazepane.

8. The compound according to claim 1, wherein, when $R_4$ and $R_6$ form together a chain, this chain is a chain of formula —$X_1$-A-$X_2$— where:
$X_1$ and $X_2$ are, independently of each other, O, S or $NR_{30}$, and A is a saturated hydrocarbon chain comprising 2 to 8 carbon atoms optionally substituted with one or several groups selected from halo and ($C_1$-$C_6$)alkyl, where one to five non-adjacent carbon atoms of the saturated hydrocarbon chain are optionally replaced with O, S or $NR_{30}$.

9. The compound according to claim 8, wherein, when $R_4$ and $R_6$ form together a chain, this chain is a chain of formula —$(OCH_2CH_2)_nO$— with n representing an integer comprised between 1 and 3.

10. The compound according to claim 1, wherein $R_4$ and $R_6$ are, independently of each other, selected from H; halo; nitro ($NO_2$); cyano (CN); $R_{10}$; $OR_{11}$; $SR_{12}$; $S(O)R_{13}$; $SO_2R_{14}$; $NR_{15}R_{16}$; $C(O)R_{17}$; $CO_2R_{18}$; $OC(O)R_{19}$; $C(O)NR_{20}R_{21}$; $NR_{22}C(O)R_{23}$; and a 3- to 7-membered saturated or unsaturated heterocycle comprising one to three heteroatoms chosen from O, N and S, optionally substituted with one or several groups selected from halo, nitro ($NO_2$), cyano (CN), oxo (=O), ($C_1$-$C_6$)alkyl, OH, $CO_2H$, ($C_1$-$C_6$)alkoxy, $CO_2$—($C_1$-$C_6$)alkyl and $NR_{24}R_{25}$.

11. The compound according to claim 10, wherein $R_4$ and $R_6$ are, independently of each other, selected from H, halo, OH, ($C_1$-$C_6$)alkoxy, $NH_2$, ($C_1$-$C_6$)alkylamino and di($C_1$-$C_6$)alkylamino.

12. The compound according to claim 1, selected from the following compounds

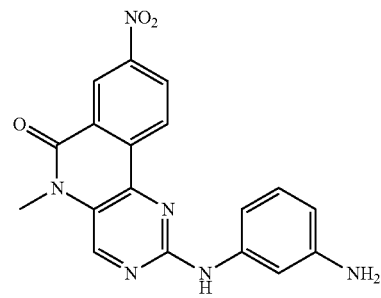

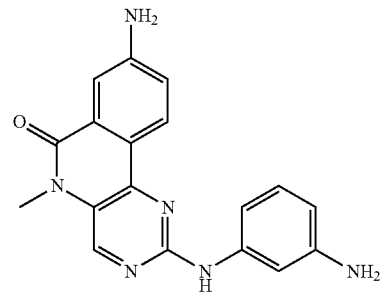

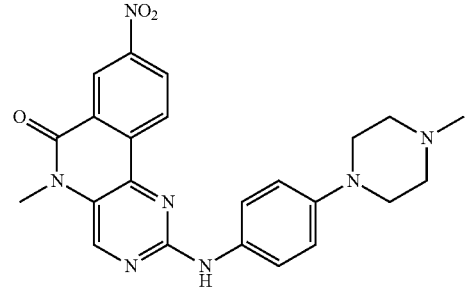

69
-continued
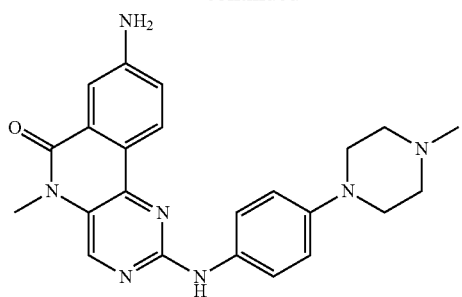
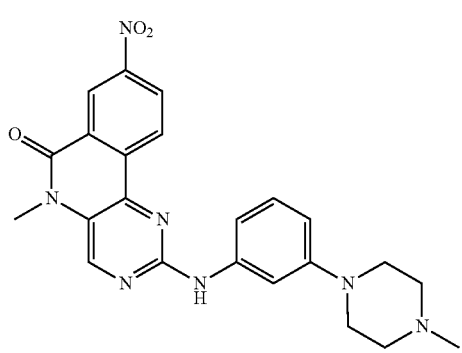
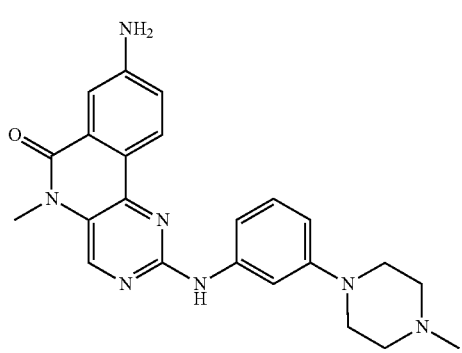
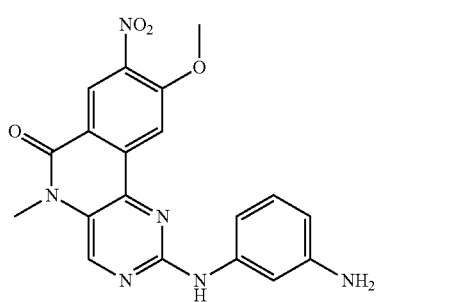
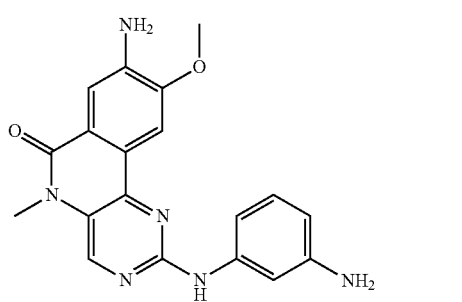
70
-continued
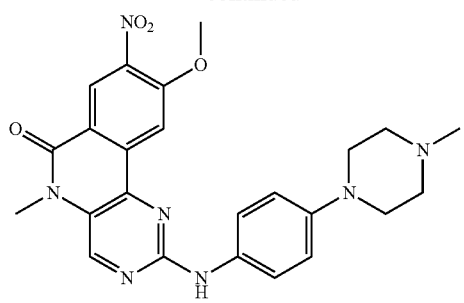
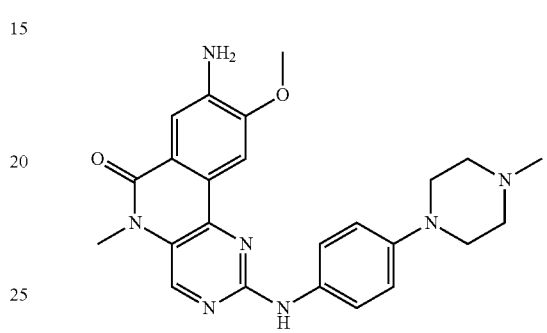
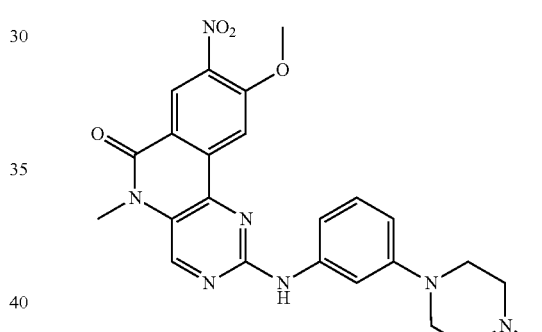
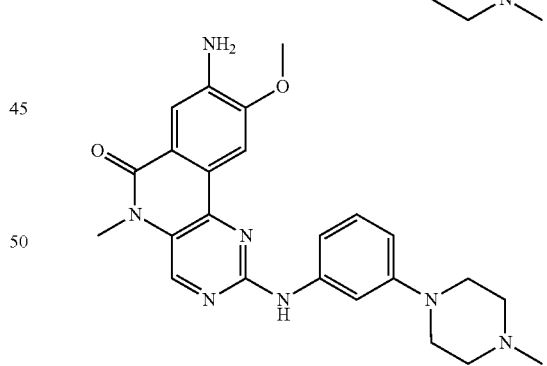
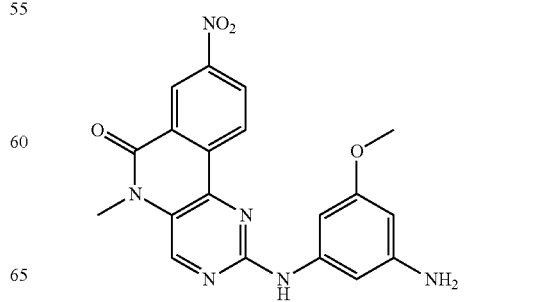

-continued
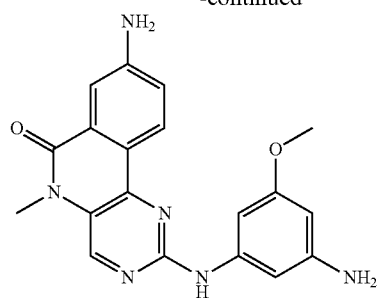
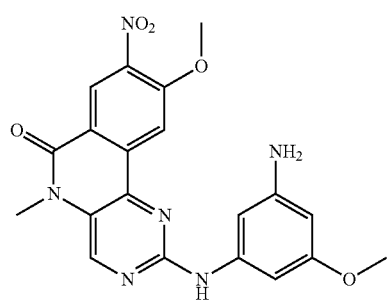
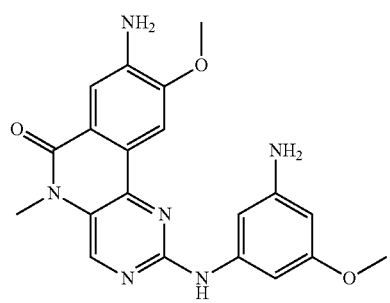
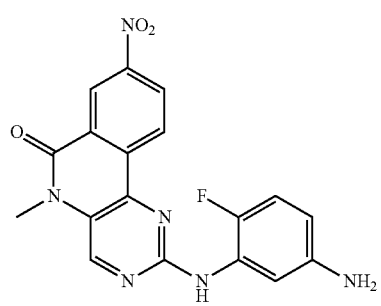
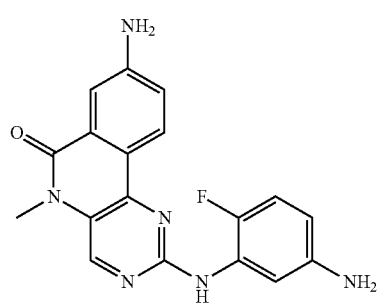
-continued
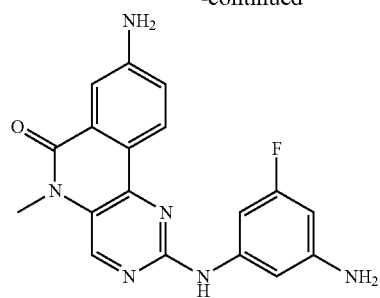
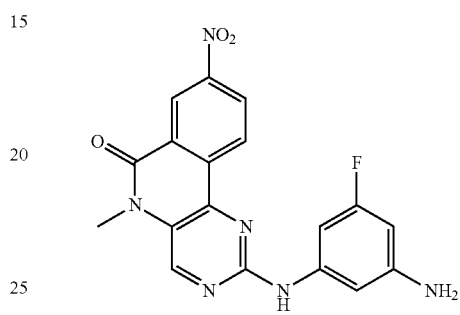
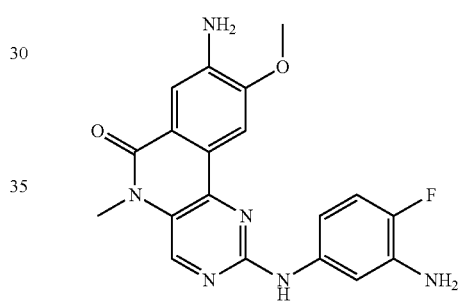
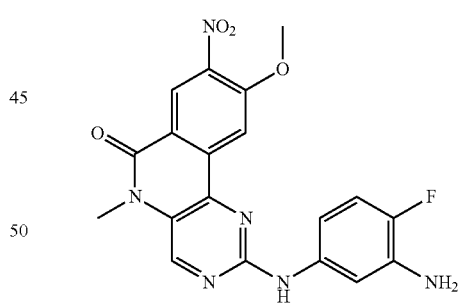
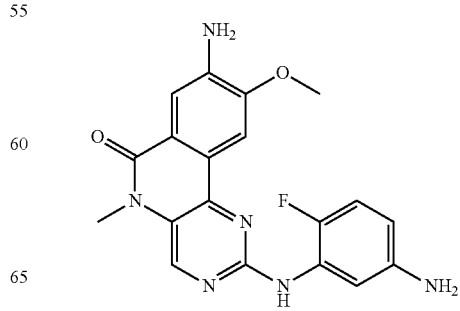

73
-continued
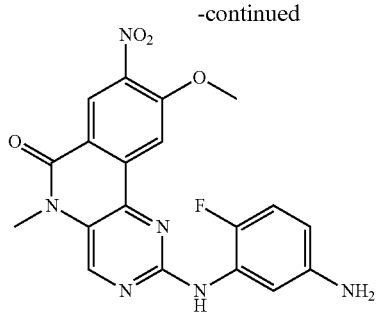
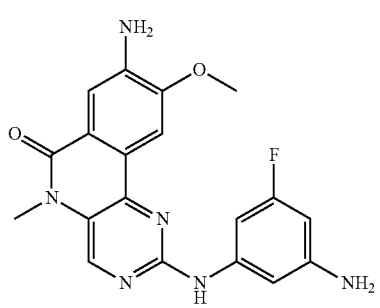
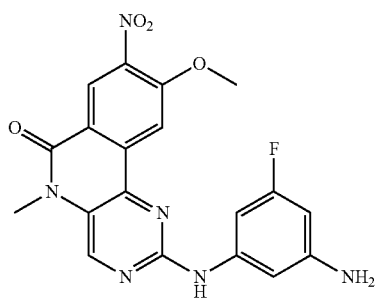
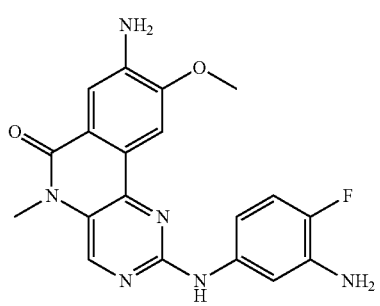
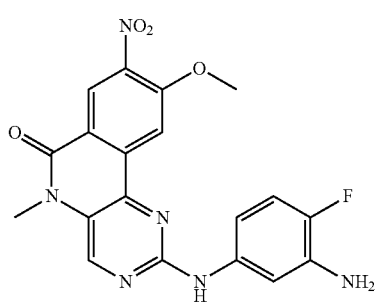
74
-continued
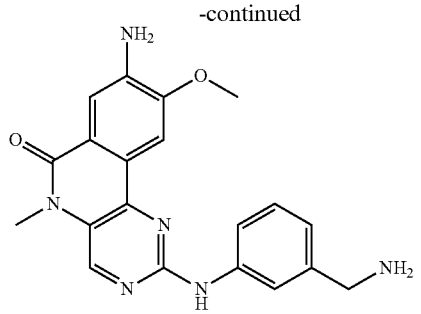
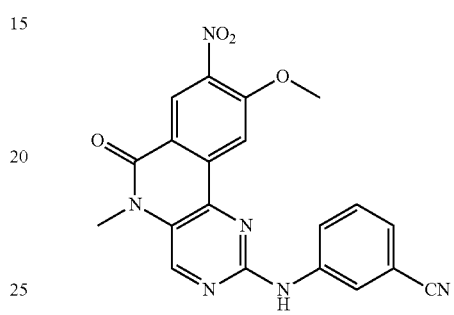
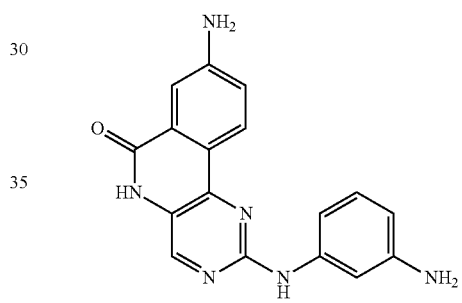
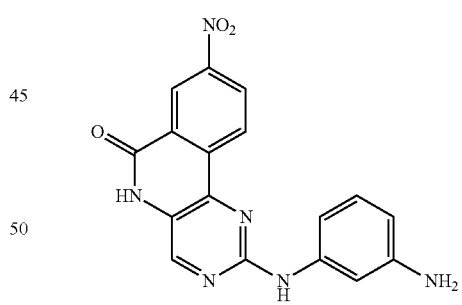
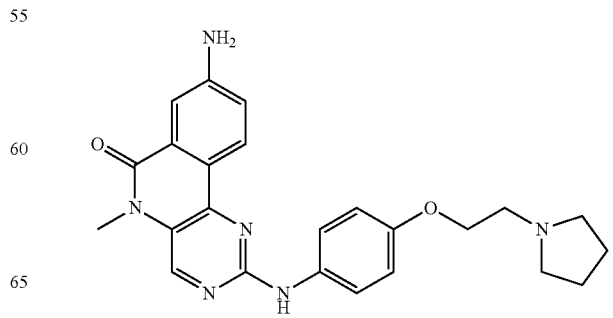

-continued
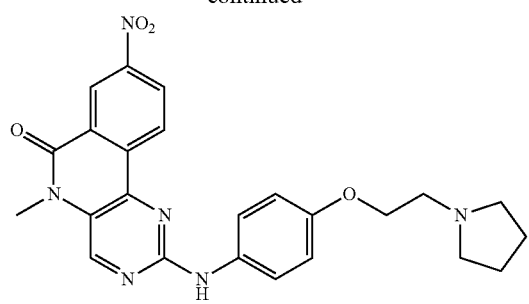
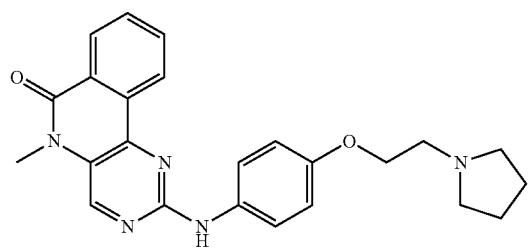 [SMILES: Cn1c(=O)c2ccccc2c2nc(Nc3ccc(OCCN4CCCC4)cc3)ncc21]
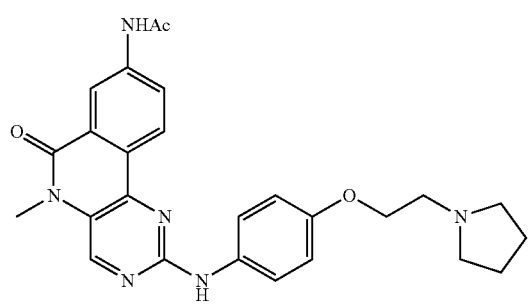
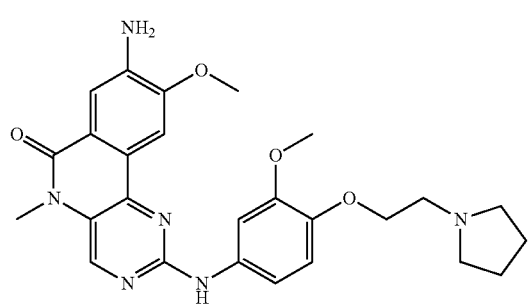 [SMILES: COc1cc(Nc2ncc3c(n2)c2cc(OC)c([N+](=O)[O-])cc2c(=O)n3C)ccc1OCCN1CCCC1]
-continued
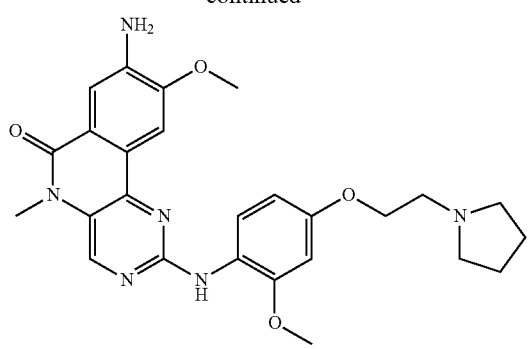
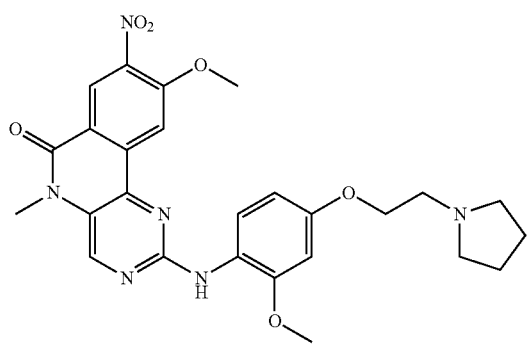 [SMILES: COc1cc(OCCN2CCCC2)ccc1Nc1ncc2c(n1)c1cc(OC)c([N+](=O)[O-])cc1c(=O)n2C]
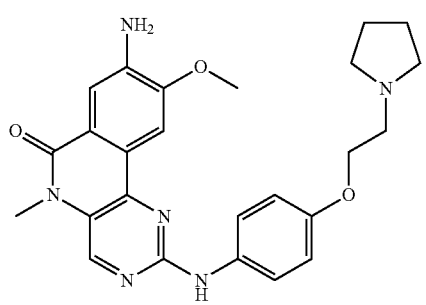 [SMILES: COc1cc2c(cc1[N+](=O)[O-])c(=O)n(C)c1cnc(Nc3ccc(OCCN4CCCC4)cc3)nc21]
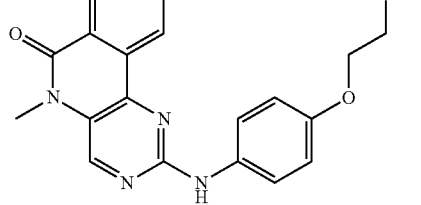

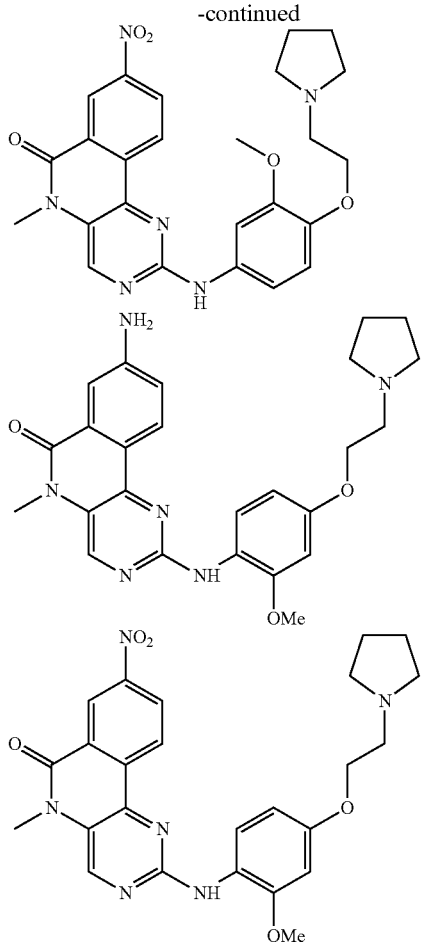

and the pharmaceutically acceptable salts thereof.

13. A pharmaceutical composition comprising at least one compound according to claim 1 and at least one pharmaceutically acceptable excipient.

14. The pharmaceutical composition according to claim 13, further comprising at least another active principle.

15. A pharmaceutical composition comprising:
(i) at least one compound according to claim 1, and
(ii) at least another active principle,
as a combination product for a simultaneous, separate or sequential use.

16. A process to prepare a compound according to claim 1 comprising a coupling reaction between:
a compound of the following formula (A):

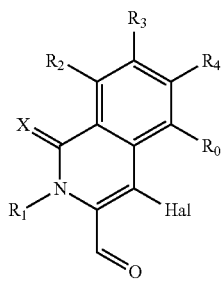

(A)

where X, $R_0$, $R_1$, $R_2$, $R_3$ and $R_4$ are as defined in claim 1, the $R_2$, $R_3$ and $R_4$ groups being optionally in a protected form, and Hal is a halogen atom, and
a compound of the following formula (B):

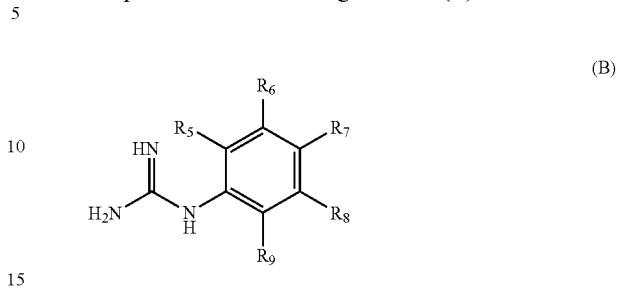

(B)

where $R_5$, $R_6$, $R_7$, $R_8$ and $R_9$ are as defined in claim 1, said groups being optionally in a protected form,
in the presence of a base,
followed by a deprotection of the $R_2$, $R_3$, $R_4$, $R_5$, $R_6$, $R_7$, $R_8$ and/or $R_9$ groups when they are in a protected form.

17. A process to prepare a compound according to claim 8 in which $R_4$ and $R_6$ form together a chain of formula —$X_1$-A-$X_2$— as defined in claim 8 comprising a coupling reaction between:
a compound of the following formula (II):

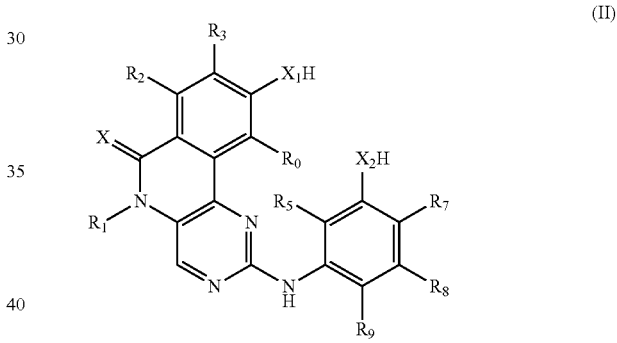

(II)

in which:
$X_1$ and $X_2$ are as defined in claim 8,
X is selected from O, NH and S,
$R_0$ is H; halo; ($C_1$-$C_6$)alkyl; ($C_1$-$C_6$)haloalkyl; ($C_1$-$C_6$)alkoxy; or ($C_1$-$C_6$)haloalkoxy,
$R_1$ is selected from H and ($C_1$-$C_3$)alkyl,
$R_2$, $R_3$, $R_5$, $R_7$, $R_8$ and $R_9$ are, independently of one another, selected from H; halo; nitro ($NO_2$); cyano (CN); $R_{10}$; $OR_{11}$; $SR_{12}$; $S(O)R_{13}$; $SO_2R_{14}$; $NR_{15}R_{16}$; $C(O)R^{17}$; $CO_2R_{18}$; $OC(O)R_{19}$; $C(O)NR_{20}R_{21}$; $NR_{22}C(O)R_{23}$; and a 3- to 7-membered saturated or unsaturated heterocycle, comprising one to three heteroatoms chosen from O, N and S, optionally substituted with one or several groups selected from halo, nitro ($NO_2$), cyano (CN), oxo (=O), ($C_1$-$C_6$)alkyl, OH, $CO_2$H, ($C_1$-$C_6$)alkoxy, $CO_2$—($C_1$-$C_6$)alkyl and $NR_{24}R_{25}$,
$R_{10}$, $R_{11}$, $R_{12}$, $R_{13}$, $R_{14}$, $R_{17}$, $R_{18}$, $R_{19}$, $R_{22}$ and $R_{23}$ are, independently of one another, H or a ($C_1$-$C_6$) alkyl, ($C_2$-$C_6$)alkenyl or ($C_2$-$C_6$)alkynyl group optionally substituted with one or several groups selected from halo, nitro ($NO_2$), cyano (CN), OH, $CO_2$H, ($C_1$-$C_6$)alkoxy, $CO_2$—($C_1$-$C_6$)alkyl and $NR_{26}R_{27}$, $R_{15}$, $R_{16}$, $R_{20}$ and $R_{21}$ are, independently of one another, H or a $(C_1\text{-}C_6)$alkyl, $(C_2\text{-}C_6)$alkenyl or $(C_2\text{-}C_6)$alkynyl group optionally substituted with one or several groups selected from halo, nitro ($NO_2$), cyano (CN), OH, $CO_2H$, $(C_1\text{-}C_6)$alkoxy, $CO_2\text{—}(C_1\text{-}C_6)$alkyl and $NR_{26}R_{27}$, or $R_{15}$ and $R_{16}$ and/or $R_{20}$ and $R_{21}$ form together, with the nitrogen atom which carries them, a 3- to 7-membered saturated or unsaturated heterocycle optionally comprising one or two heteroatoms chosen from O, N and S in addition to the nitrogen atom, optionally substituted with one or several groups selected from halo, nitro ($NO_2$), cyano (CN), oxo (=O), $(C_1\text{-}C_6)$alkyl, OH, $CO_2H$, $(C_1\text{-}C_6)$alkoxy, $CO_2\text{—}(C_1\text{-}C_6)$alkyl and $NR_{28}R_{29}$, $R_{24}$, $R_{25}$, $R_{26}$, $R_{27}$, $R_{28}$ and $R_{29}$ are, independently of each other, H or a $(C_1\text{-}C_6)$alkyl group, or $R_{24}$ and $R_{25}$ and/or $R_{26}$ and $R_{27}$ and/or $R_{28}$ and $R_{29}$ form together, with the nitrogen atom which carries them, a 3- to 7-membered saturated or unsaturated heterocycle optionally comprising one or two heteroatoms chosen from O, N and S in addition to the nitrogen atom, optionally substituted with one or several groups selected from halo, oxo (=O) and $(C_1\text{-}C_6)$alkyl, and a compound of the following formula (III):

$$LG_1\text{-}A\text{-}LG_2 \quad (III)$$

in which A is as defined in claim 8 and $LG_1$ and $LG_2$ are, independently of each other, a leaving group such as Br, in the presence of a base.

18. The compound according to claim 5, wherein $R_{10}$, $R_{11}$, $R_{12}$, $R_{13}$, $R_{14}$, $R_{17}$, $R_{18}$, $R_{19}$, $R_{22}$, $R_{23}$ and $R_{30}$ are, independently of one another, H or a $(C_1\text{-}C_6)$alkyl group optionally substituted with one or several groups selected from halo, nitro ($NO_2$), cyano (CN), OH, $(C_1\text{-}C_6)$alkoxy and $NR_{26}R_{27}$, and $R_{15}$, $R_{16}$, $R_{20}$ and $R_{21}$ are, independently of one another, H or a $(C_1\text{-}C_6)$alkyl group optionally substituted with one or several groups selected from halo, nitro ($NO_2$), cyano (CN), OH, $(C_1\text{-}C_6)$alkoxy and $NR_{26}R_{27}$, or $R_{15}$ and $R_{16}$ and/or $R_{20}$ and $R_{21}$ form together, with the nitrogen atom which carries them, a 5- to 7-membered saturated or unsaturated heterocycle optionally comprising one heteroatom chosen from O and N in addition to the nitrogen atom, optionally substituted with one or several groups selected from halo, nitro ($NO_2$), cyano (CN), oxo (=O), $(C_1\text{-}C_6)$alkyl, OH, $(C_1\text{-}C_6)$alkoxy and $NR_{28}R_{29}$.

19. The compound according to claim 7, wherein, in the definition of $R_2$, $R_3$, $R_4$, $R_5$, $R_6$, $R_7$, $R_8$ and $R_9$, the heterocycle is selected from pyrrolidine, piperidine, morpholine and piperazine, and in the definitions of $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$ and $R_{30}$, the heterocycle is selected from pyrrolidine, piperidine, morpholine and piperazine.

20. The pharmaceutical composition according to claim 14, wherein the at least other active principle is an anticancer agent.

21. The pharmaceutical composition according to claim 15, wherein the at least other active principle is an anticancer agent.

22. A method for treating cancer comprising the administration to a person in need thereof of an effective amount of a compound according to claim 1.

* * * * *